(12) United States Patent
Fleischman et al.

(10) Patent No.: US 6,648,900 B2
(45) Date of Patent: Nov. 18, 2003

(54) ANASTOMOSIS SYSTEMS

(75) Inventors: Sidney D. Fleischman, Menlo Park, CA (US); Russell A. Houser, Livermore, CA (US); James G. Whayne, Chapel Hill, NC (US); Thomas H. Campbell, Brentwood, CA (US); Patrick M. Owens, Half Moon Bay, CA (US)

(73) Assignee: Converge Medical, Inc., Sunnyvale, CA (US)

( * ) Notice: Subject to any disclaimer, the term of this patent is extended or adjusted under 35 U.S.C. 154(b) by 154 days.

(21) Appl. No.: 09/997,619

(22) Filed: Nov. 28, 2001

(65) Prior Publication Data

US 2002/0099393 A1 Jul. 25, 2002

Related U.S. Application Data

(63) Continuation of application No. 09/730,366, filed on Dec. 5, 2000, and a division of application No. 09/329,503, filed on Jun. 10, 1999.
(60) Provisional application No. 60/169,104, filed on Dec. 6, 1999, provisional application No. 60/151,863, filed on Sep. 1, 1999, and provisional application No. 60/111,948, filed on Dec. 11, 1998.

(51) Int. Cl.$^7$ .............................................. A61B 17/08
(52) U.S. Cl. ...................................... 606/153; 606/155
(58) Field of Search ................................ 606/151–156, 606/213

(56) References Cited

U.S. PATENT DOCUMENTS

| 4,214,587 A | 7/1980 | Sakura, Jr. |
|---|---|---|
| 4,366,819 A | 1/1983 | Kaster |
| 4,368,736 A | 1/1983 | Kaster |
| 4,607,637 A | 8/1986 | Berggren et al. |
| 4,624,257 A | 11/1986 | Berggren et al. |
| 4,657,019 A | 4/1987 | Walsh et al. |
| 4,665,906 A | 5/1987 | Jervis |

(List continued on next page.)

FOREIGN PATENT DOCUMENTS

| EP | 0 824 901 A2 | 2/1998 |
|---|---|---|
| WO | WO 96/22745 A1 | 8/1996 |

(List continued on next page.)

OTHER PUBLICATIONS

Cragg, A.H. et al. (1982). "Endovascular Diathermic Vessel Occlusion," *Radiology* 144:303–308.
Gorisch, W. et al. (1982). "Heat–Induced Contraction of Blood Vessels," *Lasers in Surgery and Medicine* 2:1–13.
Heijmen, R.H. et al., (1999). "A Novel One–Shot Anastomotic Stapler Prototype for Coronary Bypass Grafting on the Bearing Heart: Feasibility in the Pig," *Journal of Thoracic and Cardiovascular Surgery* 117(1): 117–125.
Yusuf, S.W. et al. (1994). "Transfermoral Endolumimal Repair of Abdominal Aortic Aneurysm with Bifuricated Graft," *Lancet* 344(8923): 650–651.

*Primary Examiner*—David O. Reip
(74) *Attorney, Agent, or Firm*—Carol M. LaSalle; Bozicevic, Field & Francis LLP

(57) ABSTRACT

An end-side anastomosis system including a fitting including a base for attachment to a graft, the base be configured to form a seal with an opening in a host vessel wall a leading petal having a cross-section with a radius of curvature approximating a radius of curvature of the host vessel, the leading petal being configured to dilate the host vessel wall opening while advancing the fitting through the opening and a rear petal, the rear petal being deflectable to be advanced through the host vessel opening.

14 Claims, 54 Drawing Sheets

U.S. PATENT DOCUMENTS

| | | | |
|---|---|---|---|
| 4,787,386 A | 11/1988 | Walsh et al. |
| 4,917,087 A | 4/1990 | Walsh et al. |
| 4,917,090 A | 4/1990 | Berggren et al. |
| 4,917,091 A | 4/1990 | Berggren et al. |
| 4,950,227 A | 8/1990 | Savin et al. |
| 5,067,957 A | 11/1991 | Jervis |
| 5,078,736 A | 1/1992 | Behl |
| 5,156,613 A | 10/1992 | Sawyer |
| 5,190,546 A | 3/1993 | Jervis |
| 5,234,447 A | 8/1993 | Kaster et al. |
| 5,391,156 A | 2/1995 | Hildwein et al. |
| 5,405,322 A | 4/1995 | Lennox et al. |
| 5,443,497 A | 8/1995 | Venbrux |
| 5,503,635 A | 4/1996 | Sauer et al. |
| 5,571,167 A | 11/1996 | Maginot |
| 5,591,226 A | 1/1997 | Trerotola et al. |
| 5,597,378 A | 1/1997 | Jervis |
| 5,628,784 A | 5/1997 | Strecker |
| 5,657,429 A | 8/1997 | Wang et al. |
| 5,665,117 A | 9/1997 | Rhodes |
| 5,669,934 A | 9/1997 | Sawyer |
| 5,676,670 A | 10/1997 | Kim |
| 5,690,675 A | 11/1997 | Sawyer et al. |
| 5,695,504 A | 12/1997 | Gifford, III et al. |
| 5,697,968 A | 12/1997 | Rogers et al. |
| 5,702,418 A | 12/1997 | Ravenscroft |
| 5,713,917 A | 2/1998 | Leonhardt et al. |
| 5,720,755 A | 2/1998 | Dakov |
| 5,725,544 A | 3/1998 | Rygaard |
| 5,728,133 A | 3/1998 | Kontos |
| 5,749,375 A | 5/1998 | Maginot |
| 5,749,895 A | 5/1998 | Sawyer et al. |
| 5,755,775 A | 5/1998 | Trerotola et al. |
| 5,755,778 A | 5/1998 | Kleshinki |
| 5,762,458 A | 6/1998 | Wang et al. |
| 5,779,718 A | 7/1998 | Green et al. |
| 5,797,920 A | 8/1998 | Kim |
| 5,797,934 A | 8/1998 | Rygaard |
| 5,810,884 A | 9/1998 | Kim |
| 5,814,005 A | 9/1998 | Barra et al. |
| 5,824,015 A | 10/1998 | Sawyer |
| 5,861,003 A | 1/1999 | Latson et al. |
| 5,868,759 A | 2/1999 | Peyser et al. |
| 5,868,761 A | 2/1999 | Nicholas et al. |
| 5,868,770 A | 2/1999 | Rygaard |
| 5,871,536 A | 2/1999 | Lazarus |
| 5,931,842 A | 8/1999 | Goldsteen et al. |
| 5,934,286 A | 8/1999 | Maginot |
| 5,938,672 A | 8/1999 | Nash |
| 5,938,696 A | 8/1999 | Goicoechea et al. |
| 5,944,019 A | 8/1999 | Knudson et al. |
| 5,944,730 A | 8/1999 | Nobles et al. |
| 5,944,738 A | 8/1999 | Amplatz et al. |
| 5,944,750 A | 8/1999 | Tanner et al. |
| 5,954,735 A | 9/1999 | Rygaard |
| 5,957,940 A | 9/1999 | Tanner et al. |
| 5,964,782 A | 10/1999 | Lafontaine et al. |
| 5,968,053 A | 10/1999 | Revelas |
| 5,968,089 A | 10/1999 | Krajicek |
| 5,968,090 A | 10/1999 | Ratcliff et al. |
| 5,972,017 A | 10/1999 | Berg et al. |
| 5,972,023 A | 10/1999 | Tanner et al. |
| 5,976,178 A | 11/1999 | Goldsteen et al. |
| 5,979,455 A | 11/1999 | Maginot |
| 5,984,955 A | 11/1999 | Wisselink |
| 5,989,276 A | 11/1999 | Houser et al. |
| 5,989,287 A | 11/1999 | Yang et al. |
| 5,993,468 A | 11/1999 | Rygaard |
| 6,001,124 A | 12/1999 | Bachinski |
| 6,004,347 A | 12/1999 | McNamara et al. |
| 6,007,576 A | 12/1999 | McClellan |
| 6,010,529 A | 1/2000 | Herweck et al. |
| 6,017,352 A | 1/2000 | Nash et al. |
| 6,019,788 A | 2/2000 | Butters et al. |
| 6,030,370 A | 2/2000 | Kupka et al. |
| 6,030,392 A | 2/2000 | Dakov |
| 6,030,395 A | 2/2000 | Nash et al. |
| 6,036,702 A | 3/2000 | Bachinski et al. |
| 6,036,703 A | 3/2000 | Evans et al. |
| 6,036,705 A | 3/2000 | Nash et al. |
| 6,048,362 A | 4/2000 | Berg |
| 6,056,762 A | 5/2000 | Nash et al. |
| 6,059,824 A | 5/2000 | Taheri |
| 6,063,114 A | 5/2000 | Nash et al. |
| 6,068,654 A | 5/2000 | Berg et al. |
| 6,071,305 A | 6/2000 | Brown et al. |
| 6,074,416 A | 6/2000 | Berg et al. |
| 6,113,612 A | 9/2000 | Swanson et al. |
| 6,117,147 A | 9/2000 | Simpson et al. |
| 6,120,432 A | 9/2000 | Sullivan et al. |
| 6,149,681 A | 11/2000 | Houser et al. |
| 6,293,955 B1 | 9/2001 | Houser et al. |

FOREIGN PATENT DOCUMENTS

| | | |
|---|---|---|
| WO | WO 97/13463 A1 | 4/1997 |
| WO | WO 97/13471 A1 | 4/1997 |
| WO | WO 97/16122 A1 | 5/1997 |
| WO | WO 97/27893 A1 | 8/1997 |
| WO | WO 97/27897 A1 | 8/1997 |
| WO | WO 97/27898 A1 | 8/1997 |
| WO | WO 97/31575 A1 | 9/1997 |
| WO | WO 97/40754 A1 | 11/1997 |
| WO | WO 97/43961 A1 | 11/1997 |
| WO | WO 98/03118 A1 | 1/1998 |
| WO | WO 98/06356 A1 | 2/1998 |
| WO | WO 98/07399 A1 | 2/1998 |
| WO | WO 98/08456 A1 | 3/1998 |
| WO | WO 98/19608 A1 | 5/1998 |
| WO | WO 98/19618 A1 | 5/1998 |
| WO | WO 98/19625 A3 | 5/1998 |
| WO | WO 98/19625 A2 | 5/1998 |
| WO | WO 98/19629 A2 | 5/1998 |
| WO | WO 98/19630 A2 | 5/1998 |
| WO | WO 98/19631 A1 | 5/1998 |
| WO | WO 98/19632 A1 | 5/1998 |
| WO | WO 98/19634 A2 | 5/1998 |
| WO | WO 99/63910 A1 | 12/1999 |
| WO | WO 99/65409 A1 | 12/1999 |
| WO | WO 00/15144 A1 | 3/2000 |
| WO | WO 00/53104 A1 | 9/2000 |
| WO | WO 01/41653 A3 | 6/2001 |
| WO | WO 01/41653 A2 | 6/2001 |

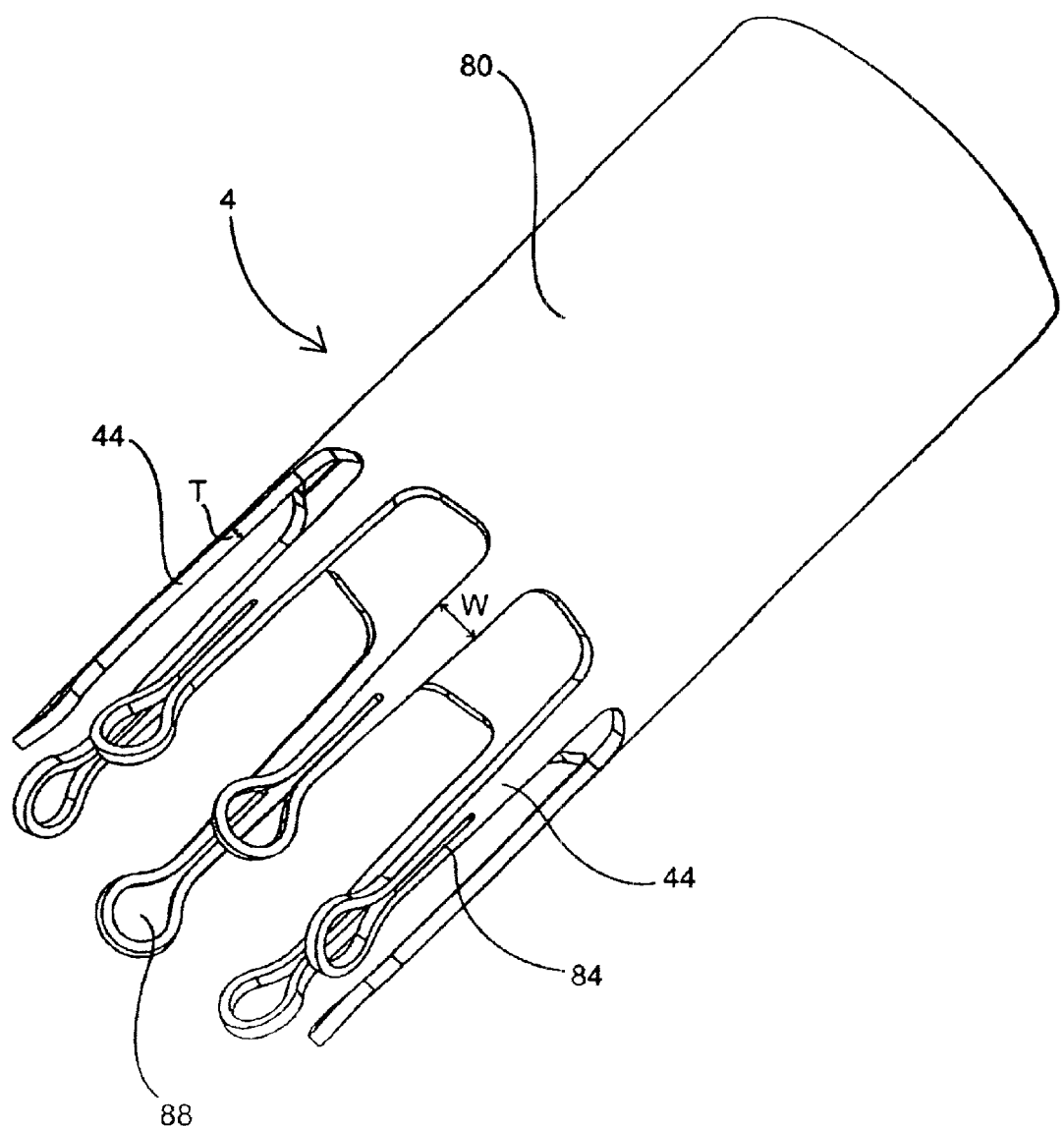

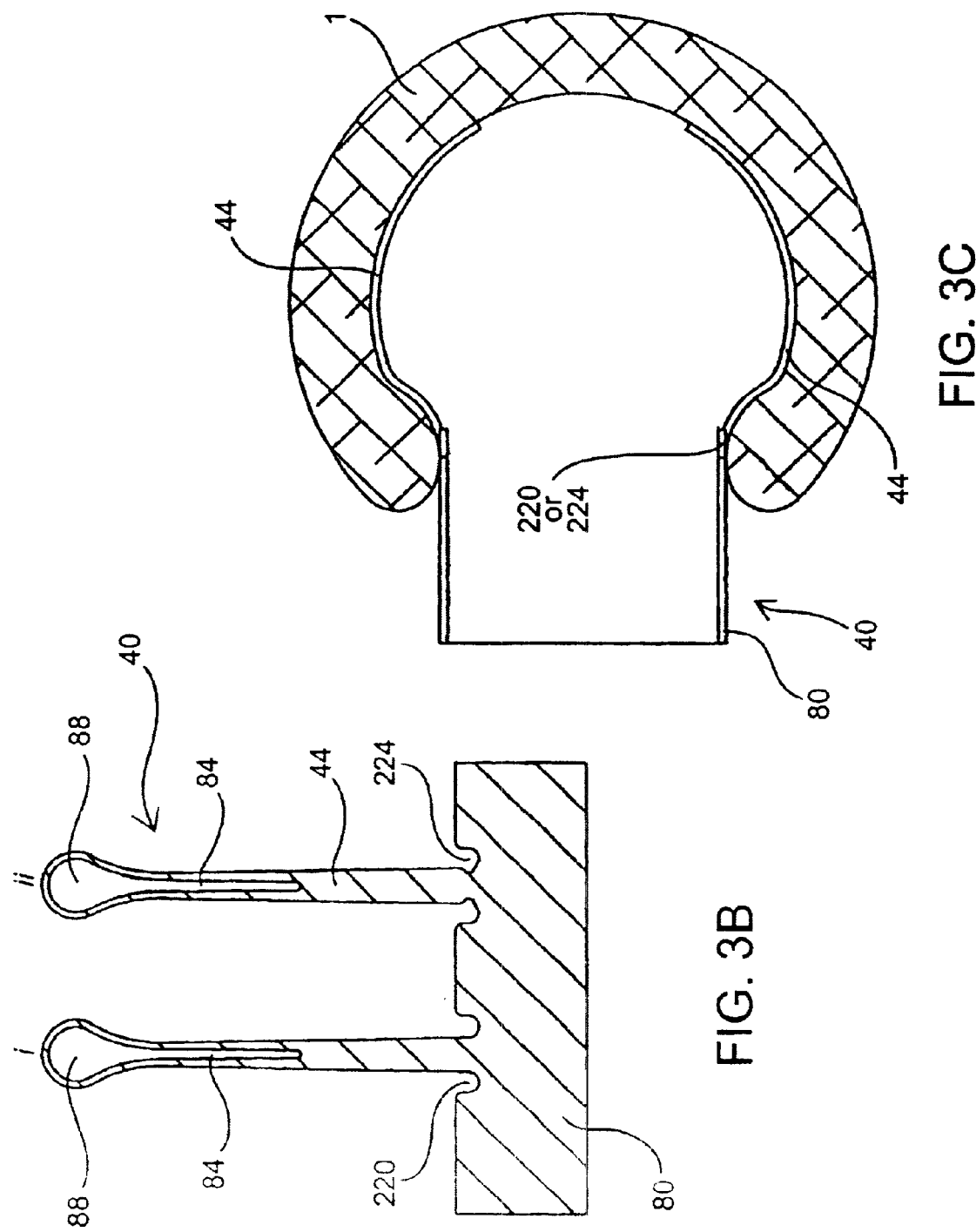

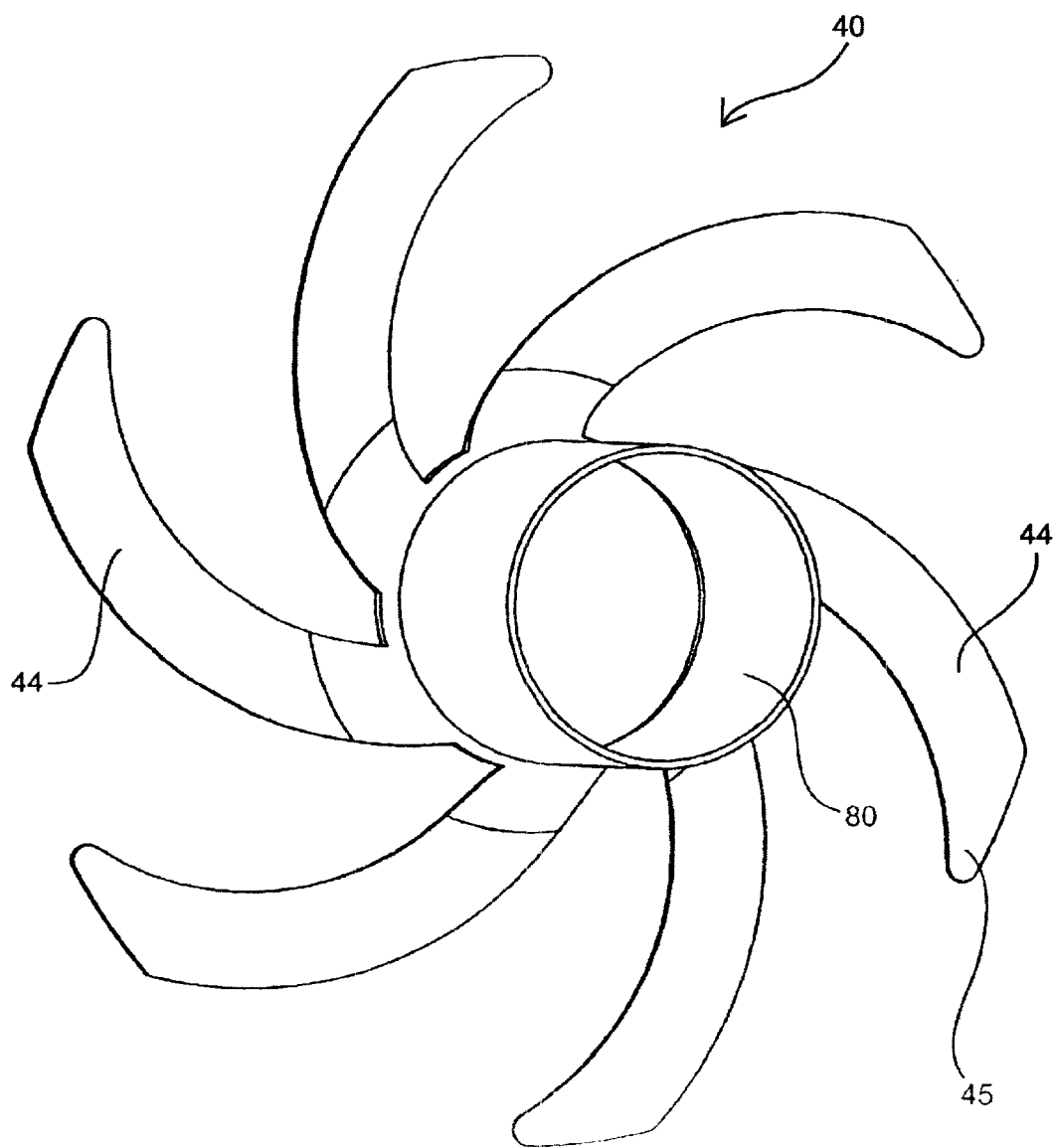

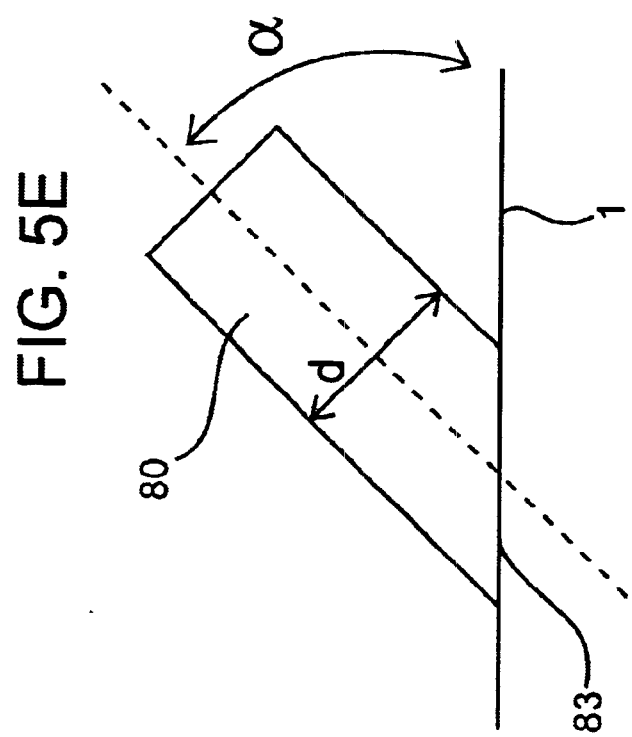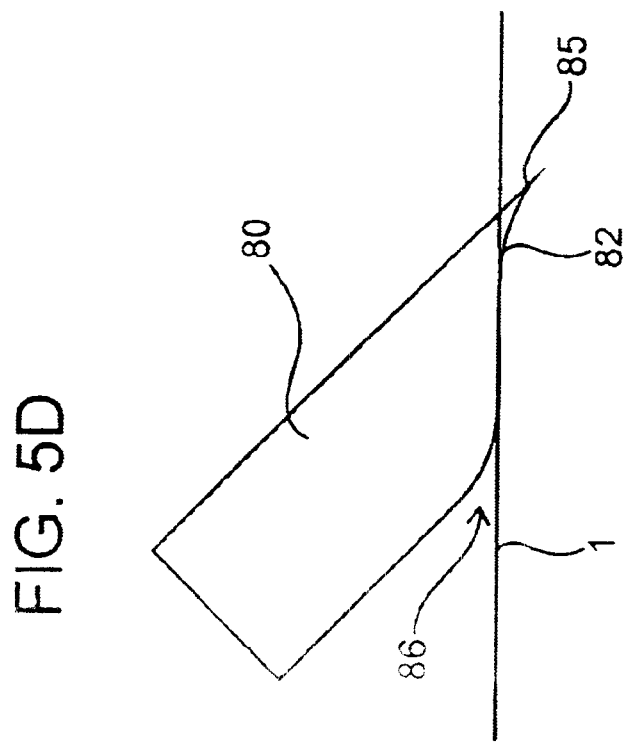

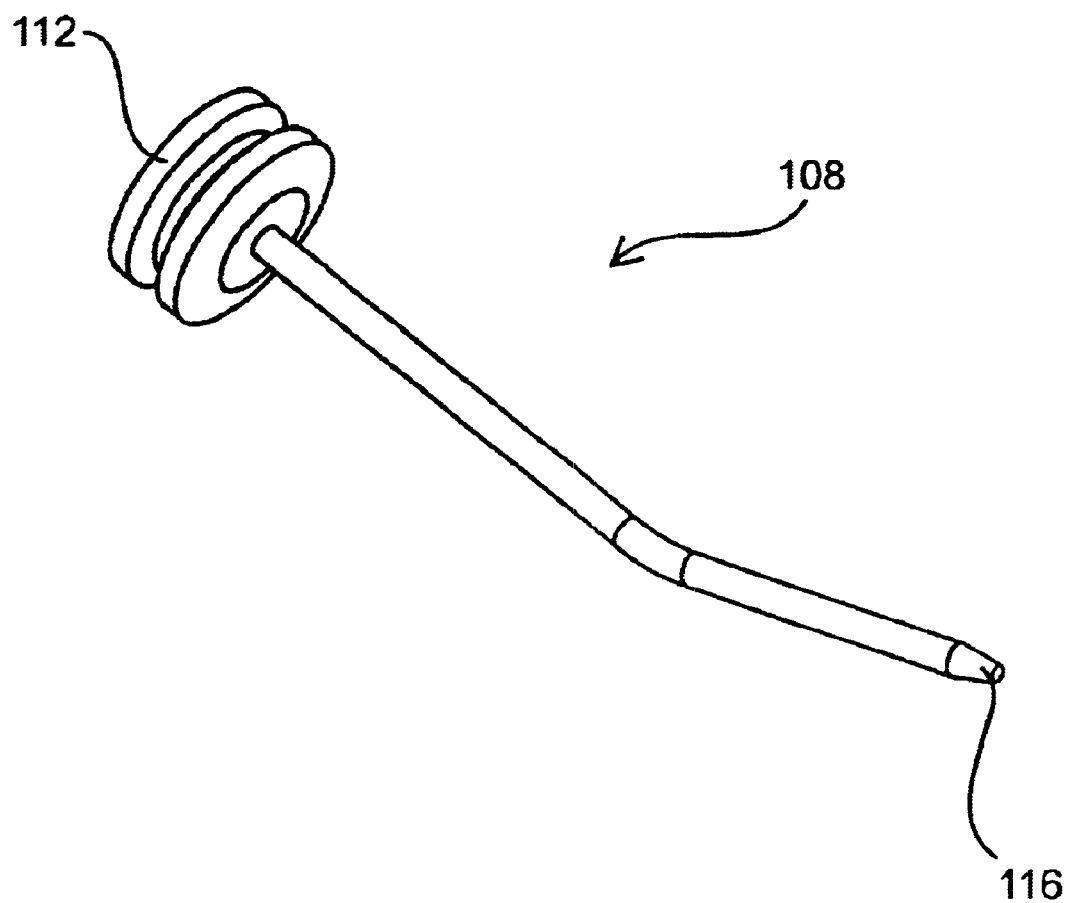

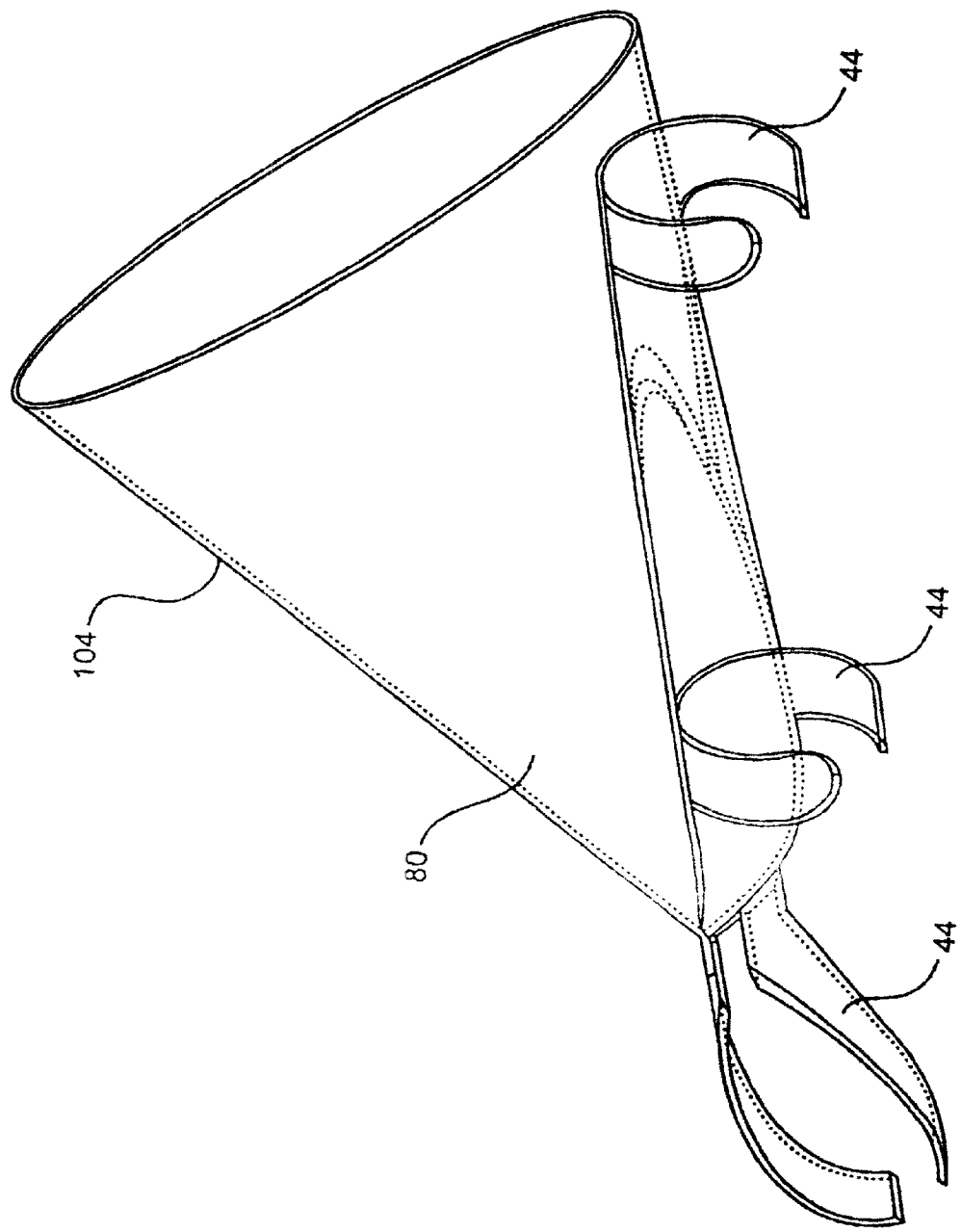

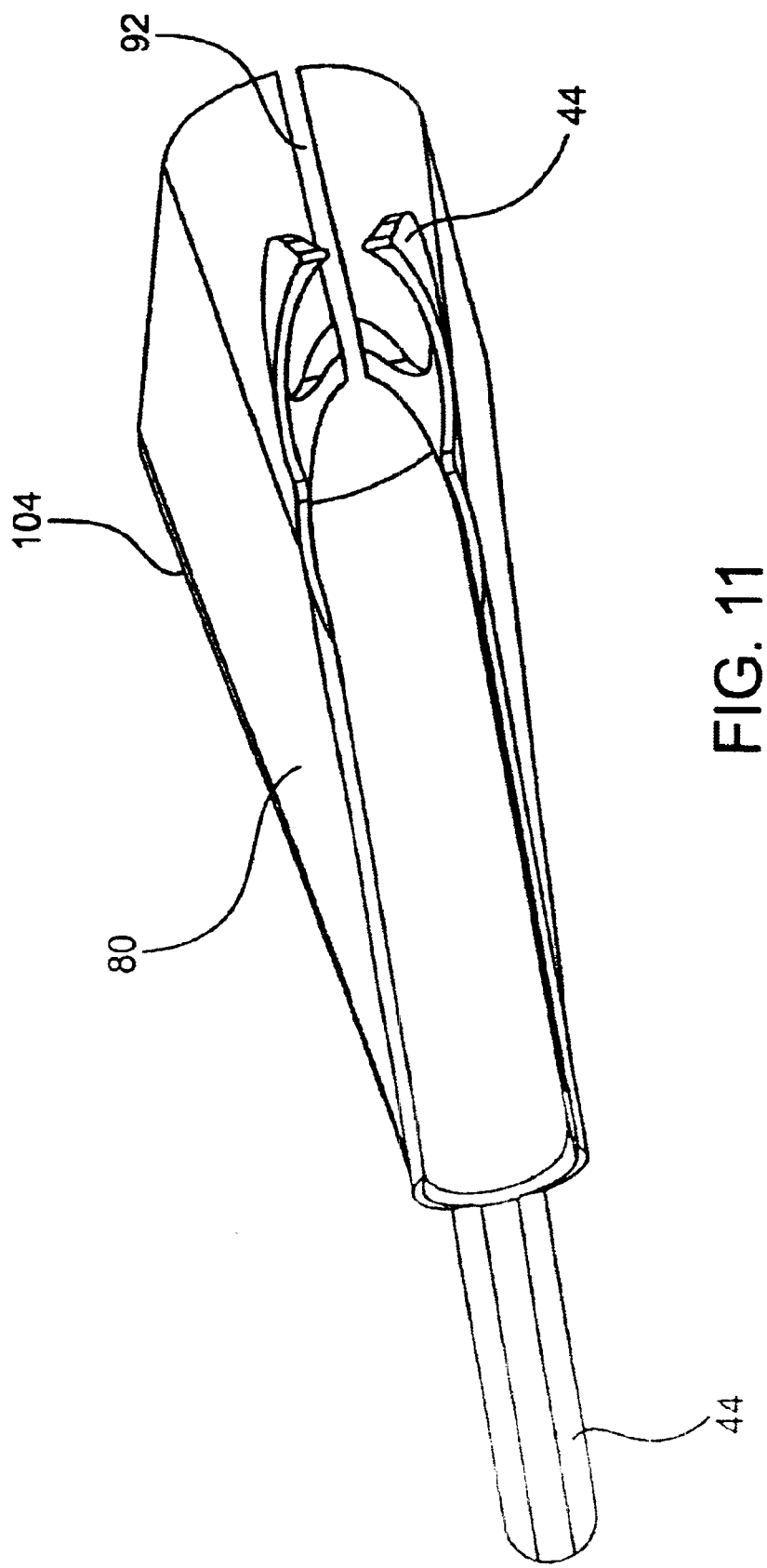

FIG. 15B
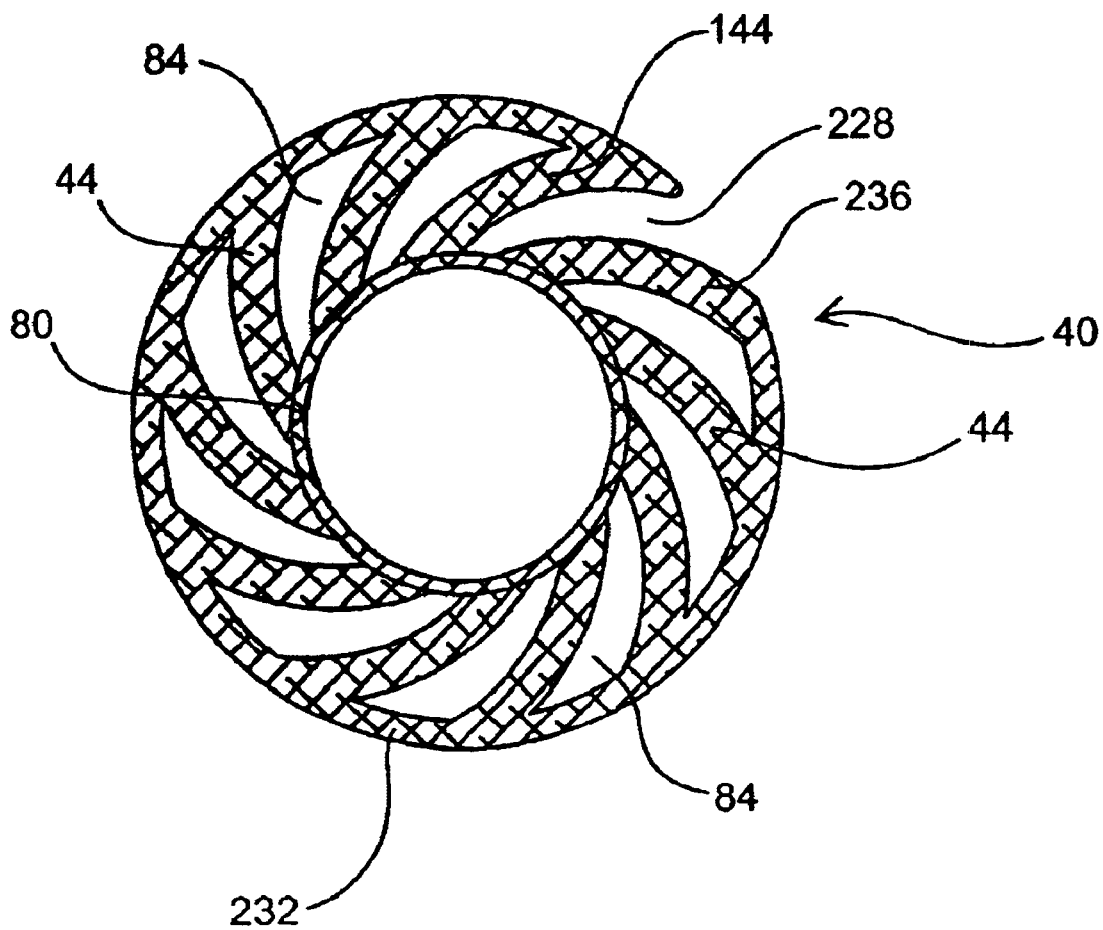
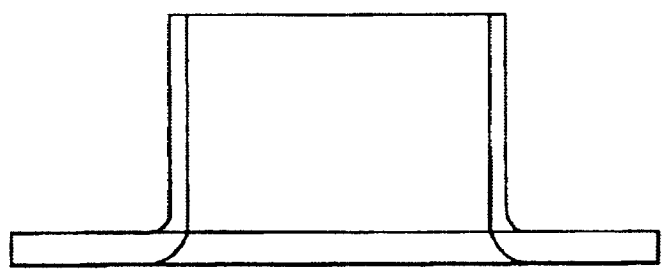

ANASTOMOSIS SYSTEMS

CROSS-REFERENCE TO RELATED APPLICATIONS

This application is a continuation of U.S. patent application Ser. No. 09/730,366 filed Dec. 5, 2000, which claims the benefit of U.S. Provisional Patent Application Serial No. 60/169,104 filed Dec. 6, 1999, U.S. Provisional Patent Application Serial No. 60/151,863 filed Sep. 1, 1999 and divisional Patent application Ser. No. 09/329,503 filed Jun. 10, 1999 and is related to U.S. Provisional Patent Application Serial No. 60/111,948 filed Dec. 11, 1998, the entirety of each is incorporated herein by reference.

FIELD OF THE INVENTION

This invention relates to devices for deploying and securing the ends of bypass grafts designed to provide a fluid flow passage between at least two host vessel regions (or other tubular structure regions). More particularly, the invention relates to bypass grafts that are secured at target host vessel locations thereby producing a fluid flow passage from the first host vessel location through the bypass graft and to the second host vessel location. The bypass grafts and deployment systems of the invention do not require stopping or re-routing blood flow to perform an anastomosis between a bypass graft and a host vessel. Accordingly, this invention describes sutureless anastomosis systems that do not require cardiopulmonary bypass support when treating coronary artery disease.

Current techniques for producing anastomoses during coronary artery bypass grafting procedures involve placing the patient on cardiopulmonary bypass support, arresting the heart, and interrupting blood flow to suture, clip, or staple a bypass graft to the coronary artery and aorta. However, cardiopulmonary bypass support is associated with substantial morbidity and mortality.

This invention provides devices and methods to position and secure bypass grafts at host vessel locations without having to stop or re-route blood flow. Accordingly, this invention does not require cardiopulmonary bypass support and arresting the heart while producing anastomoses to the coronary arteries. In addition, this invention mitigates risks associated with suturing, clipping, or stapling the bypass graft to the host vessel(s); namely, bleeding at the attachment sites and collapsing of the vessel around the incision point.

The invention addresses vascular bypass graft treatment regimens requiring end—end anastomoses and end-side anastomoses to attach bypass grafts to host vessels. The scope of the invention includes improvements to the systems used to position and secure bypass grafts for treating vascular diseases such as atherosclerosis, arteriosclerosis, fistulas, aneurysms, occlusions, thromboses, and the like. The improvements to the bypass grafts and delivery systems of this invention also aid in attaching the ends of ligated vessels, replacing vessels harvested for bypass grafting procedures (e.g. radial artery), and re-establishing blood flow to branching vessels which would otherwise be occluded during surgical grafting procedures (e.g. the renal arteries during abdominal aortic aneurysm treatment). In addition, the invention addresses other applications such as, but not limited to, producing arterial to venous shunts for hemodialysis patients, bypassing lesions and scar tissue located in the fallopian tubes causing infertility, attaching the ureter to the kidneys during transplants, and treating gastrointestinal defects (e.g. occlusions, ulcers, obstructions, etc.).

BACKGROUND OF THE INVENTION

Stenosed blood vessels cause ischemia potentially leading to tissue infarction. Conventional techniques to treat partially or completely occluded vessels include balloon angioplasty, stent deployment, atherectomy, and bypass grafting.

Coronary artery bypass grafting (CABG) procedures to treat coronary artery disease have traditionally been performed through a thoracotomy with the patient placed on cardiopulmonary bypass support and using cardioplegia to induce cardiac arrest. Cardiac protection is required when performing bypass grafting procedures associated with prolonged ischemia times. Current bypass grafting procedures involve interrupting blood flow to suture or staple the bypass graft to the host vessel wall and create the anastomoses. When suturing, clipping, or stapling the bypass graft to the host vessel wall, a large incision is made through the host vessel and the bypass graft is sewn to the host vessel wall such that the endothelial layers of the bypass graft and vessel face each other. Bypass graft intima to host vessel intima apposition reduces the incidence of thrombosis associated with biological reactions that result from blood contacting the epithelial layer of a harvested bypass graft. This is especially relevant when using harvested vessels that have a small inner diameter (e.g. $\leq 2$ mm).

Less invasive attempts for positioning bypass grafts at target vessel locations have used small ports to access the anatomy. These approaches use endoscopic visualization and modified surgical instruments (e.g. clamps, scissors, scalpels, etc.) to position and suture the ends of the bypass graft at the host vessel locations. Attempts to eliminate the need for cardiopulmonary bypass support while performing CABG procedures have benefited from devices that stabilize the motion of the heart, retractors that temporarily occlude blood flow through the host vessel, and shunts that re-route the blood flow around the anastomosis site. Stabilizers and retractors still require significant time and complexity to expose the host vessel and suture the bypass graft to the host vessel wall. Shunts not only add to the complexity and length of the procedure, but they require a secondary procedure to close the insertion sites proximal and distal to the anastomosis site.

Attempts to automate formation of sutureless anastomoses have culminated into mechanical stapling devices. Mechanical stapling devices have been proposed for creating end—end anastomoses between the open ends of transected vessels. Berggren et al. propose an automatic stapling device for use in microsurgery (see, e.g., U.S. Pat. Nos. 4,607,637, 4,624,257, 4,917,090, and 4,917,091). This stapling device has mating sections containing pins that are locked together after the vessel ends are fed through lumens in the sections and everted over the pins. This stapling device maintains intima-to-intima apposition for the severed vessel ends but has a large profile and requires impaling the everted vessel wall with the pins. U.S. Pat. No. 4,214,587 to Sakura describes a mechanical end—end stapling device designed to reattach severed vessels. This device has a wire wound into a zigzag pattern to permit radial motion and contains pins bonded to the wire that are used to penetrate tissue. One vessel end is everted over and secured to the pins of the end—end stapling device, and the other vessel end is advanced over the end—end stapling device and attached with the pins. Another mechanical end—end device that inserts mating pieces into each open end of a severed vessel is disclosed in U.S. Pat. No. 5,503,635 to Sauer et al. Once positioned, the mating pieces snap together to bond the vessel ends. These end—end devices are amenable to reattaching severed vessels but are not suitable to producing end—end anastomoses between a bypass graft and an intact vessel, especially when exposure to the vessel is limited.

Mechanical stapling devices have also been proposed for end-side anastomoses. These devices are generally designed to insert bypass grafts, which can be attached to the mechanical devices, into the host vessel through a large incision and secure the bypass graft to the host vessel. Kaster describes vascular stapling apparatus for producing end-side anastomoses in U.S. Pat. Nos. 4,366,819, 4,368,736, and 5,234,447. Kaster's end-side apparatus is inserted through a large incision in the host vessel wall. The apparatus has an inner flange that is placed against the interior of the vessel wall, and a locking ring that is affixed to the fitting and contains spikes that penetrate into the vessel thereby securing the apparatus to the vessel wall. The bypass graft is itself secured to the apparatus in the everted or non-everted position through the use of spikes incorporated in the apparatus design.

U.S. Surgical has developed automatic clip appliers that replace suture stitches with clips (see, e.g., U.S. Pat. Nos. 5,868,761, 5,868,759, and 5,779,718). These clipping devices have been demonstrated to reduce the time required to produce the anastomosis but still involve making a large incision through the host vessel wall. As a result, blood flow through the host vessel must be interrupted while creating the anastomosis.

U.S. Pat. No. 5,695,504 to Gifford et al. discloses an end-side stapling device that secures harvested vessels to host vessel walls while maintaining intima-to-intima apposition. This stapling device is also inserted through a large incision in the host vessel wall and uses staples incorporated in the device to penetrate into tissue and secure the bypass graft to the host vessel.

Walsh et al. propose a similar end-side stapling device in U.S. Pat. Nos. 4,657,019, 4,787,386, and 4,917,087. This end-side device has a ring with tissue piercing pins. The bypass graft is everted over the ring; the pins then penetrate the bypass graft thereby securing the bypass graft to the ring. The ring is inserted through a large incision created in the host vessel wall and the tissue piercing pins are used to puncture the host vessel wall. A clip is then used to prevent dislodgment of the ring relative to the host vessel.

End-side stapling devices require insertion through a large incision, which dictates that blood flow through the host vessel must be interrupted during the process. Even though these and other clipping and stapling end-side anastomotic devices have been designed to decrease the time required to create the anastomosis, interruption of blood flow through the host vessel increases the morbidity and mortality of bypass grafting procedures, especially during beating heart CABG procedures. A recent experimental study of the U.S. Surgical ONE-SHOT anastomotic clip applier observed abrupt ventricular fibrillation during four of fourteen internal thoracic artery to left anterior descending artery anastomoses in part due to coronary occlusion times exceeding 90 seconds (Heijmen et al: "A Novel One-Shot Anastomotic Stapler Prototype for Coronary Bypass Grafting on the Beating Heart: Feasibility in the Pig" *J Thorac Cardiovasc Surg.* 117:117–25; 1999).

A need thus exists for bypass grafts and delivery systems that are capable of quickly producing an anastomosis between a bypass graft and a host vessel wall without having to stop or re-route blood flow. These anastomoses must withstand the pressure exerted by the pumping heart and ensure blood does not leak from the anastomoses into the thoracic cavity, abdominal cavity, or other region exterior to the vessel wall.

SUMMARY OF THE INVENTION

This invention provides improvements to the sutureless anastomosis systems that enable a physician to quickly and accurately secure a bypass graft to a host vessel or other tubular body structure. The delivery systems of the invention do not require stopping or re-routing blood flow while producing the anastomosis; current techniques require interrupting blood flow to suture, clip, or staple a bypass graft to the host vessel wall.

The fittings of the invention are intended to secure biological bypass grafts, obtained by harvesting vessels from the patient or another donor patient, or synthetic bypass graft materials to a patient's host vessel. When using harvested vessels, the fitting embodiments must accommodate a variety of harvested vessel sizes and wall thicknesses. When using synthetic bypass graft materials, the fittings may be incorporated in the bypass graft design to eliminate the step of attaching the bypass graft to the fitting prior to deploying the bypass graft and fitting.

One aspect of the invention provides improved fitting embodiments designed to compress into a reduced diameter while attaching the bypass graft to the fitting and/or deploying the fitting through the delivery system. Once deployed, the compressible fittings of the invention expand towards their preformed geometry such that they exert radial force at the vessel attachment sites; this helps maintain the patency of the anastomosis.

Another aspect of the invention provides additional angled fittings designed to produce anastomoses between bypass grafts and host vessels such that the angle between the bypass graft and the host vessel reduces turbulent flow near the anastomosis. The angled fittings may also be designed compressible.

Another aspect of the invention includes improved support devices capable of securing the end-side fitting to the host vessel and providing a smooth transition from the anastomosis site to the body of the bypass graft.

A further aspect of the invention involves deployment sheaths that facilitate removing from around the bypass graft after inserting and securing the end-side fitting. Various deployment sheath embodiments utilize locking mechanisms to maintain pre-split deployment sheaths in a closed orientation. The locking mechanisms facilitate removal with minimal force, which is preferred to current splittable sheaths that require substantial effort to tear the hub, valve, and sheath.

Additional sheathless anastomosis embodiments are disclosed which are designed to insert the petals or securing end of the end-side fitting into the host vessel without having to insert the fitting through a deployment sheath. Additional end-side fitting embodiments that are able to screw through a small opening in the host vessel wall with or without the use of a guidewire are discussed. Other end-side fitting embodiments that are able to advance through a small opening in the host vessel wall with the use of a guidewire or dilator without having to rotate the end-side fitting are also discussed.

Further features and advantages of the inventions will be elaborated in the detailed description and accompanying drawings.

BRIEF DESCRIPTION OF THE DRAWINGS

FIG. 3a shows an end-side fitting embodiment.

FIG. 3b shows a close-up of two alternative petal embodiments used with the end-side fitting of FIG. 3a.

FIG. 3c shows the end-side fitting embodiment of FIG. 3a configured for small or medium sized vessels.

FIG. 5a shows an end-side fitting embodiment having curved petals.

FIGS. 5d and 5e show side views of the end-side fitting bases of FIGS. 5b and 5c positioned along a host vessel wall.

FIG. 8 shows a dilator deployment device.

FIG. 10a shows another small vessel end-side fitting embodiment.

FIG. 11 shows a small vessel end-side fitting embodiment fabricated from a sheet of material preformed into the desired shape.

FIG. 15b shows an alternative screw-in end-side fitting embodiment.

DETAILED DESCRIPTION OF THE INVENTION

Figure 1A:
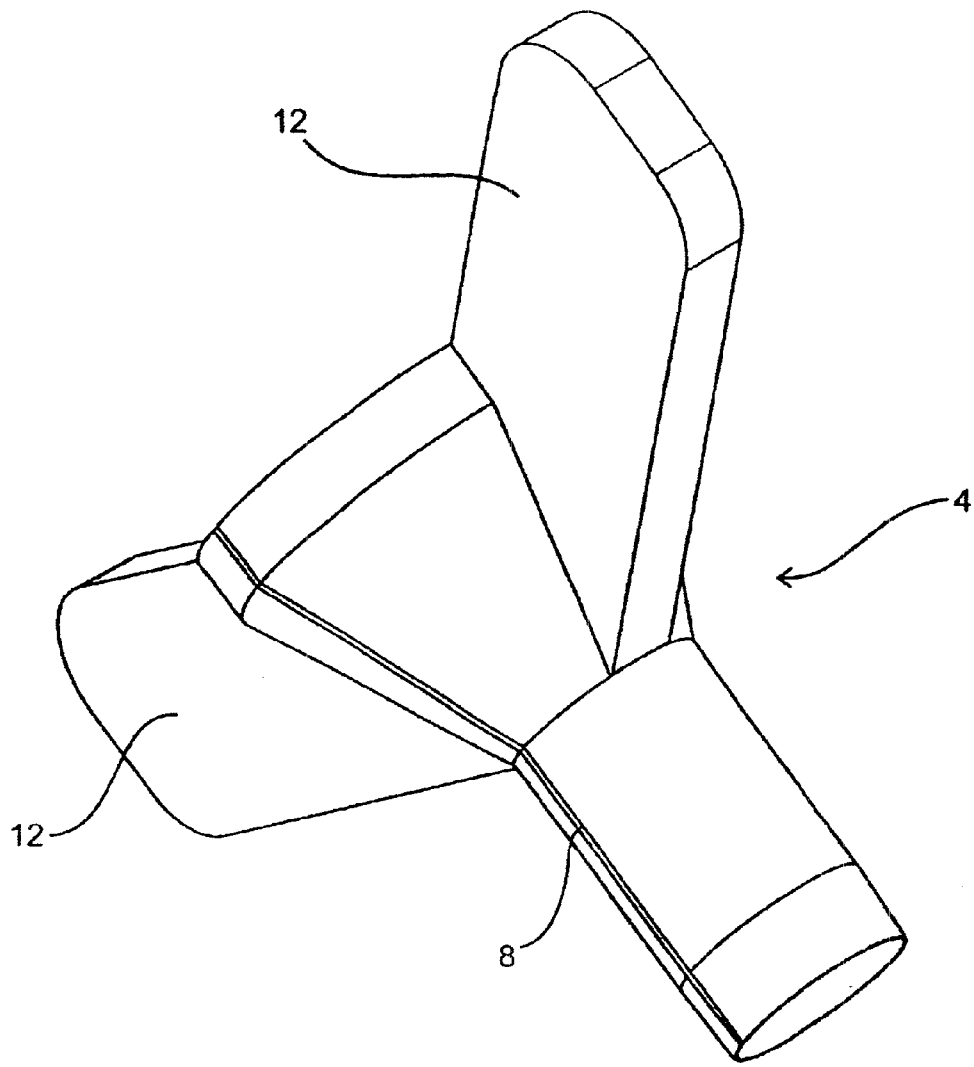
FIG. 1*a* shows a splittable deployment sheath.
Figure 1B:
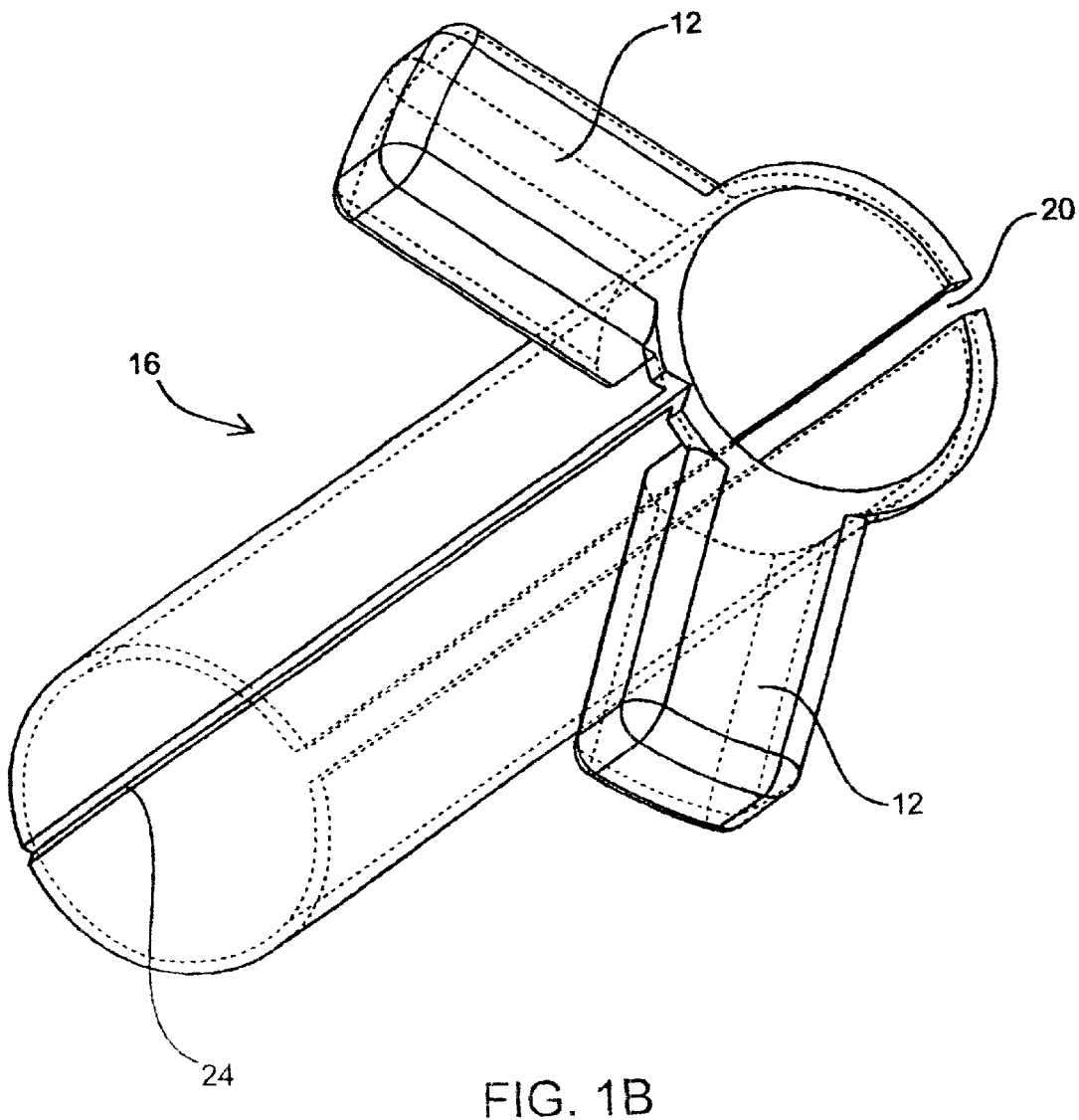
FIG. 1*b* shows a separable loading sheath.

The fittings and deployment systems of the present invention are intended to produce anastomoses between bypass grafts and host vessels to treat vascular abnormalities such as stenoses, thromboses, other occlusions, aneurysms, fistulas, or other indications requiring a bypass graft. The systems of the present invention are also useful in bypassing stented vessels that have restenosed, and saphenous vein bypass grafts that have thrombosed or stenosed. Current approaches for treating stenosed stents have not been successful at safely and reliably removing the lesion and opening the vessel lumen. Therefore, the approach described by this invention, which produces a blood flow conduit around the stented lesion, mitigates concerns associated with damaging the stent or forming emboli while removing deposits attached to the stent. The same argument holds true for saphenous vein grafts that have restenosed or thrombosed.

The embodiments of the invention also provide mechanisms to secure branching vessels to a replacement graft during surgical procedures in which the branching vessels would otherwise be occluded from blood flow (e.g. reattaching the renal arteries, mesenteric artery, celiac artery, and intercostal arteries during treatment of abdominal aortic aneurysms that are pararenal, suprarenal, or thoracoabdominal in classification). The embodiments of the invention also enable reattaching the left main artery and right coronary artery during aortic root replacement procedures.

The inventive fitting and delivery system embodiments discussed herein are directly amenable to robotic surgery and less invasive (i.e. minimally invasive) surgery involving a thoracostomy or mini median sternotomy to access the anastomosis site. In particular, the fittings and delivery system embodiments of the present invention enable automation of the attachment of the bypass graft to the fitting, especially when considering the use of the loading sheath and/or end-side fittings capable of being advanced over a guidewire as described below. In addition, the deployment and securing systems of the invention are significantly easier to automate than conventional suturing.

Bypass Grafts

The bypass graft of the present invention may be a synthetic graft material, harvested vessel, or other tubular body structure, depending on the indication for use. The harvested vessels may be an internal mammary artery, mesenteric artery, radial artery, saphenous vein or other body tubing. Harvested vessels may be dissected using newer minimally invasive, catheter-based techniques or standard surgical approaches. The end-side fittings in accordance with the present invention are designed to attach bypass grafts to host vessels (or other tubular structures). The fittings used to position and attach such bypass grafts are extensions of the collet and grommet embodiments described in U.S. patent application Ser. No. 08/966,003 filed Nov. 7, 1997, and the fittings described in U.S. patent application Ser. No. 09/329,503 filed Jun. 10, 1999, the entirety of each are which incorporated herein by reference. The primary advantage of biological bypass grafts (e.g. harvested vessels) over currently available synthetic materials is the reduction in thrombosis especially when using small diameter (e.g. $\leq 2$ mm) bypass grafts. However, the fittings and delivery systems of the invention are equally effective at positioning and securing all types of bypass grafts, biological and synthetic.

Synthetic bypass grafts may be manufactured by extruding, injection molding, weaving, braiding, or dipping polymers such as PTFE, expanded PTFE, urethane, polyamide, polyimide, nylon, silicone, polyethylene, collagen, polyester, PET, composites of these representative materials, or other suitable graft material. These materials may be fabricated into a sheet or tubing using one or a combination of the stated manufacturing processes. The sides of sheet materials may be bonded using radiofrequency energy, laser welding, ultrasonic welding, thermal bonding, sewing, adhesives, or a combination of these processes to form tubing. The synthetic bypass graft may be coated, deposited, or impregnated with materials such as paralyne, heparin solutions, hydrophilic solutions, thromboresistance substances (e.g., glycoprotein IIb/IIIa inhibitors), antiproliferative substances (e.g., rapamycin), or other substances designed to reduce thrombosis or mitigate other risks that potentially decrease the patency of synthetic bypass grafts. In addition, synthetic bypass grafts may be seeded with endothelial cells, or other biocompatible materials that further make the inner surface of the bypass graft biologically inert.

The primary advantage of synthetic bypass graft materials is the ability to bond the bypass graft to the fittings prior to starting the procedure or to incorporate the fittings into the bypass graft by injection molding, adhesive bonding, or other manufacturing processes. Currently, synthetic bypass grafts are indicated for blood vessels having medium and large diameters (e.g. >3 mm), such as peripheral vessels, tubular structures such as the fallopian tubes, or shunts for hemodialysis. However, medical device manufacturers such as Possis Medical, Inc. and Thoratec Laboratories, Inc. are evaluating synthetic bypass grafts for coronary indications. In this disclosure and the accompanying drawings, reference to bypass graft may pertain to either biological bypass grafts such as harvested vessels or synthetic bypass grafts, unless specifically stated.

As discussed in co-pending U.S. patent application Ser. No. 08/932,566 filed Sep. 19, 1997 and co-pending U.S. patent application Ser. No. 08/966,003 filed Nov. 7, 1997, support members may be incorporated into the graft. When using synthetic grafts, the support members may be laminated between layers of graft material. The synthetic graft encompassing support members may be fabricated by extruding, spraying, injection molding, or dipping a primary layer of graft material over a removable mandrel; positioning, winding or braiding the support members on the primary layer; and extruding, spraying, injection molding, or dipping a secondary layer over the graft material/support member combination. The support members may be fabricated from a metal, alloy (e.g., stainless steel or nickel titanium), or polymer (e.g., nylon or polyester); however, the support members preferably have a shape memory. Support members enhance the performance of the bypass graft by maintaining lumenal patency, offering flexibility, and increasing the strength. Support members fabricated from memory elastic alloys (such as nickel titanium) exhibiting stress-induced martensite characteristics further reinforce the bypass graft and/or vessel wall and prevent permanent deforming upon exposure to external forces. Such support members also permit compressing the bypass graft into a low profile during deployment through the host vessel wall; the support members urge the bypass graft to expand towards its preformed configuration after the constraining means (e.g., delivery system) is removed.

End-Side Fittings

The end-side fittings of the present invention are preferably constructed from a metal (e.g., titanium), alloy (e.g., stainless steel or nickel titanium), thermoplastic (e.g., PTFE), thermoset plastic (e.g., polyethylene terephthalate, or polyester), silicone or combination of the aforementioned materials into a composite structure; other materials may alternatively be used. For example, end-side fittings fabricated from nickel titanium may be clad with expanded PTFE, polyester, PET, or other material that may have a woven or porous surface. The fittings may be coated with materials such as paralyne or other hydrophilic substrates that are biologically inert and reduce the surface friction. To further reduce the surface tension, metallic or metallic alloy fittings may be electropolished. Evidence suggests that electropolishing reduces platelet adhesion because of the smooth surface. Alternatively, the fittings may be coated with heparin, thromboresistance substances (e.g., glycoprotein IIb/IIIa inhibitors), antiproliferative substances (e.g., rapamycin), or other coatings designed to prevent thrombosis, hyperplasia, or platelet congregation around the attachment point between the bypass graft and the host vessel. Alternatively, a material such as platinum, gold, tantalum, tin, tin-indium, zirconium, zirconium alloy, zirconium oxide, zirconium nitrate, phosphatidyl-choline, or other material, may be deposited onto the fitting surface using electroplating, sputtering vacuum evaporation, ion assisted beam deposition, vapor deposition, silver doping, boronation techniques, a salt bath, or other coating process. A still further improvement of the fittings is to include beta or gamma radiation sources on the end-side fittings. A beta or gamma source isotope having an average half-life of approximately 15 days such as Phosphorous 32 or Paladium 103 may be placed on the base and/or petals of the end-side fitting using an ion-implantation process, chemical adhesion process, or other suitable method.

The fittings consist of one or more components designed to secure a bypass graft to the fitting and the fitting to the host vessel wall to produce a fluid tight bond between the bypass graft and the host vessel. The fittings may be used to produce end-side anastomoses for medium and small diameter vessels (e.g., peripheral vessels and coronary vessels) where retrograde blood flow is essential, and end-side anastomoses for large diameter vessels (e.g., the aorta). The fittings and delivery systems described below may be modified to accommodate end—end anastomoses by reducing or eliminating the petals from the design.

Retaining clips may be used to secure the bypass graft to the outer surface of the end-side fitting. The retaining clips may be fabricated from a metal, alloy, thermoplastic material, thermoset, silicone, or composite. The retaining clips preferably permit approximately 30% enlargement in diameter without becoming permanently deformed. One retaining clip embodiment is a preshaped member wound beyond a single turn and having radiused edges and ends. One representative fabrication process for the preshaped retaining clip involves forming the raw material into a desired geometry and exposing the material to sufficient thermal energy to anneal the material into this predetermined shape. This process applies to metals, alloys (e.g., nickel titanium) as well as polymers and other materials. The preshaped retaining clip configuration is expanded, thereby enlarging the diameter of the retaining clip. Once the retaining clip is positioned, the force causing the retaining clip to enlarge is removed, causing the retaining clip to return towards its preformed shape and thereby compressing the bypass graft against the fitting. Another retaining clip embodiment is shown in FIG. 18c. This retaining clip has two radial wires extending just beyond one half of a turn and separated by a curved link. As will be discussed later, this retaining clip may also be used to secure the support device to the end-side fitting.

Figure 6A:
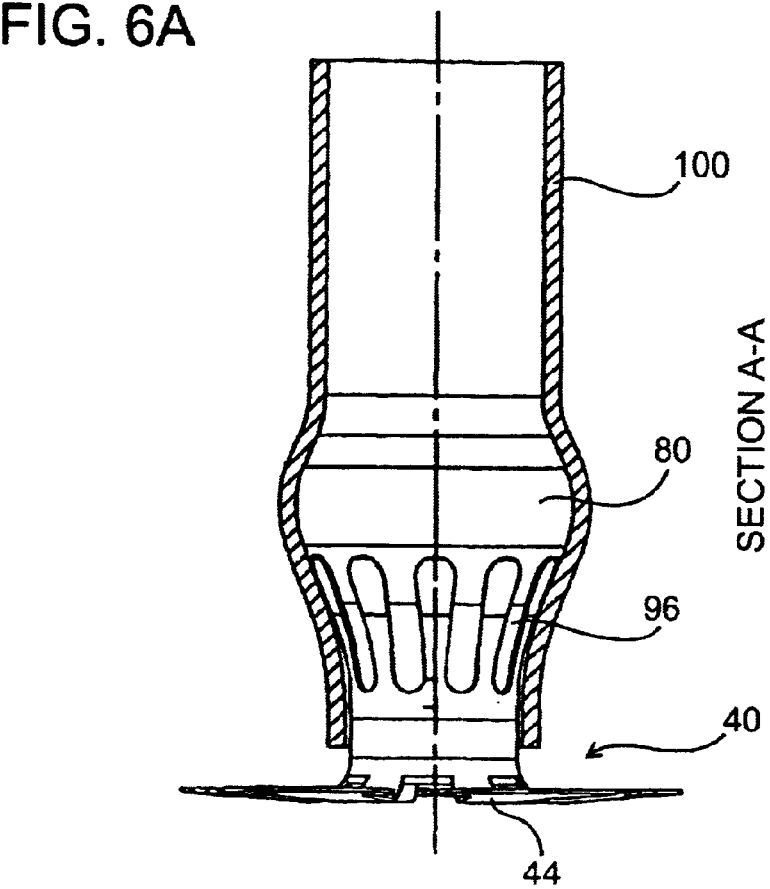
FIGS. 6a and 6b show an end-side fitting embodiment that is able to accommodate a range of bypass graft inner diameters.
Figure 6B:
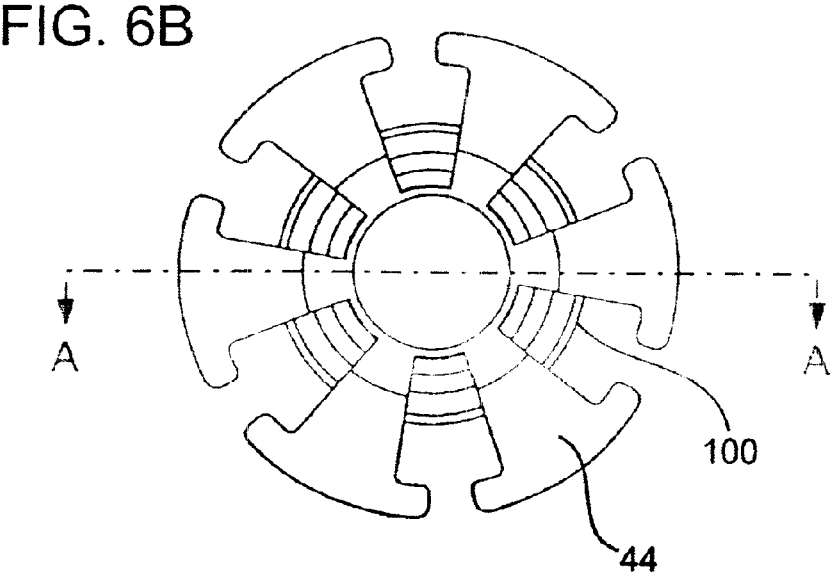

One embodiment of the invention involves attaching the bypass graft around the exterior of the base or stem of the fitting. The bypass graft is secured around the base of fitting using retaining clips as described above. The bypass graft is first advanced over the exterior of the fitting and is secured with a retaining clip, suture, implantable clips, or staples. The base of the fitting and/or the retaining clip may contain tabs or other securing structures designed to lock the bypass graft to the base of the fitting. The base of the fitting may alternatively incorporate radial extensions 96 to further lock the bypass graft to the fitting base, as shown in FIGS. 6a and 6b. A retaining ring may or may not be used with this end-side fitting embodiment. Alternatively, notches may be fabricated in the base of the fitting and adapted to accept the retaining clip. The notches reinforce the compression fit between the bypass graft and the base of the fitting by positioning retaining clips in the indents defined by the notches. The base of the fitting and the retaining clip may alternatively be configured to match, once deployed, especially when the fitting and retaining clip are expandable/compressible. The base of the compressible fitting defines spaces 92 (shown in FIGS. 4a and 4c); the retaining clip may be designed to position extensions of the retaining clip (matching those of the fitting) within these spaces 92, further locking the retaining clip to the fitting and enhancing the bond between the bypass graft and the fitting.

Figure 4A:
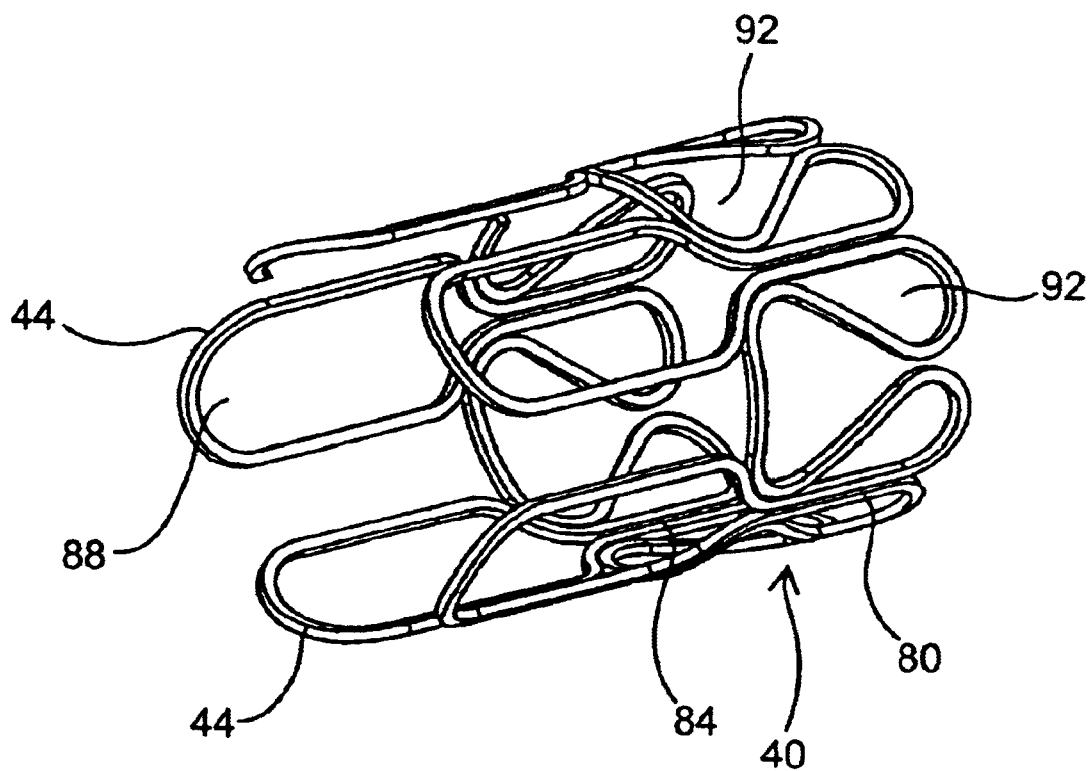
FIGS. 4a to 4c show split-wall end-side fitting embodiments having compressible/expandable stems.
Figure 4B:
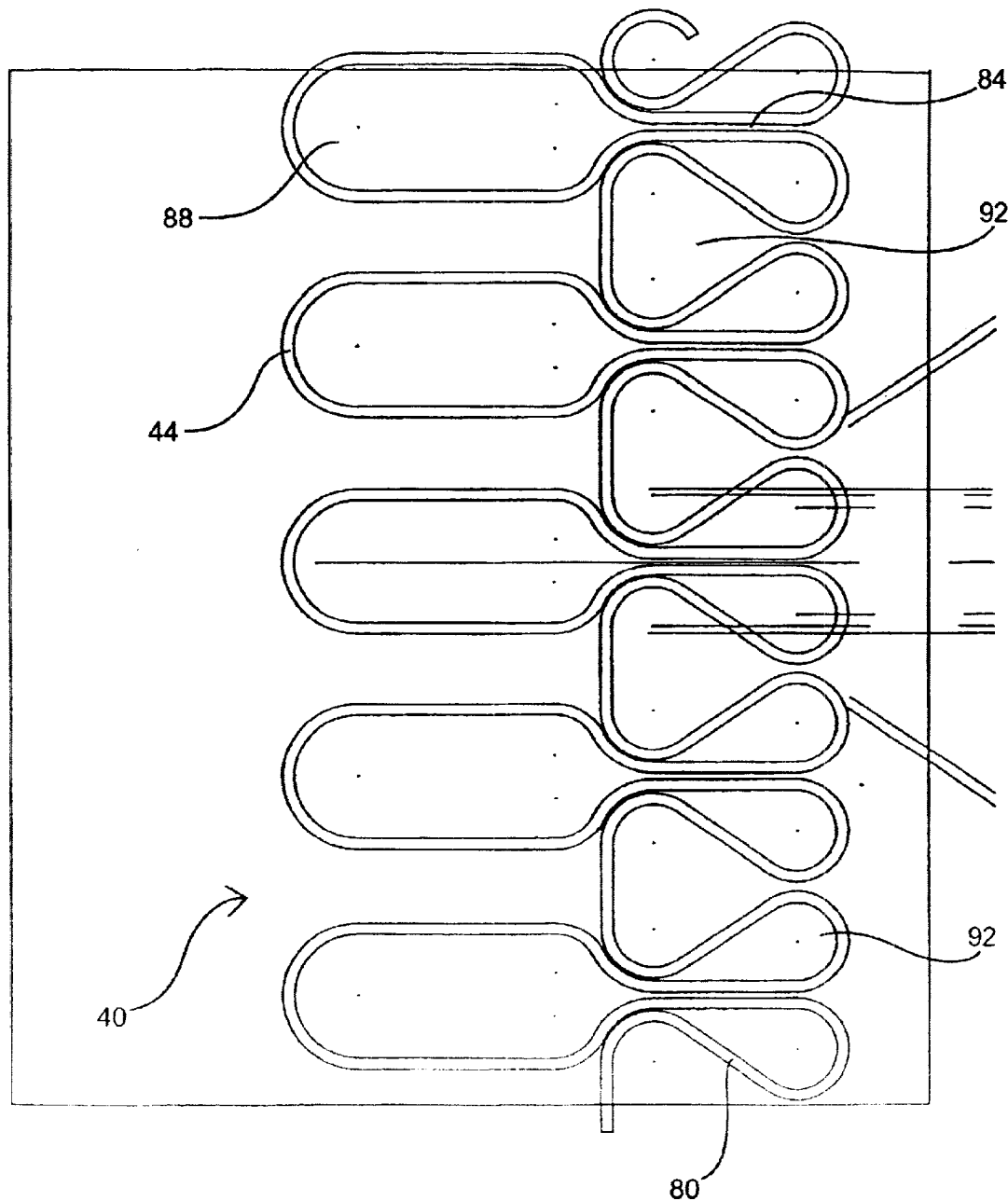
Figure 4C:
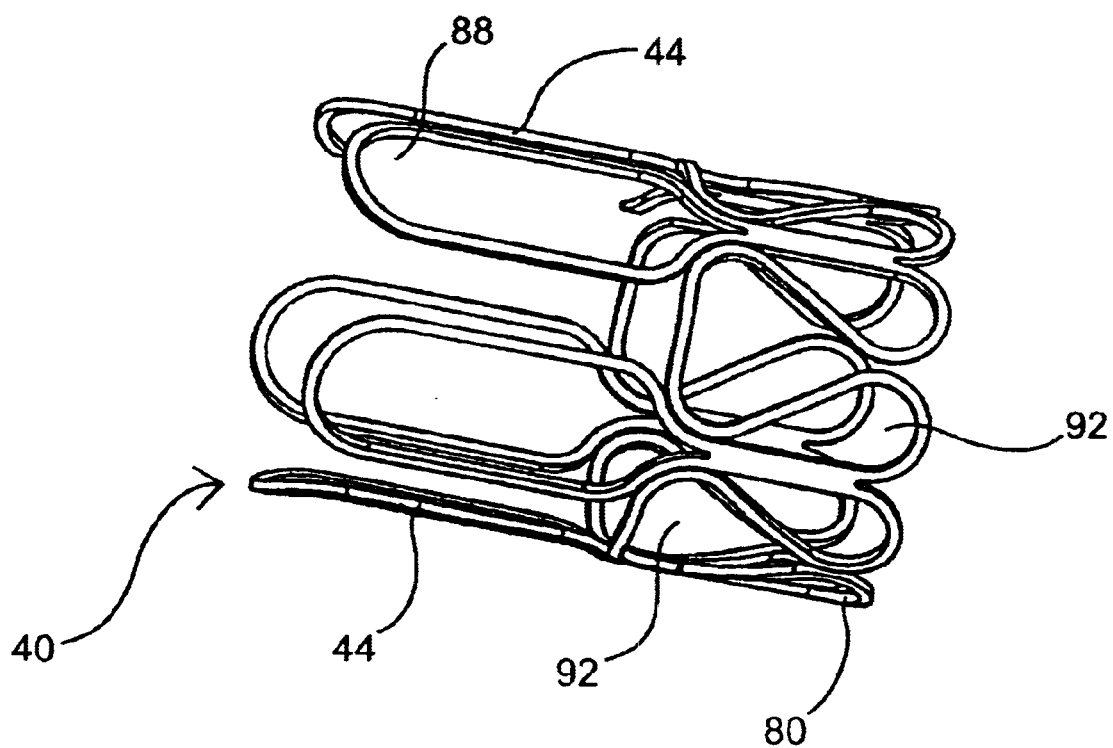

End-side fitting embodiments, shown for example in FIGS. 4a to 4c and in FIG. 11, may be fabricated from a sheet of material cut into the desired pattern and thermally formed into the desired cross-sectional geometry (circular, elliptical, or other shape). The sides of the fitting may be bonded to form an enclosed tube or may be formed with a gap between opposite sides to enable compressing the fitting into a reduced diameter for positioning the bypass graft over the base of the fitting and inserting the fitting through a delivery system having a diameter less than the expanded diameter of the fitting. Such compressible fittings also facilitate sizing issues since they accommodate a wide range of bypass graft sizes.

To produce these end-side fittings, sheet stock may be fabricated into the desired pattern by chemical etching, electrical discharge machining (EDM), laser drilling, or other manufacturing process. The end-side fitting is then wrapped around a mandrel having the desired resting cross-sectional profile and the end-side fitting is heated until it assumes this configuration. If the sides are to be bonded, spot welding, laser welding, or other manufacturing process may be employed. Alternatively, the fitting may be fabricated from a tubular metal material having the desired cross-sectional geometry, using chemical etching, EDM, laser drilling, or other manufacturing process to form the desired pattern. Again, the fitting may be formed into a complete tube or may incorporate a gap between opposite sides to make the fitting compressible. When forming the resting configuration of the compressible, split-wall end-side fitting, a gap is produced between opposite sides. The gap between the sides of the fitting permits compressing the end-side fitting into a reduced diameter. This facilitates positioning the bypass graft over the base of the fitting and/or advancing the fitting through a delivery system having an inner diameter less than the outer diameter of the fitting in its expanded, resting configuration. In addition, this helps size a single fitting configuration to accommodate a wide range of bypass graft sizes.

The split end-side fitting embodiments, as shown in FIGS. 4a and 4b, may be designed with improved compressibility and expandability due to the geometry of the base or stem 80. As opposed to solely relying on the width of the gap and the ability of the sides of the fitting base to spiral into a compressed diameter, as is the case for a solid base, the spaces 92 in the base 80 are configured to permit additional enlarging or compressing of the base using an external force.

The expandable/compressible end-side fitting may be expanded into an enlarged diameter so the base of the fitting may be placed over a bypass graft everted or positioned over a central member. When the external force expanding the fitting is removed, the end-side fitting compresses the bypass graft against the central member, thus securing the bypass graft to the fitting. In addition, the base of the fitting (as well as the petals if desired) may be covered with a fluid-tight, compliant material such as silicone, urethane, or other material. The covering over the base of the fitting may be formed by dipping, injection molding, or other suitable manufacturing process. This covering enables the base of the fitting to compress and expand while maintaining the leak resistance of the anastomosis and isolating the cut end of the bypass graft from blood.

Figure 24A:
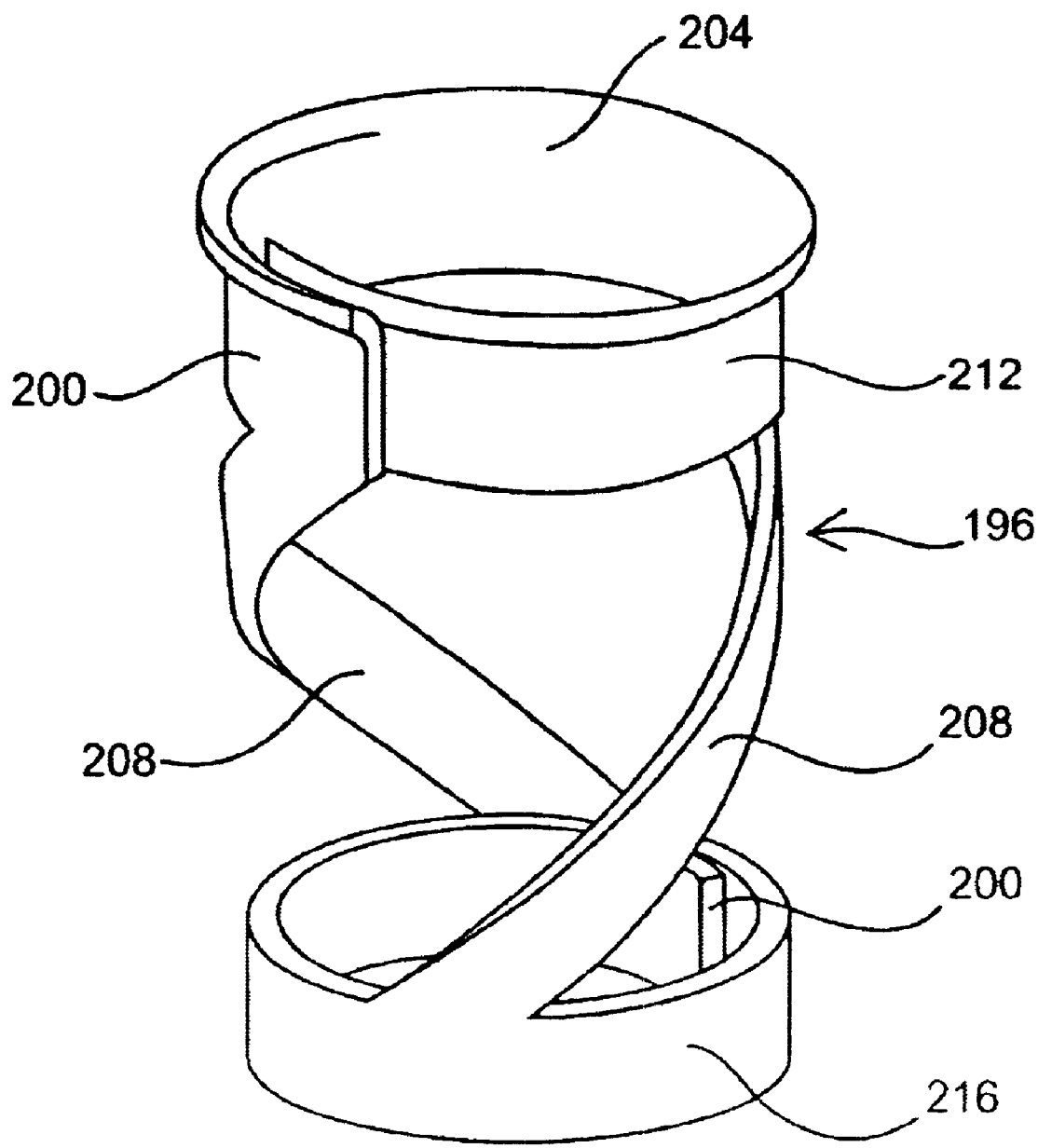
FIGS. 24a to 24b show a flared, compressible inner piece used to secure the cut distal end of a bypass graft within an end-side fitting and isolate the cut end from blood flow.
Figure 24B:
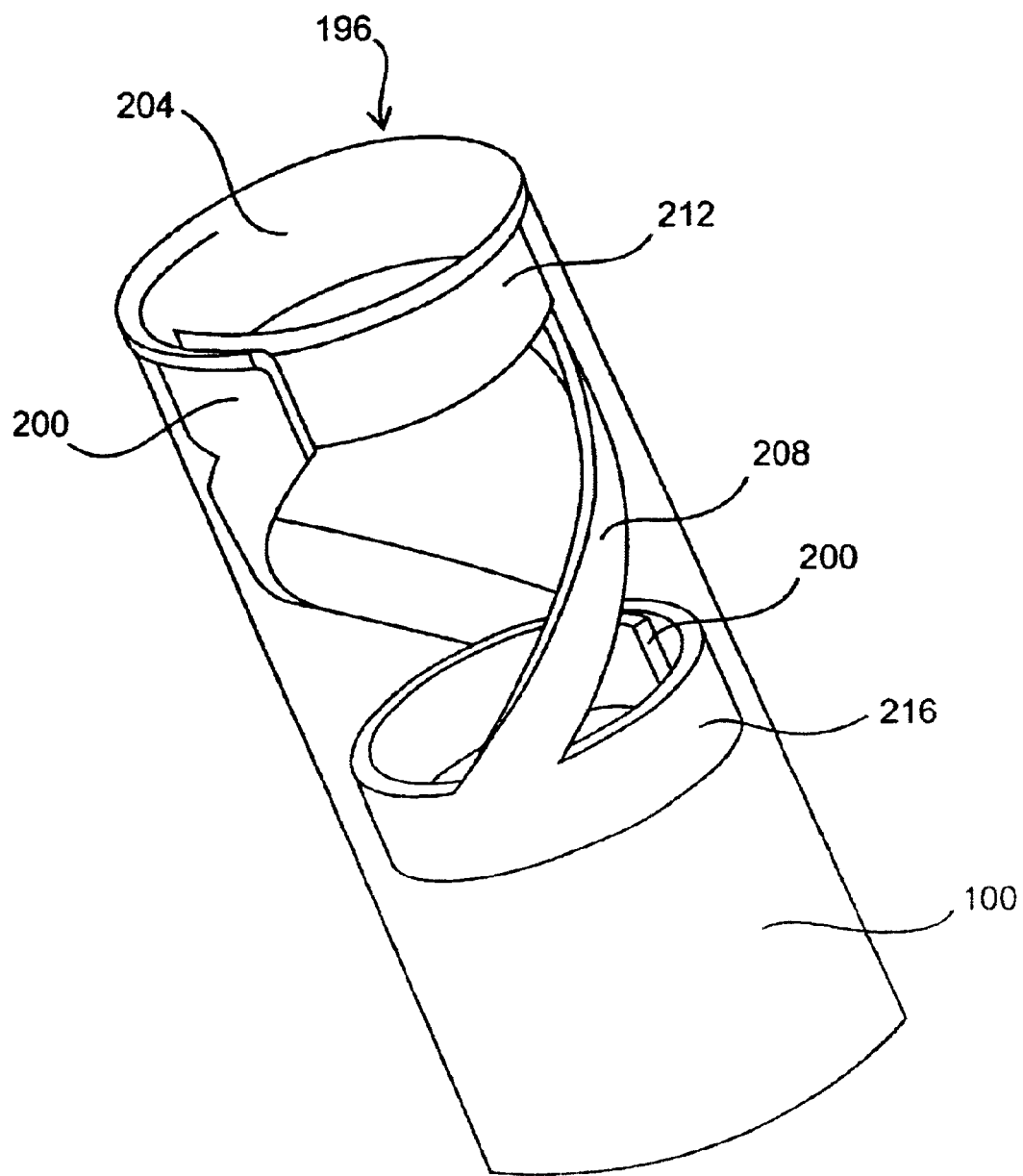

In addition to or instead of making the base of the end-side fitting expandable/compressible, the central member may be fabricated so it can be compressed into a reduced outer diameter for insertion into the end-side fitting. The central member 196 shown in FIG. 24a has a distal split ring 212 and proximal split ring 216 containing an overlap 200 between opposite sides. The split rings 212 and 216 are connected with at least one curved link 208. Two such links 208 are shown in FIG. 24a separated by spaces. For applications in which the bypass graft is not everted around the central member 196, as shown in FIG. 24b, this central member minimizes the total surface area of blood contacting material by creating large spaces throughout the central member where the endothelium of the biological bypass graft is exposed to blood flow.

To compress the central member 196, opposite sides are spiraled inward thereby causing the outer diameter to decrease. At this point, the central member may be inserted into a bypass graft already contained in an end-side fitting and abutting the distal end of the fitting. After positioning the central member, the external force causing the central member to compress is removed, causing the central member to urge the biological bypass graft against the end-side fitting. For everted scenarios, the central member may be compressed to evert the bypass graft after inserting the biological bypass graft through the lumen of the central member; the central member is constrained in a reduced diameter configuration while the bypass graft is everted. Once everted, the external force causing the central member to compress into a reduced diameter is removed allowing the central member to return towards its preformed shape. The central member and everted bypass graft may be positioned within the end-side fitting with or without the central member (and everted bypass graft) compressed into a reduced diameter configuration. Alternatively, an expandable end-side fitting may be enlarged in diameter for positioning over the central member and everted bypass graft.

For situations in which the biological bypass graft is not everted, the cut end of the bypass graft should preferably be isolated from blood flow because of the inherent thrombogenicity of substances secreted through severed ends of cut vessels and the vessel epithelium. Therefore, the distal ring 212 of the central member 196 (shown in FIG. 24a) may also contain a flared distal end 204 that contacts the distal end of the end-side fitting, once positioned, and isolates the cut end of a biological bypass graft that is not everted, as shown in FIG. 24b.

The petals in many of these fitting embodiments are shown straight (i.e. at an angle of zero degrees from the base of the fitting). During manufacture, the petals may be thermally formed such that the petals contact the interior surface of the host vessel once the fitting is inserted through the host vessel wall. The petals, having an angle generally between about 20 and 170 degrees from the base of the fitting in their resting orientation, more preferably between about 30 and 150 degrees, also compress into a reduced outer diameter configuration during deployment through delivery system and expand towards their resting configuration once deployed inside the host vessel. The number of petals incorporated in the end-side fitting design depends on the size of the bypass graft and the size of the host vessel. In the exemplary embodiment shown in FIG. 3a, eight petals 44 are used, although the number of petals can vary significantly (e.g., as little as one or two to as many as sixteen or more) and still be within the scope of the present invention. After advancing the fitting through the deployment sheath and past the host vessel wall, the fitting is advanced beyond the end of the deployment sheath, no longer constrained by the deployment sheath confines, thus allowing the fitting to expand towards its resting configuration. The bypass graft and fitting combination is then gently retracted to engage the interior vessel wall with the petals 44. For mechanical securing, a support device (not shown) is advanced over and locked to the fitting thereby compressing the vessel wall against the petals 44.

The thickness, length, geometry, and width of the petals determine their spring characteristic and stiffness. Extremely stiff petals 44 hinder advancing the end-side fitting through long deployment sheaths. To address this, a number of solutions can facilitate deployment of the end-side fitting. For instance, FIGS. 3a and 3b show slots 84 and holes 88 that may be incorporated in the petals 44 to tailor their stiffness throughout the petal length. The thickness (T) and/or width (W) may be tapered from the base of the fitting and extending distally along the petals, as shown in FIG. 3a, to vary the stiffness profile of the petals. As shown in FIGS. 4a and 4c, the petals 44 may be fabricated with distal ends having a radius so the petals do not catch onto the interior surface of the deployment sheath, which could resist forward motion. As shown in FIGS. 3b and 3c, the petals may incorporate relief cuts (220 or 224) so the petals 44 are able to extend from the base 80 of the fitting with a desired radius of curvature. This is preferred if the maximum strain experienced by the petal upon deflection is to be below the safe limit for the particular petal material used while at the same time maintaining hemostasis between the base 80 of the end-side fitting 40 and the host vessel wall 1. As shown in FIG. 5a, the petals 44 may be formed into arcs extending from the base 80; these petals may also be tapered in width (W) and/or thickness (T) and include distal ends 45 having a radius of curvature. Arc petals 44 shown in FIG. 5a have a higher surface area than non-arced petals while minimizing their overall diameter when extended. As shown in FIG. 1a to 1f, and as described below, the deployment system may be modified so the end-side fitting needs only to be advanced a short distance to extend the petals 44 from within the confines of the deployment sheath.

Figure 5B:
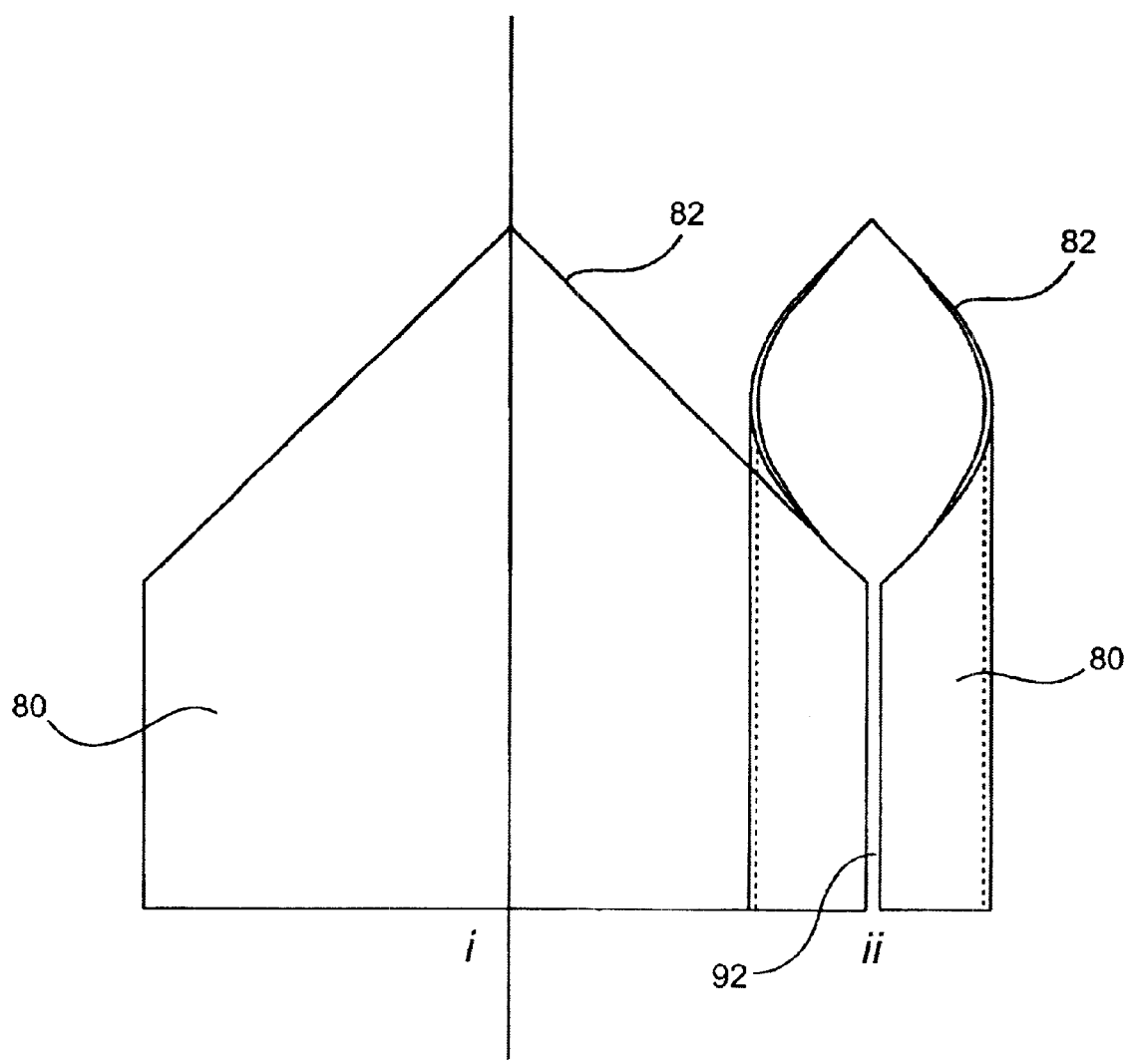
FIG. 5b shows a side view overlapped with a flattened profile of the base of an angled end-side fitting embodiment with a straight or triangular junction from the base to the petals.
Figure 5C:
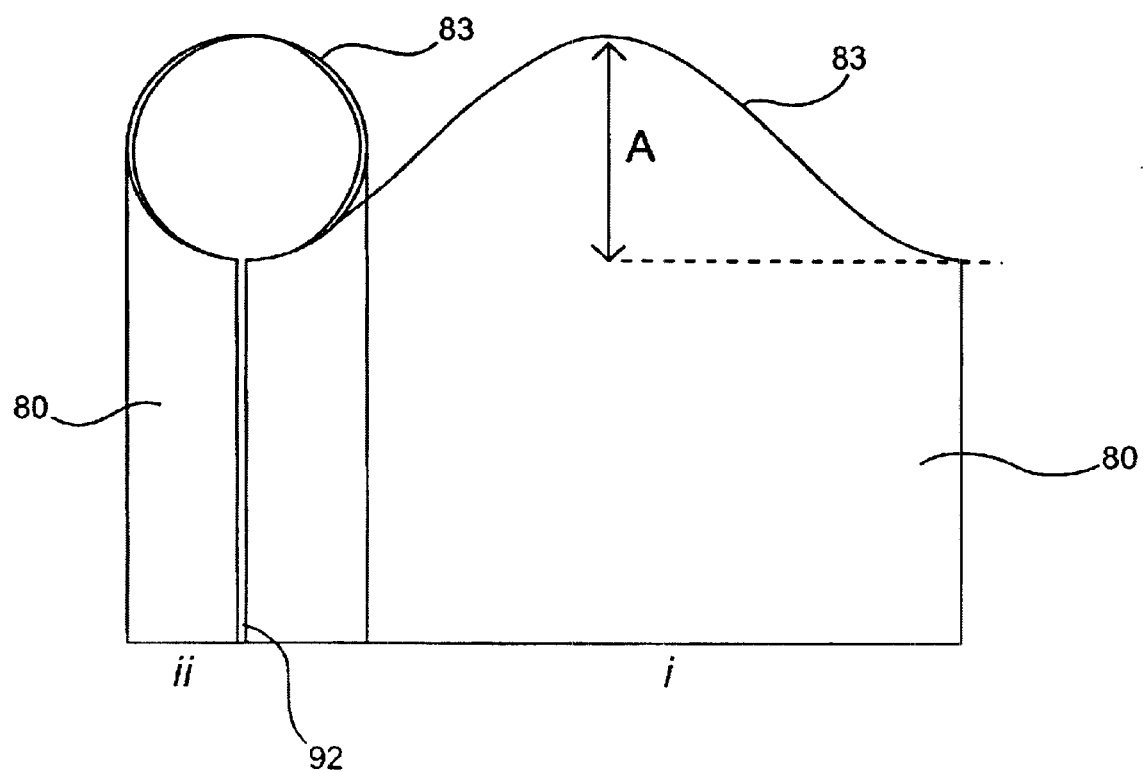
FIG. 5c shows a side view overlapped with a flattened profile of the base of an angled end-side fitting embodiment with a curved or sinusoidal junction from the base to the petals.

The base of the end-side fitting may be improved to maximize the contact between the petals and the interior surface of the host vessel wall and minimize blood leakage around the base of the fitting, especially when fabricating the end-side fitting to produce an angle between the base and the host vessel. FIG. 5b shows the base 80 of an angled fitting in which the junction 82 between the base and the fitting is formed as a triangle when the fitting is viewed in a flattened orientation. As shown in FIG. 5d, the base 80 of this fitting embodiment protrudes into the host vessel wall 1 with a sharp distal tip 85 and forms a gap 86 between the base of the fitting and the host vessel wall at the fitting proximal end. This mismatch in contact between the junction 82 and the host vessel wall 1 produces gaps for blood to leak and hinders positioning the petals into intimate contact with the interior surface of the vessel wall. As FIGS. 5c and 5e show, curving the junction 83 to form a sinusoid or similar curved profile, as viewed in the flattened orientation, produces a substantially better match between the base 80 of the fitting and the host vessel wall 1. This mitigates the potential for blood leakage at the interface between the fitting base 80 and the host vessel wall 1 and improves contact between the fitting petals and the interior surface of the host vessel wall 1. As shown in FIG. 5c and 5e, the curvature defining the junction 83 between the base and the petals for the flattened end-side fitting may be related to the angle ($\alpha$) between the base of the fitting and the host vessel, and the diameter (d) of the end-side fitting base 80 by the following equation:

$$\frac{A}{2} \text{SIN}\left[2\pi \frac{x}{\pi d} - \frac{\pi}{2}\right]$$

where $A = \dfrac{d}{\text{TAN}(\alpha)}$ and $x = 0 \rightarrow \pi d$.

Other equations defining the curvatures of the flattened junctions may be utilized; however, this equation accurately depicts a junction between an end-side fitting base and a host vessel when the diameter of the base is less than the diameter of the host vessel such that the host vessel surface approaches a relatively flat surface. Other curvatures may be incorporated for instances where the diameter of the end-side fitting base matches or is larger than the diameter of the host vessel. As discussed in co-pending U.S. Provisional Application Serial No. 60/151,863 and co-pending U.S. application Ser. No. 09/329,503, the base of the end-side fitting may be fabricated with an elliptical junction or junction having another geometry to transition the base of the end-side fitting into a host vessel having an equal or smaller diameter. Alternatively, the sides of the junction may be formed with wings (not shown) that extend axially or radially and better match the opening through a host vessel having a matching or smaller diameter.

Figure 5F:
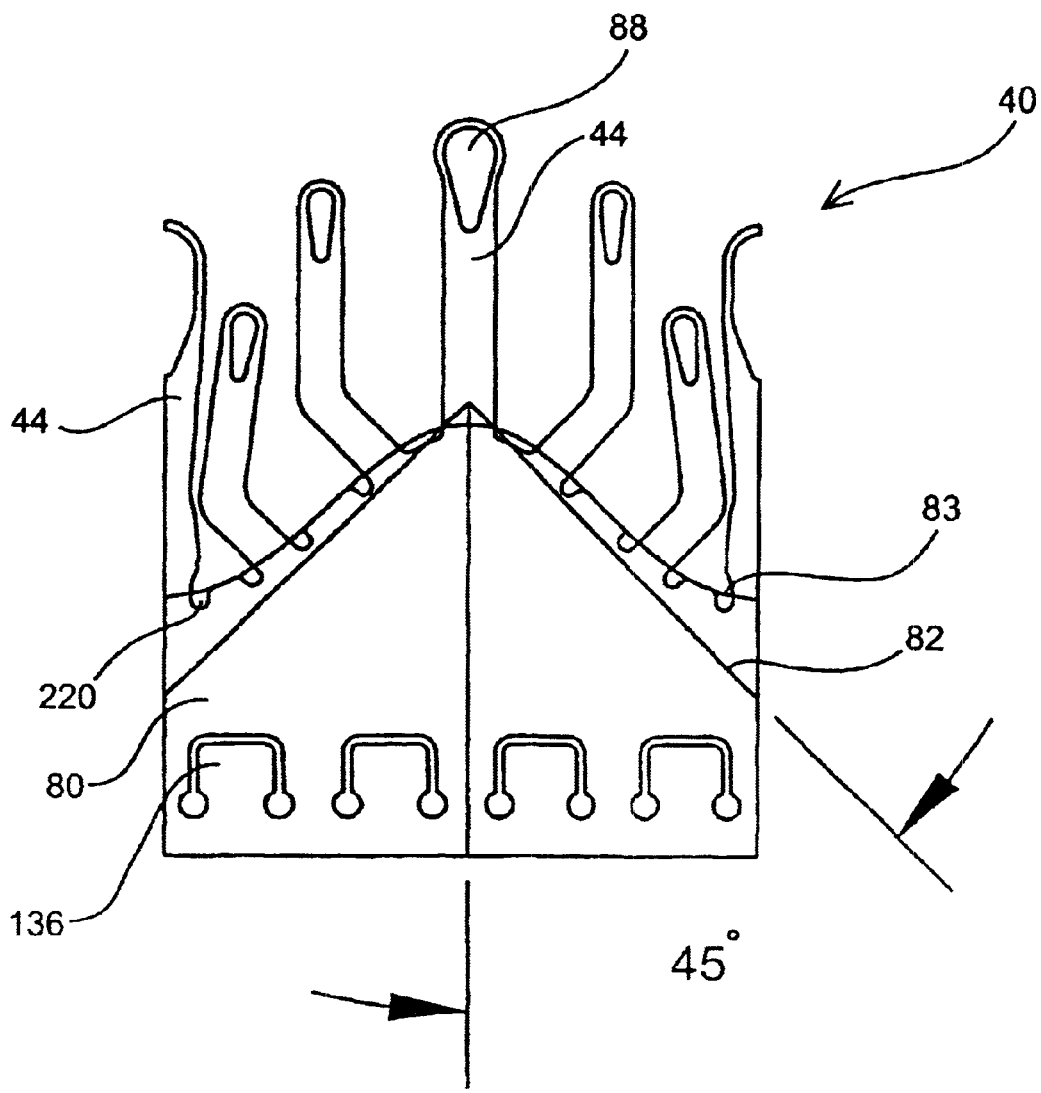
FIG. 5f shows a flattened view of an end-side fitting embodiment having a curved junction between the base to the petals.

FIG. 5f shows an angled end-side fitting formed with the junction 83 between the base 80 and the petals 44 forming a sinusoid or similar curved geometry in the flattened orientation. For comparison purposes, a triangular junction profile 82 is shows to differentiate between the areas where gaps or points would be created if a triangular junction 82 were used. The illustrated angled end-side fitting is configured to produce a 45-degree angle between the base of the fitting and the host vessel; other angles may alternatively be produced. The illustrated angled end-side fitting incorporates petal relief cuts 220, tabs 136, holes 88 in the petals, and may incorporate other features. The sinusoidal or otherwise curved junction 83 may be fabricated into the end-side fitting while forming petals in a flat sheet of material or tubular material used to create the fitting. Flat materials are then thermally or plastically formed into the desired geometry as described above. Also as previously described, end-side fittings formed from flat sheets may have the base bonded in an enclosed tube or incorporate a slot between edges, thereby incorporating an expandable and collapsible characteristic in the base of the fitting.

Figure 22A:
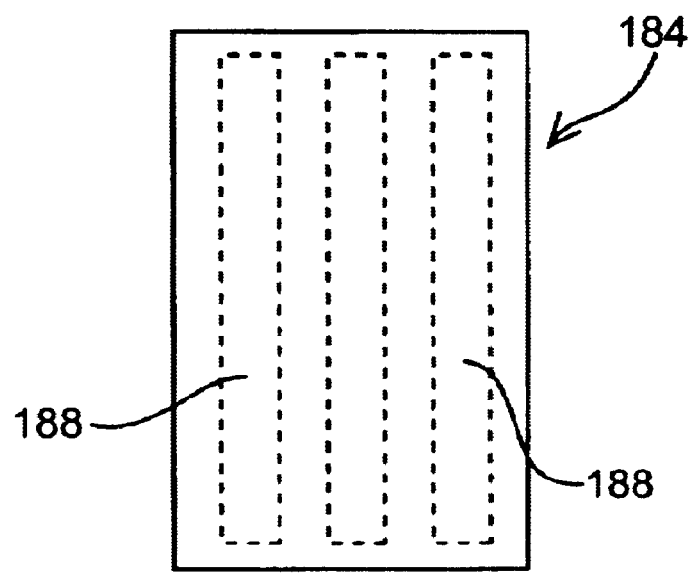
FIGS. 22a to 22d show an everting end-side fitting that does not require a separate component to secure the bypass graft.
Figure 22B:
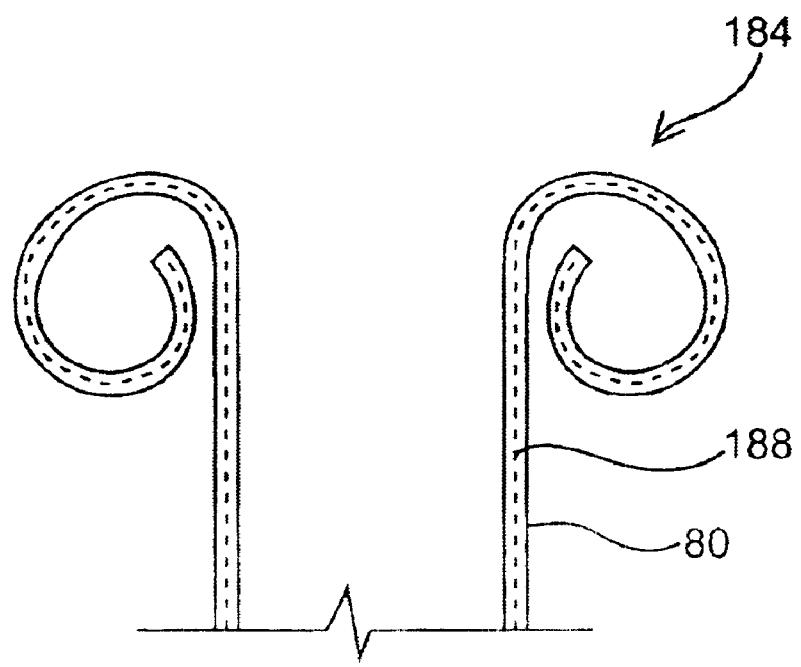
Figure 22C:
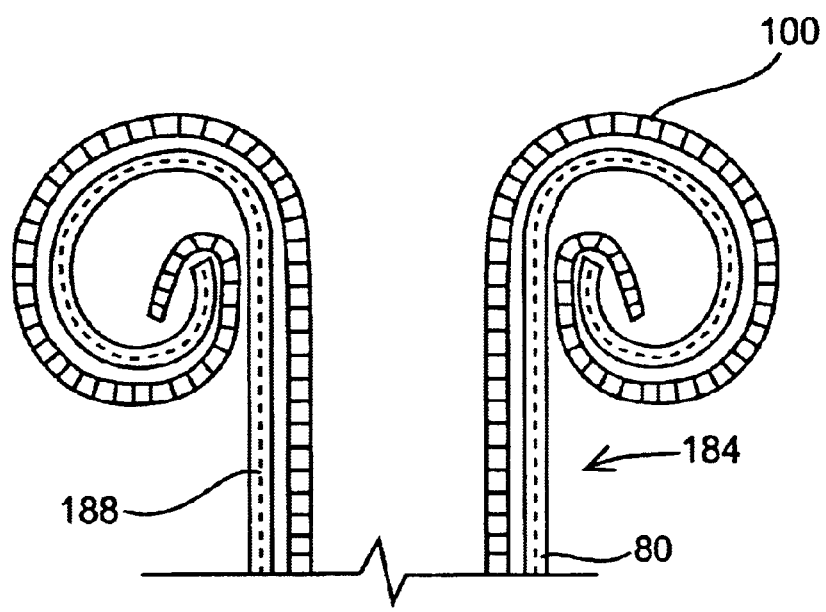
Figure 22D:
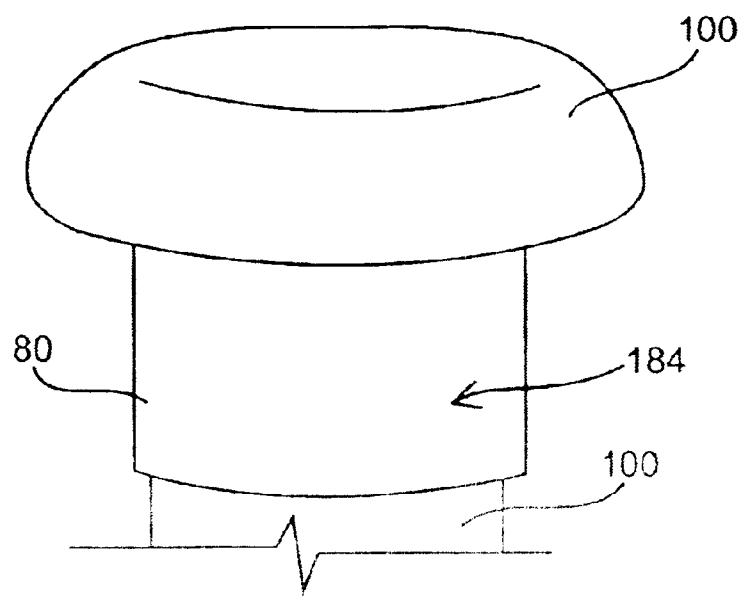

FIGS. 22a to 22d show an alternative embodiment for an end-side fitting 184. This end-side fitting 184 is formed from a compliant material with support members 188 having a memory elastic characteristic. The support members 188 are shaped to form the end-side fitting into the geometry shown in FIG. 22b. This end-side fitting 184 automatically secures the bypass graft to the fitting without the need for a separate central member or retaining ring. The end-side fitting 184 is shown straightened in FIG. 22a. The bypass graft 100 is inserted through the lumen of the straightened end-side fitting 184 and is wrapped around the distal end of the fitting. The force causing the end-side fitting to straighten is removed, enabling the end-side fitting to return towards its predetermined configuration and causing the bypass graft to evert around the end-side fitting and become secured to the fitting as shown in FIGS. 22c and 22d. Once secured, the end-side fitting may be compressed into a reduced diameter and inserted through the deployment system described below. The everted distal end functions as petals and produces a structure to prevent pulling the end-side fitting from the opening through the host vessel wall. As will be described later, a support device may be advanced over and secured to the base 80 of the end-side fitting 184 to secure the fitting to the host vessel wall.

Figure 23A:
FIGS. 23a to 23e show the components and operation of another everting end-side fitting embodiment.
Figure 23B:
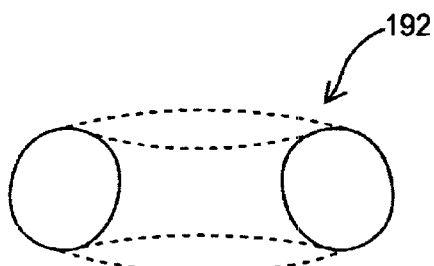
Figure 23C:
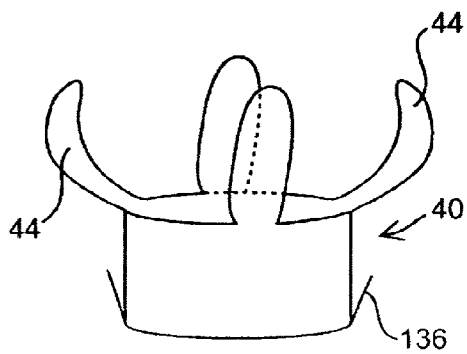
Figure 23D:
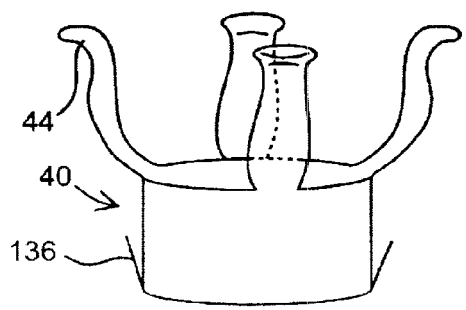
Figure 23E:
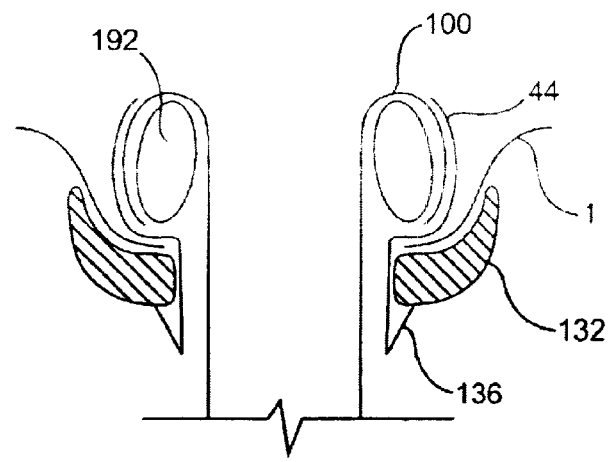

Another embodiment to evert bypass grafts and produce end-side anastomoses is shown in FIGS. 23a to 23e. This device is utilized when the bypass graft is first everted around a central member 192 (shown in FIGS. 23a and 23b). Next, an end-side fitting 40 (shown in FIGS. 23c and 23d) is advanced over the central member and locks the central member with everted bypass graft to the end-side fitting. The central member 192 becomes attached to the end-side fitting 40 by placing it within the petals 44 of the end-side fitting that form a curved preformed geometry adapted to extend partially around the central member thereby locking it in place. The petals 44 may extend partially around the central member or may be further shaped to also extend radially, as shown in FIG. 23d, and provide even more of a surface to contact the interior of the host vessel wall. Once positioned through the host vessel wall 1, as shown in FIG. 23e, a support device 132 (matching that of the end-side fitting geometry) is locked to the base 80 of the fitting using tabs 136. This compresses the host vessel wall between the petals 44 (and central member) and the support device 132.

The fittings in accordance with this invention may be used in any combination to secure bypass grafts at discrete host vessel locations. In addition, synthetic and biological bypass grafts may also be used in any combination with the graft fittings to produce fluid flow passages around vascular abnormalities during a particular procedure.

Support Devices

After positioning the end-side fitting inside the vessel such that the base of the fitting extends through the opening into the host vessel wall and the petals contact the interior surface of the host vessel, the support device is positioned over the base of the fitting and locked in place. The end-side fittings may incorporate tabs 136 (as shown for example in FIGS. 14f and 23c–23e), threads (not shown), or other locking mechanism with which to secure a support device 132 to the end-side fitting. Tabs 136 are preformed so they protrude radially from the base of the fitting to provide a mechanism to secure the support device, once positioned distal to the tabs. The tabs are also preferably fabricated from a memory elastic material to incorporate a spring characteristic permitting the tabs to be compressed into a reduced diameter during deployment. Of course, the tabs do not need to be fabricated from memory elastic materials in the case when they do not need to be compressed into a reduced diameter during introduction. The tabs in the illustrated embodiment are compressed to facilitate inserting the base of the fitting through the delivery system and expand towards their preformed configuration once the fitting is positioned and the external force compressing the tabs is removed. The tabs are fabricated by creating the desired pattern in the fitting material by laser drilling, chemical etching, EDM, or other manufacturing process, whether fitting is fabricated as a sheet or tube. Alternatively, tabs may be fabricated as a separate component and bonded to the fitting by spot welding, laser welding or other suitable manufacturing process.

The support device is alternatively locked to the base of the fitting using adhesives, implantable clips, staples, sutures, or other attachment means. The support device of the illustrated embodiment incorporates an outer compliant covering designed to produce a blood-tight seal and prevent damaging the vessel wall by excess compression. The support device also incorporates an encapsulated central memory elastic core used to maintain the position of the support device relative to the vessel wall and prevent permanent deformation of the support device when expanded into an enlarged diameter for positioning around the base of the fitting. The support device is preferably fabricated as a coil with approximately 1 turn. This support device produces a side-opening upon expansion, which permits advancing the support device over the side of the end-side fitting base or the side of the bypass graft. This eliminates the need to preload the support device over the bypass graft. The expandable/compressible support device is also capable of producing a secure, blood tight interface between host vessel walls and the petals of end-side fittings having a compressible/expandable base for tailoring the outer diameter of the base to match the size of the bypass graft.

The support device may alternatively be constructed from polymers such as polypolyethylene, polycarbonate, PEEK, silicone, nickel titanium, spring stainless steel, other alloy, combination of the aforementioned materials, or other material that may be extruded, injection molded, rolled, or otherwise formed into a tube having the desired cross-sectional profile. In addition, the support device may incorporate a braided, woven, or wound layer laminated between two polymer layers to resist kinking and improve the column strength and torque response. Alternatively, the support device may be fabricated with a memory elastic central layer encapsulated with a compliant covering. The support device preferably has porosity sufficient to permit air to diffuse into tissue covered by the support device. The pore size may be as high as approximately 100 $\mu$m as long as the porosity is chosen such that blood does not continually leak through the support device. If the pore size is chosen such that it completely restricts blood flow even when the porosity is extremely high then the pore size needs to be less than approximately 8 $\mu$m.

Figure 16:
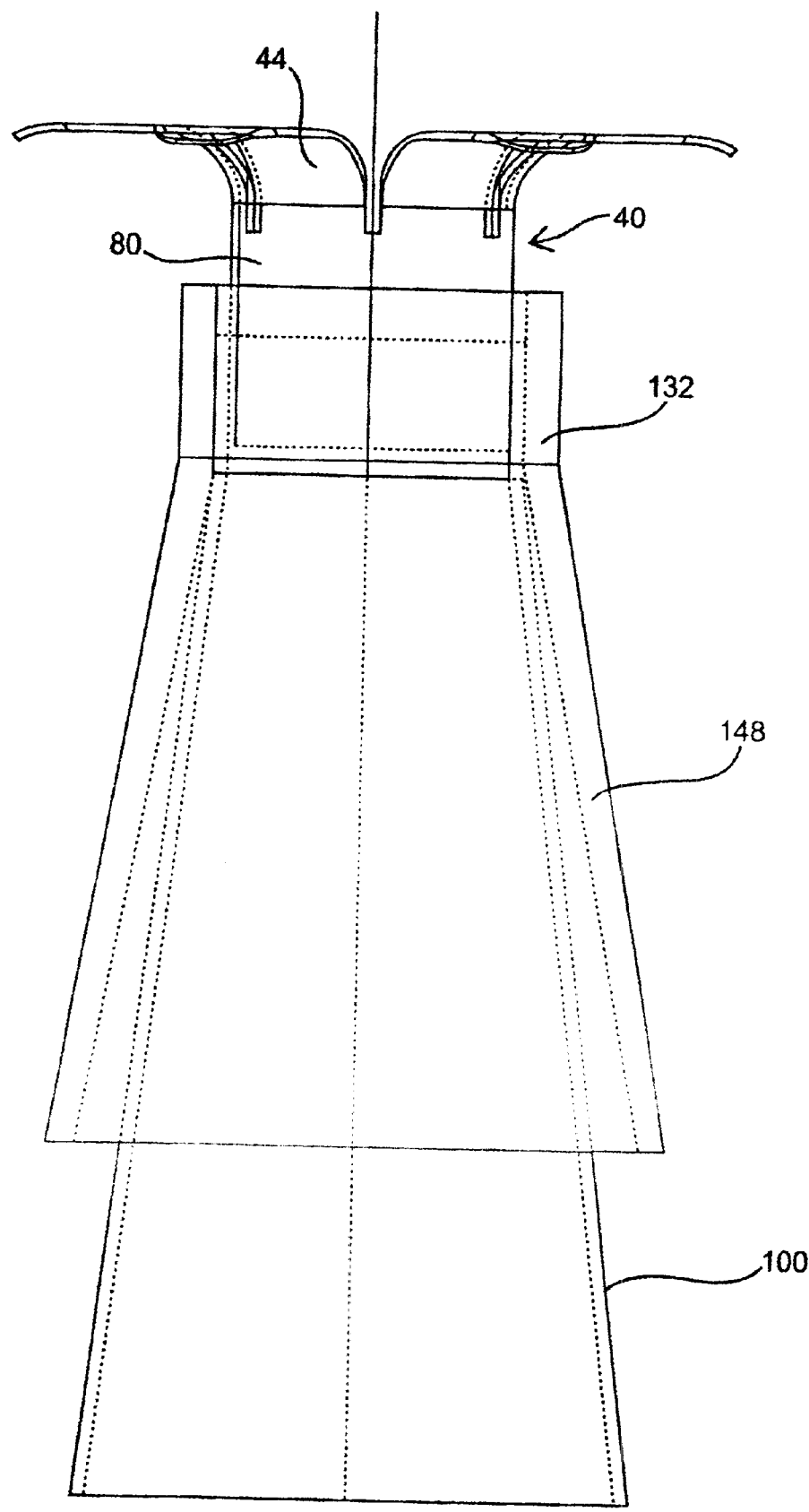
FIG. 16 shows an end-side fitting with a support device having a funneled proximal end.
Figure 17A:
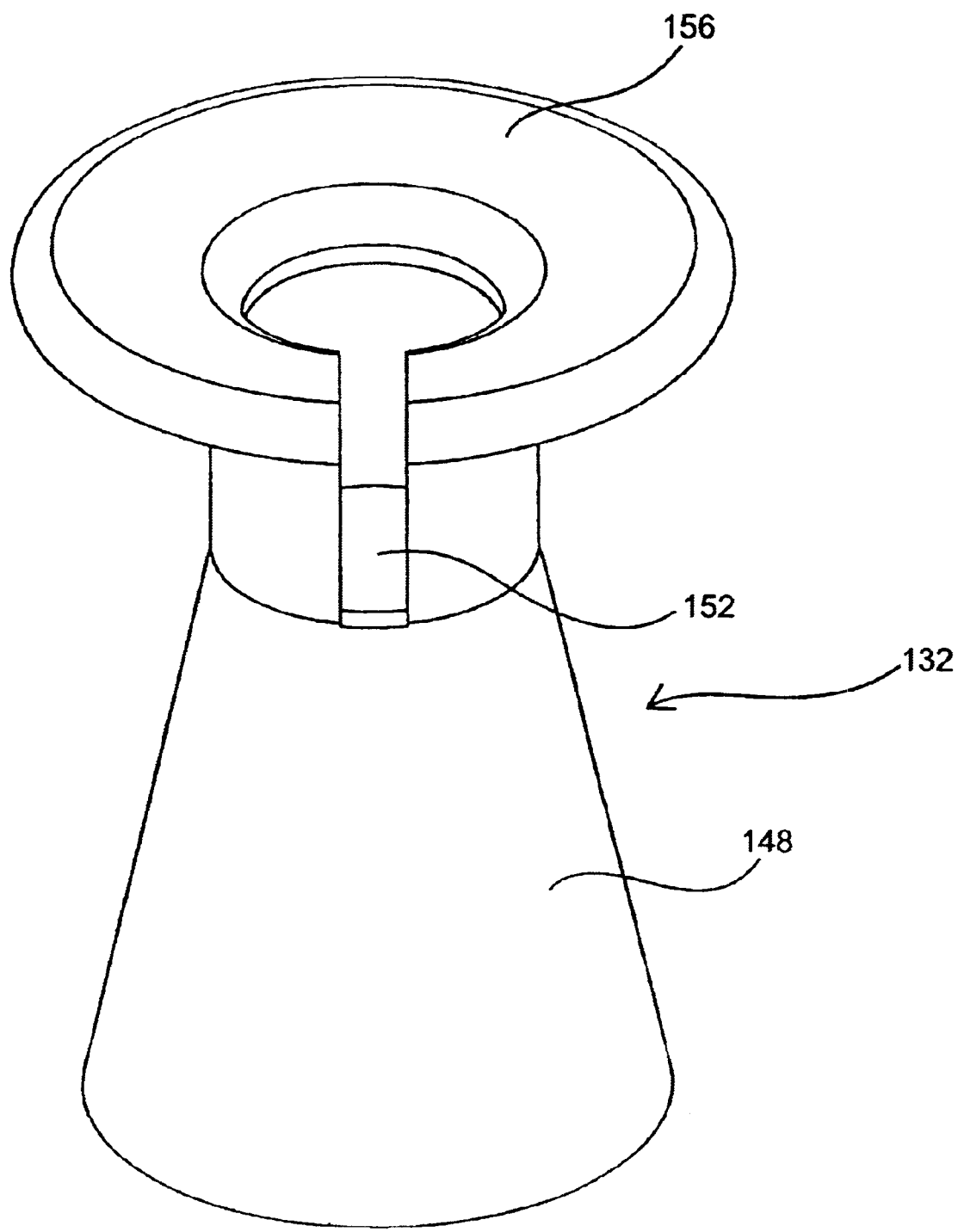
FIG. 17a shows a support device having a partially slotted side and a funneled proximal end.
Figure 18A:
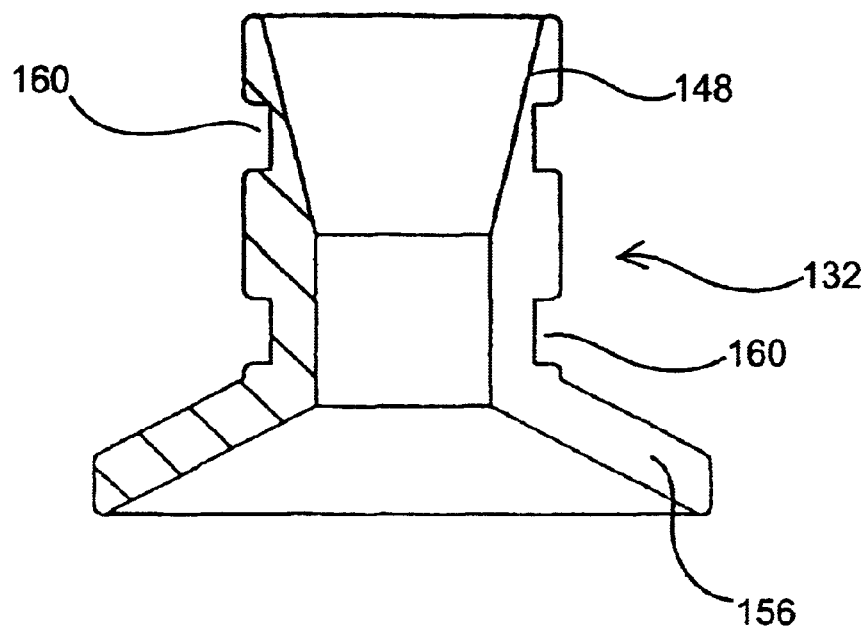
FIGS. 18a and 18b show a slotted end-side fitting having a funneled proximal end.
Figure 18B:
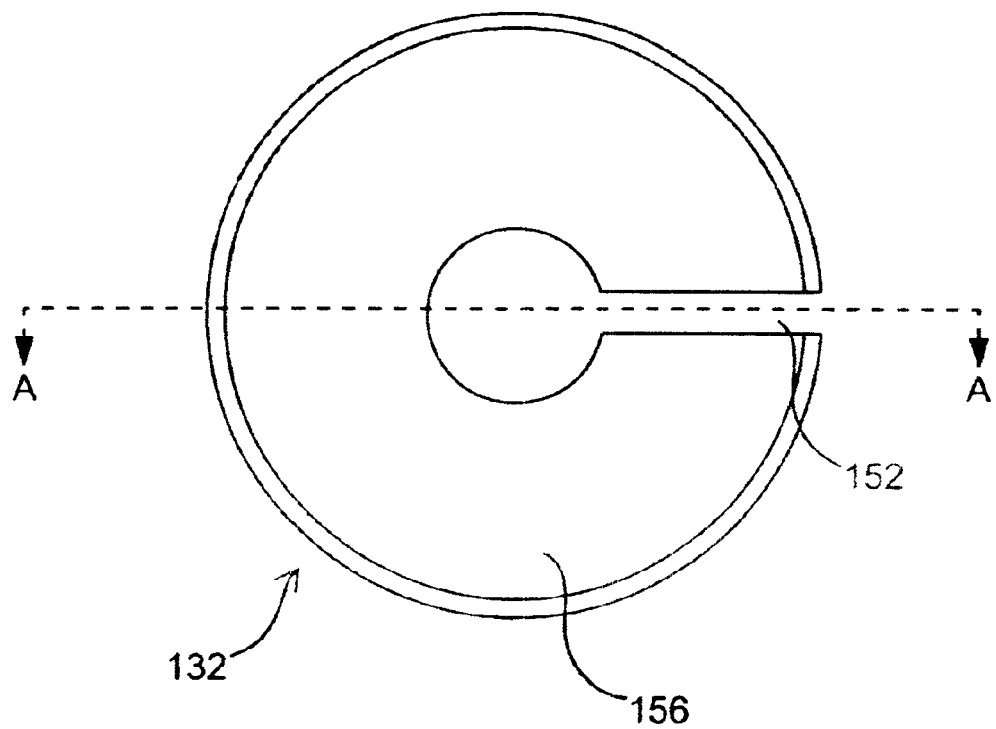
Figure 18C:
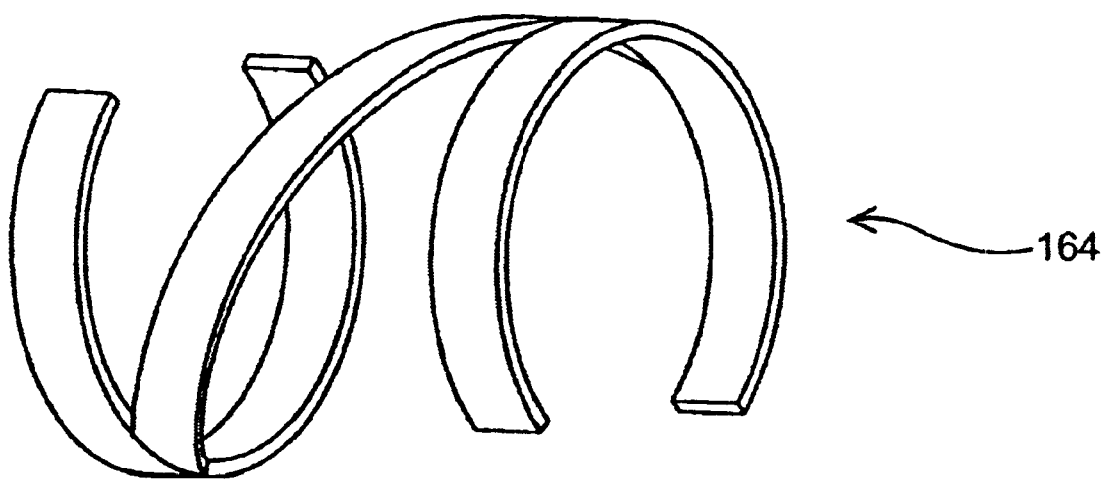
FIG. 18c show a reinforcing structure to secure the support device of FIGS. 18a and 18b.

An alternative support device is shown in FIGS. 18a and b. This support device 132 has a distal flared end 156 to improve the hemostasis of the end-side fitting, a base that contains notches 160 to accept retaining clips for securing to the fitting base, a slot 152 through one side to permit advancing over the side of the fitting base, and a proximal funneled end 148 to improve the compliance and/or blood flow profile transition from the anastomosis to the body of the bypass graft. FIG. 17a shows another support device 132 with a distal flared end 156, a slot 152 to permit advancing over the side of the fitting base, and a funneled proximal end to transition from the anastomosis to the bypass graft and provide a strain relief to prevent kinking of the bypass graft. As shown with fitting 40 and graft 100 in FIG. 16, the support device 132 prevents dramatic overexpansion of the bypass graft, improving the transition from the anastomosis to the body of the bypass graft. This transition is particularly important when using harvested vessels such as the saphenous vein as the bypass graft.

Figure 18D:
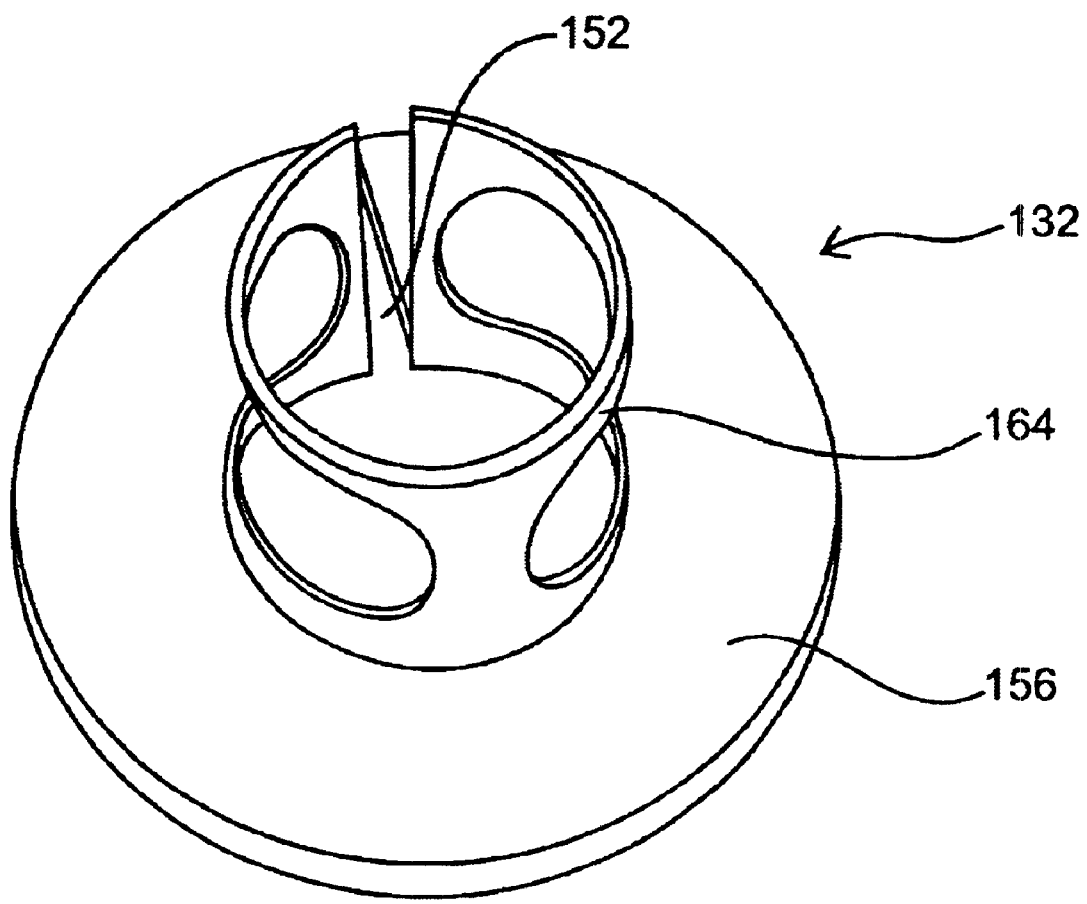
FIG. 18d shows a slotted end-side fitting incorporating a reinforcing structure.

When exposed to arterial blood pressure, saphenous veins tend to balloon, producing turbulent flow at the anastomosis. This may lead to hyperplasia or other unwanted physiologic abnormalities. By creating a smooth transition in diameter and stiffness, the flow profile is improved and the risks associated with compliance mismatch are substantially mitigated. The retaining clip 164 shown in FIG. 18c may be used to secure the support device to the base of the end-side fitting. The distal and proximal rings of the retaining clip 164 fit inside the notches 160 of the support device 132 to prevent axial movement of the retaining clip and support device from the base of the fitting. Alternatively, as shown in FIG. 18d, the retaining clip 164 may be encapsulated inside the stem of the support device 132. This helps reinforce the stem of the support device, especially when the support device is fabricated from compliant materials.

Support devices that have a slot 152 to permit advancing over the side of the fitting base or the side of the bypass graft may incorporate a latching mechanism to lock the edges that define the slot 152 together. This eliminates the need to use another locking mechanism such as a retaining clip, suture, implantable clips, staples, or other device.

Figure 21:
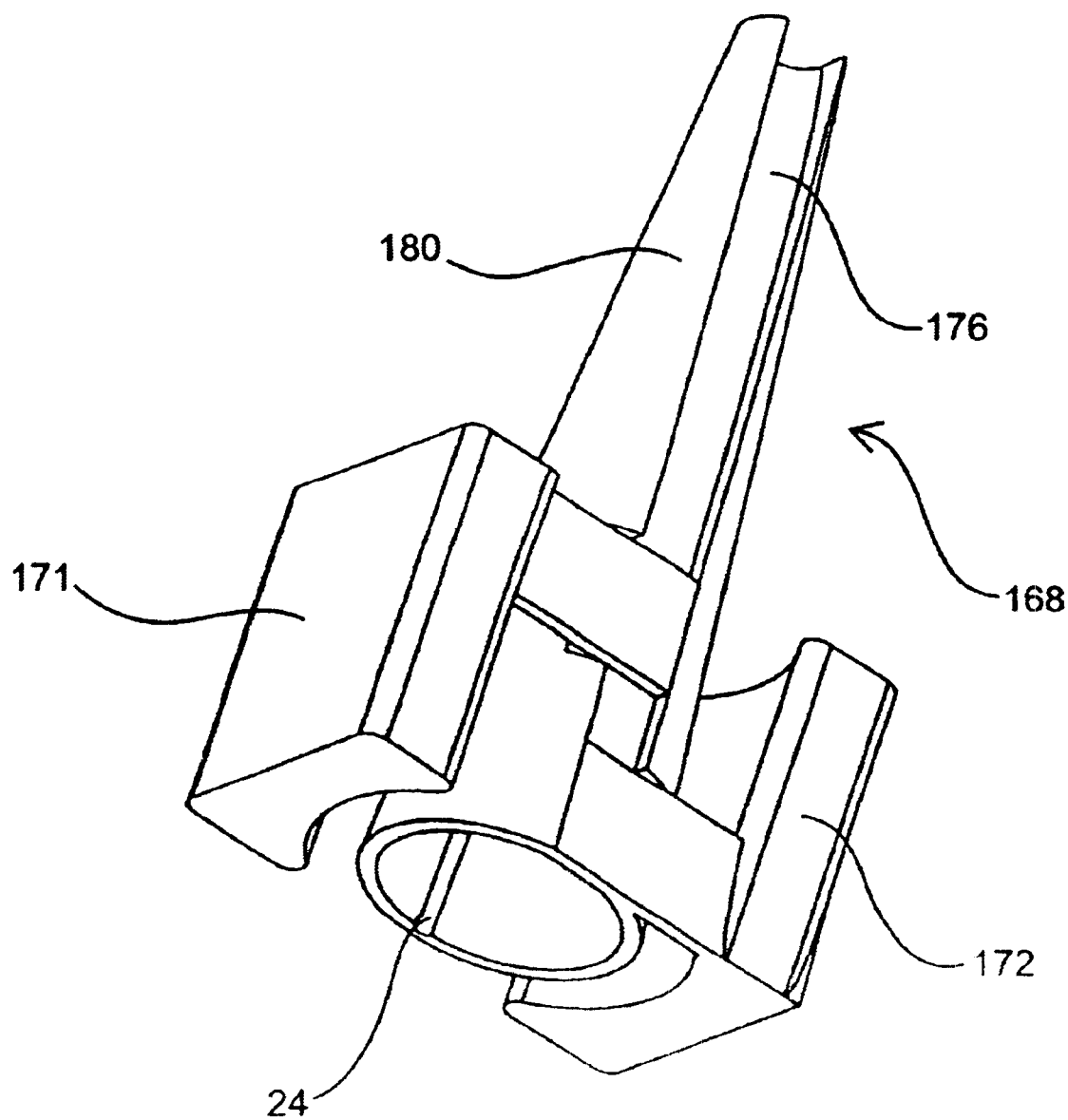
FIG. 21 shows an expansion tool to open up the support device for placement over the stem of the end-side fitting.

FIG. 21 shows an expansion tool 168 used to open the slot of the support device for positioning around the base of the end-side fitting. Knobs 171 and 172 are connected to two sections 180 of expansion tool 168. Sections 180 form a slot 176 along the distal end and an indentation or hinge 24 around which the sections are able to rotate. By squeezing the knobs, the sections are rotated radially outward causing the support device to expand. After positioning the support device, the force causing the knobs to push inward is removed, allowing the expansion tool 168 to return towards its reduced diameter, resting configuration. This expansion tool may also be used to expand the retaining rings, end-side fitting base, or central members described previously.

Figure 19:
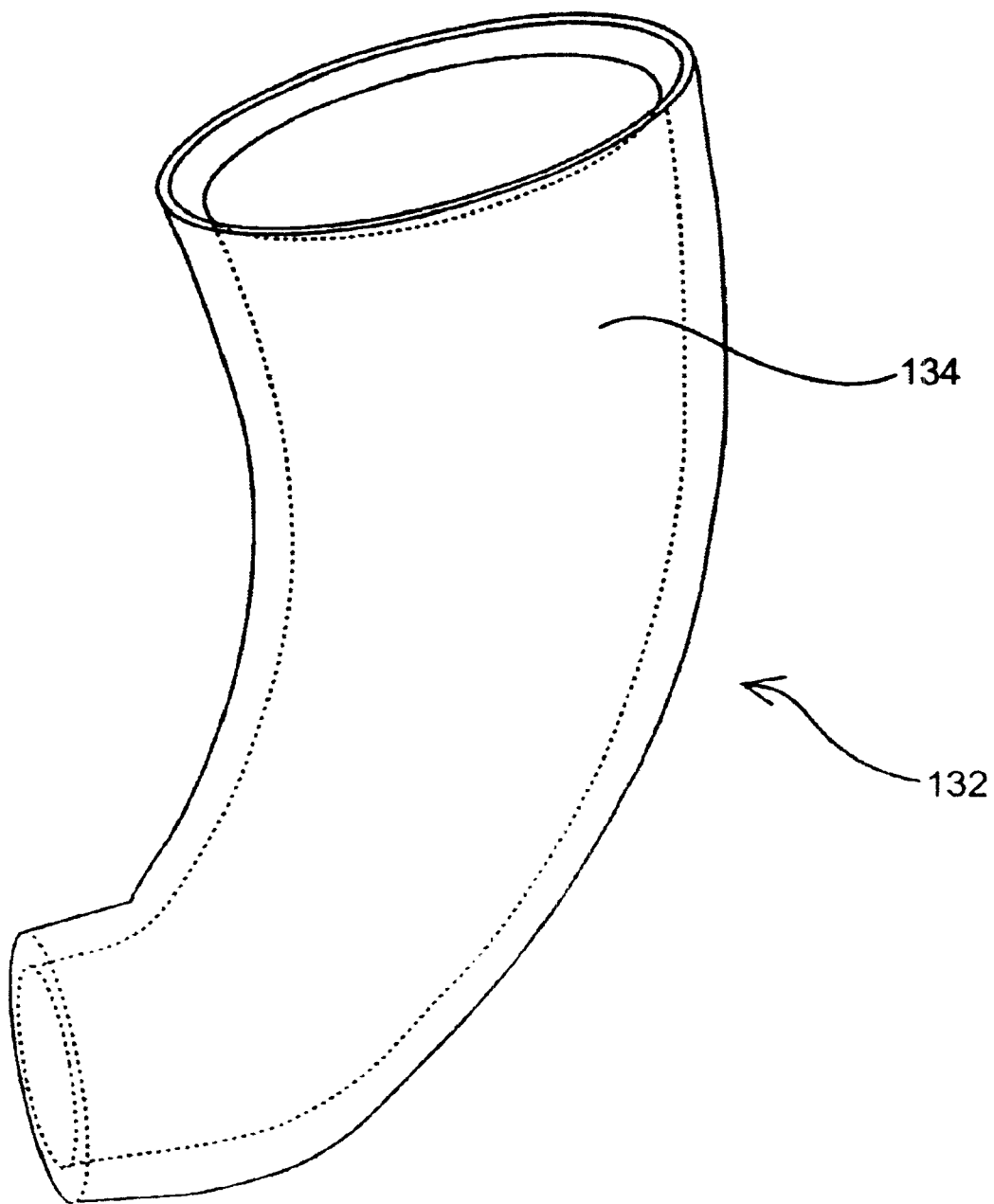
FIG. 19 shows a curved support device having a funneled proximal end.

FIG. 19 shows an alternative support device 132 that has a curved proximal end 134 to provide a strain relief, produce a smooth transition from the anastomosis to the body of the bypass graft, and direct the blood flow through the bypass graft along a predetermined curve.

Figure 20A:
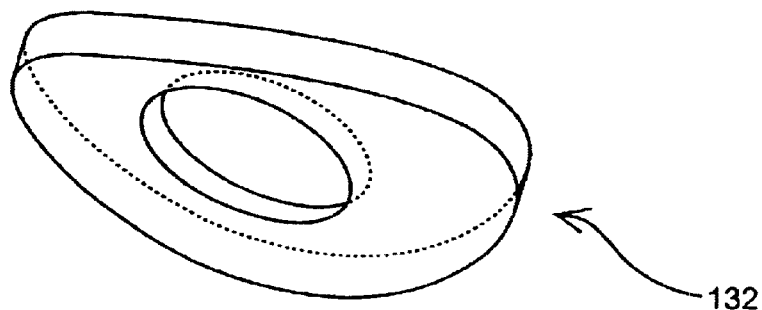
FIGS. 20a to 20c show alternative support device embodiments.
Figure 20B:
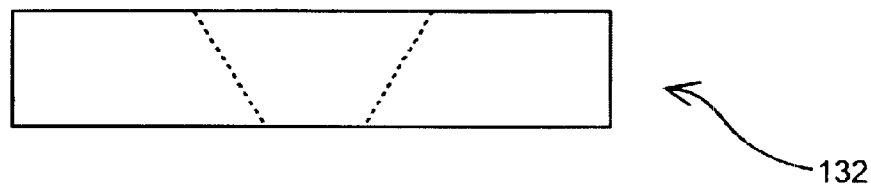
Figure 20C:
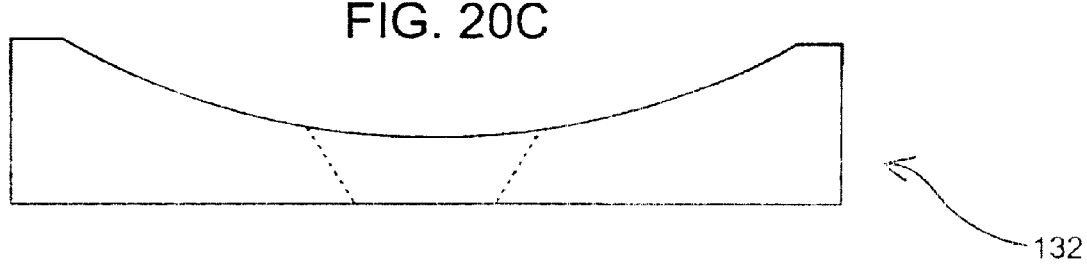

FIGS. 20a to 20c show additional support device embodiments. Of particular note, the curvature of the support device (shown in FIGS. 20a and 20c) depends on the radius of curvature for the host vessel. We prefer that the curvature generally match that of the host vessel to ensure adequate hemostasis at the anastomosis and contact between the support device and the host vessel wall.

Figure 17B:
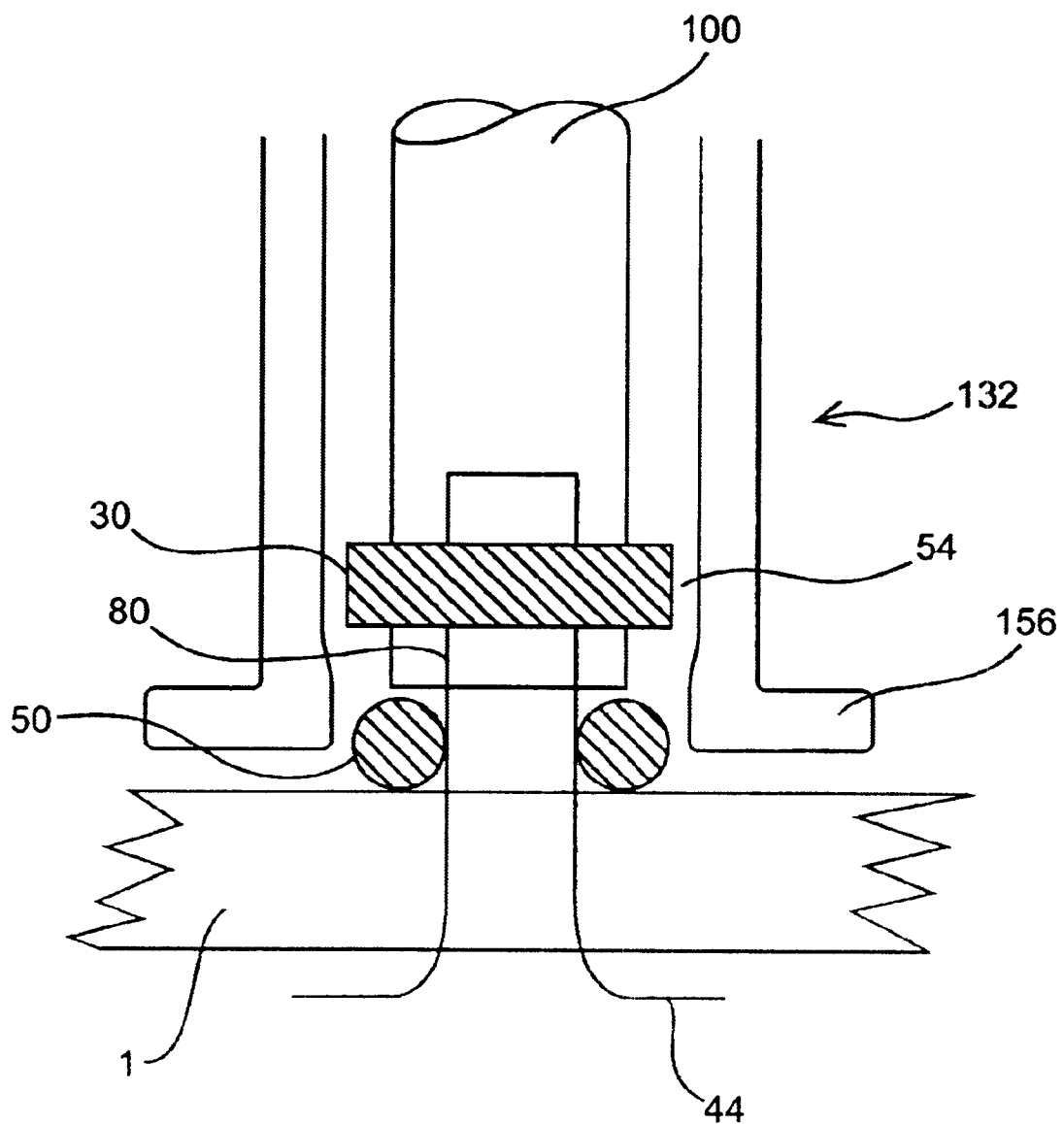
FIG. 17b shows another support device having a separate sealing device.

The support devices described above may also include one or more notches 54 on the interior surface to accept retaining clips 30 used to secure the bypass graft to the base of the fitting, as described above and shown in FIG. 17b. The interior notches 54 are configured to be placed over the retaining clips 30 and maintain consistent contact with the base 80 of the fitting. Otherwise, the retaining clips 30 may cause the support device 132 to bulge away from the base of the fitting in the region where the retaining clips are located. The support device 132 shown in FIG. 17b may additionally include an interface sealer 50 designed to further eliminate blood leakage at the opening between the host vessel wall 1 and the base of the fitting. The interface sealer 50 may be positioned at the opening between the base of the fitting and the host vessel wall prior to positioning the support device 132 such that the interface sealer 50 is constrained by the distal flared end 156 of the support device 132. The interface sealer 50 may be fabricated from collagen, fibrin structures, or other materials known to promote cellular growth or platelet adhesion and result in sealing or stabilization of the anastomosis site. The interface sealer 50 is preferably compliant and capable of deforming to match gaps or voids between the opening through the host vessel wall and the base of the fitting.

Deployment Systems

Conventional anastomosis techniques require a relatively large incision through the vessel wall and use sutures, commercially available clips, or stapling devices to bond the end of the bypass graft to the edges of the punch created in the vessel wall. In certain cases, the structural integrity of the vessel wall may be weakened, causing the vessel to collapse at the anastomosis site. This is especially true when the bypass graft is not appropriately aligned to the host vessel incision. Therefore, the deployment system of the present invention is designed to quickly access the host vessel through a small puncture in the vessel wall. As such, the deployment system is designed to prevent excess blood loss when accessing the host vessel and deploying the bypass graft and fitting combination, thereby eliminating the need to stop or re-route blood flowing through the host vessel. This approach also improves the leak resistance around the fitting due to elastic compression of the vessel wall around the fitting and automatically aligns the bypass graft to the host vessel wall at the anastomosis site.

For surgical applications, physicians are able to access the anastomosis sites from the exterior surface of the host vessel(s). The deployment system of the surgical approach must permit removal after both ends of the bypass graft are secured and the delivery system resides around the attached bypass graft. The deployment system leverages conventional intravenous access techniques to produce an opening through the host vessel wall. Guidewires have commonly been used to gain access into the host vessel after puncturing the host vessel wall with a needle. In addition, the technique of inserting a sheath into a host vessel by advancing it over a dilating mechanism and a guidewire is commonly used when performing the Seldinger technique during catheterization procedures.

The sheath and dilating mechanism of the deployment system may be constructed from polyethylene, polycarbonate, PEEK, or other polymer that may be extruded or injection molded into a tube having the desired cross-sectional profile. The sheath and dilating mechanism of the deployment system may incorporate a braided, woven, or wound layer laminated between two polymer layers to resist kinking and improve the column strength and torque response. A taper and radius may be formed in the components of the deployment system by thermally forming the tubing into the desired shape or incorporating such features in the injection molding cast. In addition, the components of the deployment system may incorporate a softer distal tip fabricated by thermally bonding a short section of lower durometer tubing to the sheath or tapering the thickness of the sheath tubing.

To prevent the backflow of blood through deployment sheaths, hemostatic valves may be used. The hemostatic valves prevent blood leakage but permit insertion of a device such as a fitting with an attached bypass graft through the sheath. The hemostatic valve of the delivery system of the invention also incorporates a mechanism to separate along at least one side and remove from around the bypass graft. To accomplish this, the hemostatic valve is attached to the hub of the sheath and includes a mechanism to separate along at least one side. To incorporate a splitting mechanism in the deployment sheath, at least one groove, series of perforations, slot, slit, or combination of these features are incorporated in the sheath tubing and hub member. The at least one groove, series of perforations, slot, slit, or combination of these features may be fabricated while injection molding or otherwise manufacturing the sheath tubing and/ or hub, or may be formed in the assembled sheath by subsequent laser drilling, milling, or other suitable manufacturing process.

The petals of the end-side fitting are compressed forward, into a reduced outer diameter while inserting the end-side fitting, with bypass graft attached, through the sheath of the deployment system. To facilitate this step, a loading sheath 16 (shown in FIGS. 1b and 1e) may be used to maintain the petals in the compressed orientation, open the hemostatic valve to access the interior of the deployment sheath, and provide a smooth transition from the interior of the loading sheath to the interior of the deployment sheath. The loading sheath 16 also protects the bypass graft while inserting through the deployment sheath. The proximal end of the loading sheath 16 incorporates wings 12 separated by approximately 45 to 135 degrees. The wings 12 are squeezed together to open the slot 20 through the loading sheath 16 for positioning around and removing the loading sheath from the side of the bypass graft. A longitudinal indentation 24 provides a pivot around which the sections of the loading sheath are rotated to open the slot 20. The wings 12 also provide a stop to prevent advancing the loading sheath past the proximal end of the deployment sheath.

Figure 1C:
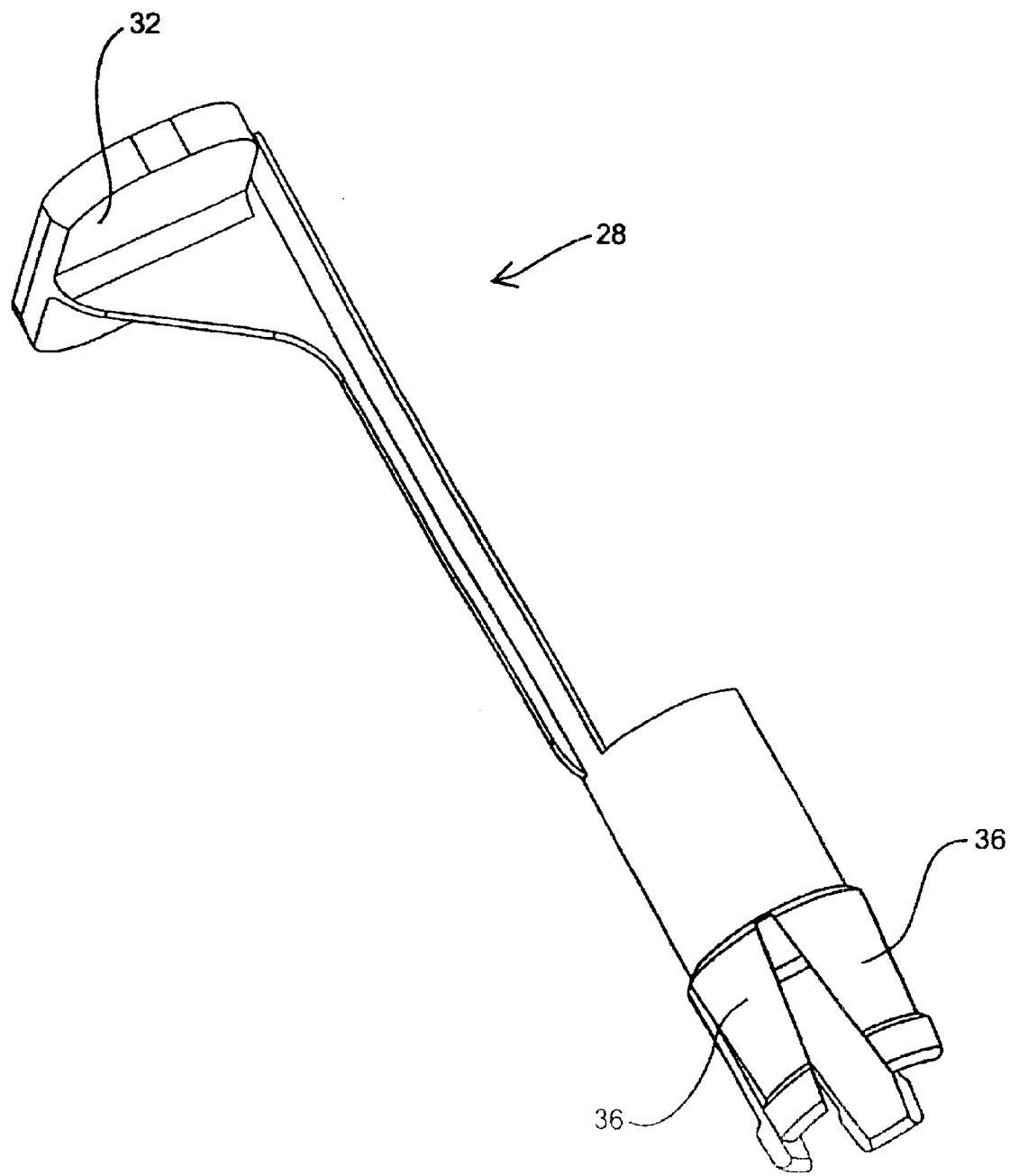
FIG. 1c shows a plunger.

FIG. 1c shows a plunger 28 used to advance the end-side fitting and attached bypass graft past the end of the loading sheath 16. The plunger 28 has a proximal handle 32 used to push the distal end of the plunger thereby the end-side fitting and attached bypass graft past the distal end of the loading sheath 16. The plunger further incorporates grasping legs 36 that are tapered in thickness and are separated radially around the plunger so as to accommodate variances in the outer diameter of the end-side fitting and/or enable grabbing the end-side fitting without damaging the device during deployment. Another plunger embodiment (not shown) may be configured exactly like the loading sheath, described above, except with a slightly smaller outer diameter so it can fit inside the loading sheath 16.

Figure 1D:
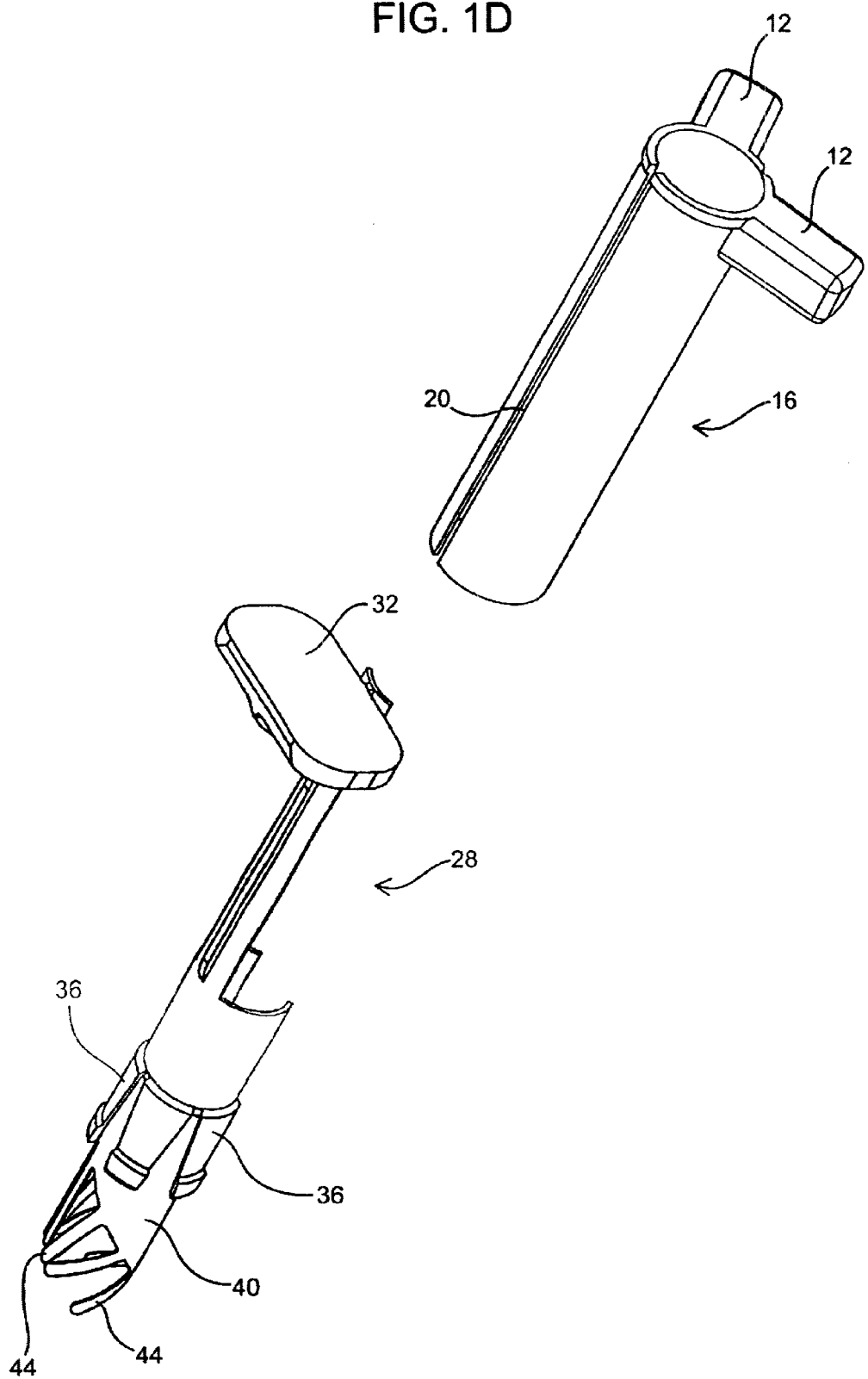
FIGS. 1d and 1e show the operation of the loading sheath and plunger.
Figure 1E:
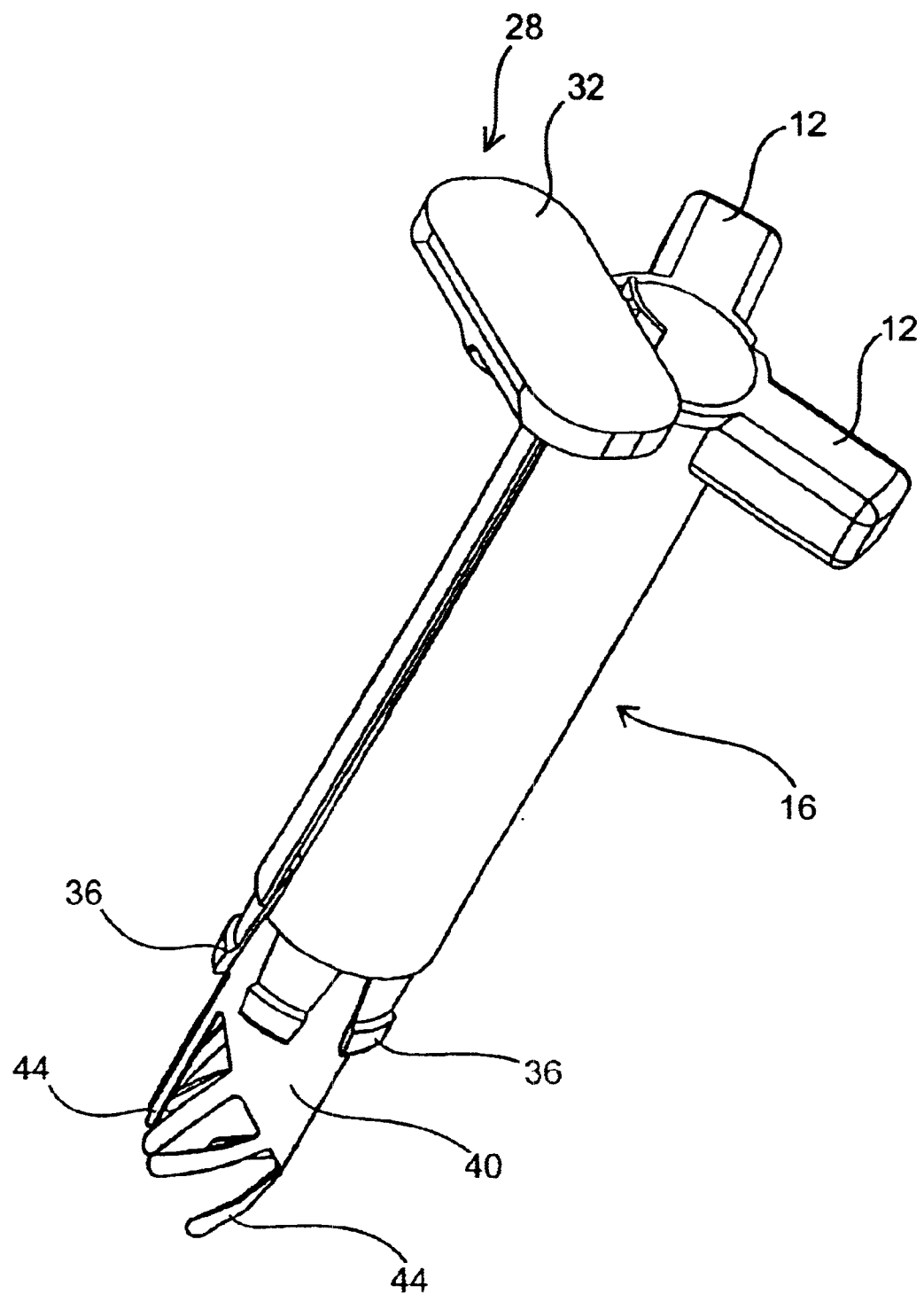
Figure 1F:
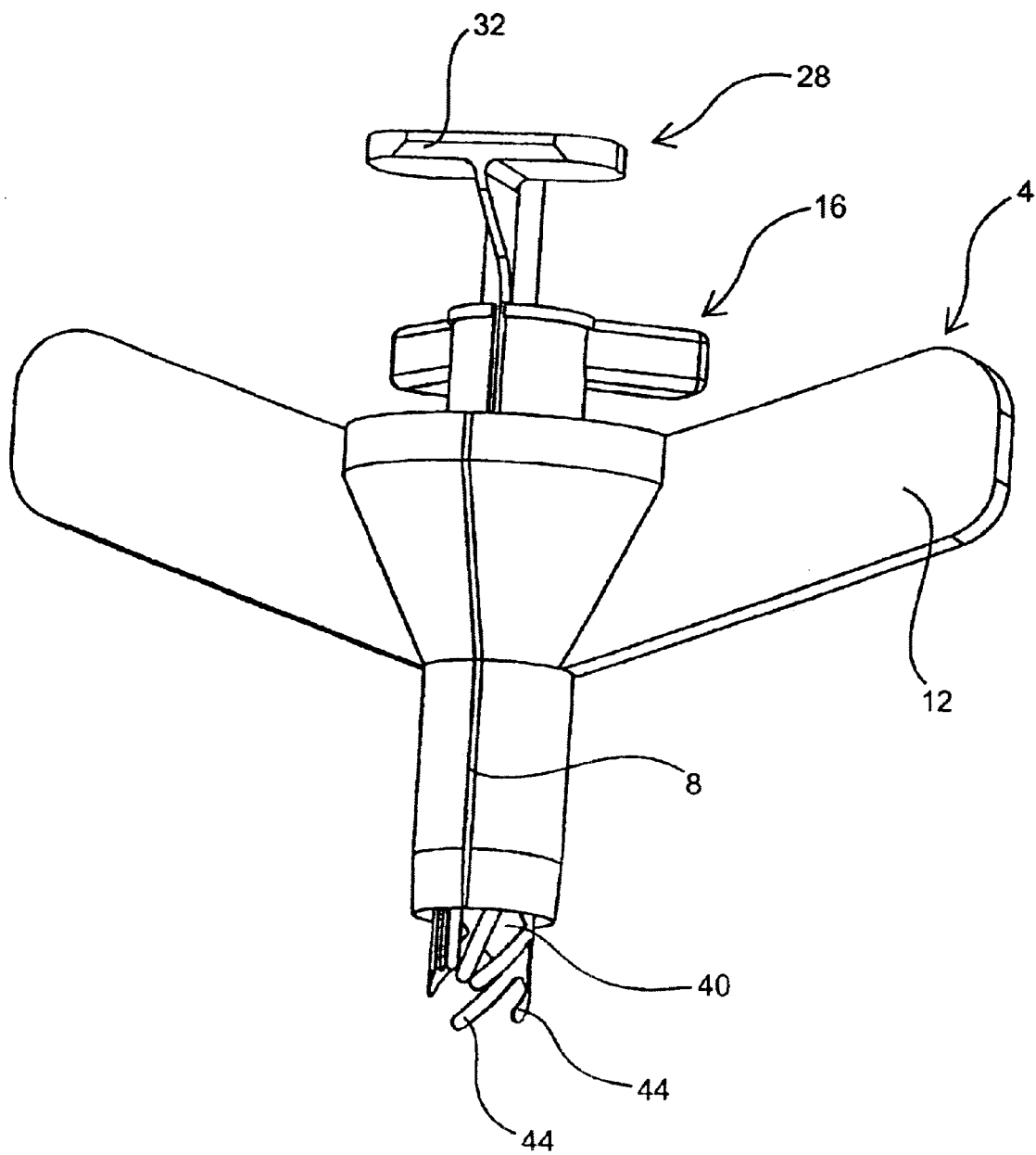
FIG. 1f shows the operation of the deployment sheath of FIG. 1a, the, loading sheath, and plunger.

As shown in FIGS. 1d to 1f, the loading sheath 16 and plunger 28 operate together to facilitate advancing the end-side fitting and attached bypass graft through the deployment sheath 4 (shown separately with wings 12 and split 8 in FIG. 1a). The end-side fitting 40 is preloaded into the loading sheath 16 such that the petals 44 are compressed into a reduced diameter inside the loading sheath 16 (not shown). A removable clip may be used to hold the sections of the loading sheath 16 closed to prevent one of the compressed petals 44 from extending through the longitudinal slot 20 that enables separating the sides of the loading sheath to remove it from around the bypass graft. As shown in FIG. 1f, the loading sheath, with the petals 44 of the end-side fitting compressed into a reduced diameter, is advanced through the deployment sheath 4 such that the distal end of the loading sheath 16 abuts, extends beyond, or approximates the distal end of the deployment sheath 4. Then, the plunger 28 is used to advance the end-side fitting past the distal end of the loading sheath and deployment sheath where the petals 44 expand towards their resting orientation. This methodology requires advancing the end-side fitting only a short distance (approximately 2 to 8 mm) along the loading sheath 16 and deployment sheath 4 before the petals 44 extend past the distal ends of the loading sheath 16 and deployment sheath 4 where the petals 44 can expand towards their resting orientation.

After positioning the end-side fitting inside the host vessel, the deployment system may be used to help manipulate the end-side fitting such that the petals 44 contact the interior surface of the host vessel and hold the position of the end-side fitting as a support device is positioned and locked to the base of the end-side fitting. After securing the end-side fitting, the deployment sheath 4 is split along at least one side 8 and removed from around the bypass graft. Then the wings 12 of the loading sheath 16 are squeezed to open the longitudinal slot 20 and provide an opening to remove the loading sheath from around the bypass graft. Then the plunger 28, also having a slot defining a longitudinal opening, is pulled from around the bypass graft.

Figure 2A:
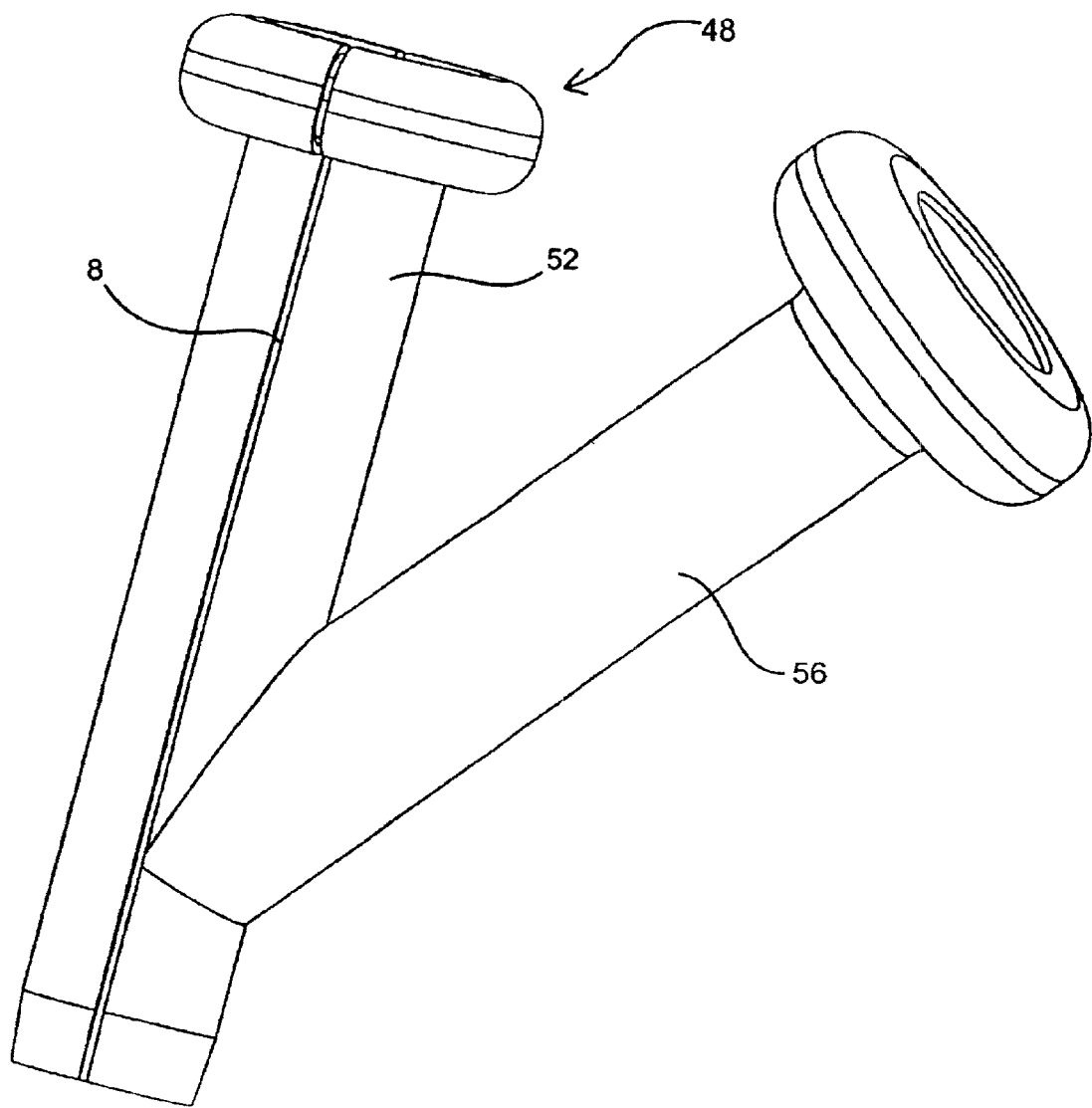
FIG. 2a shows a splittable "Y" deployment sheath.

Alternative deployment sheaths are shown in FIGS. 2a to 2e. In FIG. 2a, the deployment sheath 48 is configured with a second port 56 branching from the removable port 52 used to advance the end-side fitting and attached bypass graft into the host vessel. The branching port 56 is used to provide an access through which the dilator is placed. As a result, the end-side fitting (not shown) may be preloaded into the removable port 52 of the deployment sheath before the deployment sheath is advanced over a dilator and into the host vessel. This decreases the need to load the end-side fitting after the deployment sheath is positioned, and prevents blood leakage during the loading step.

Figure 2B:
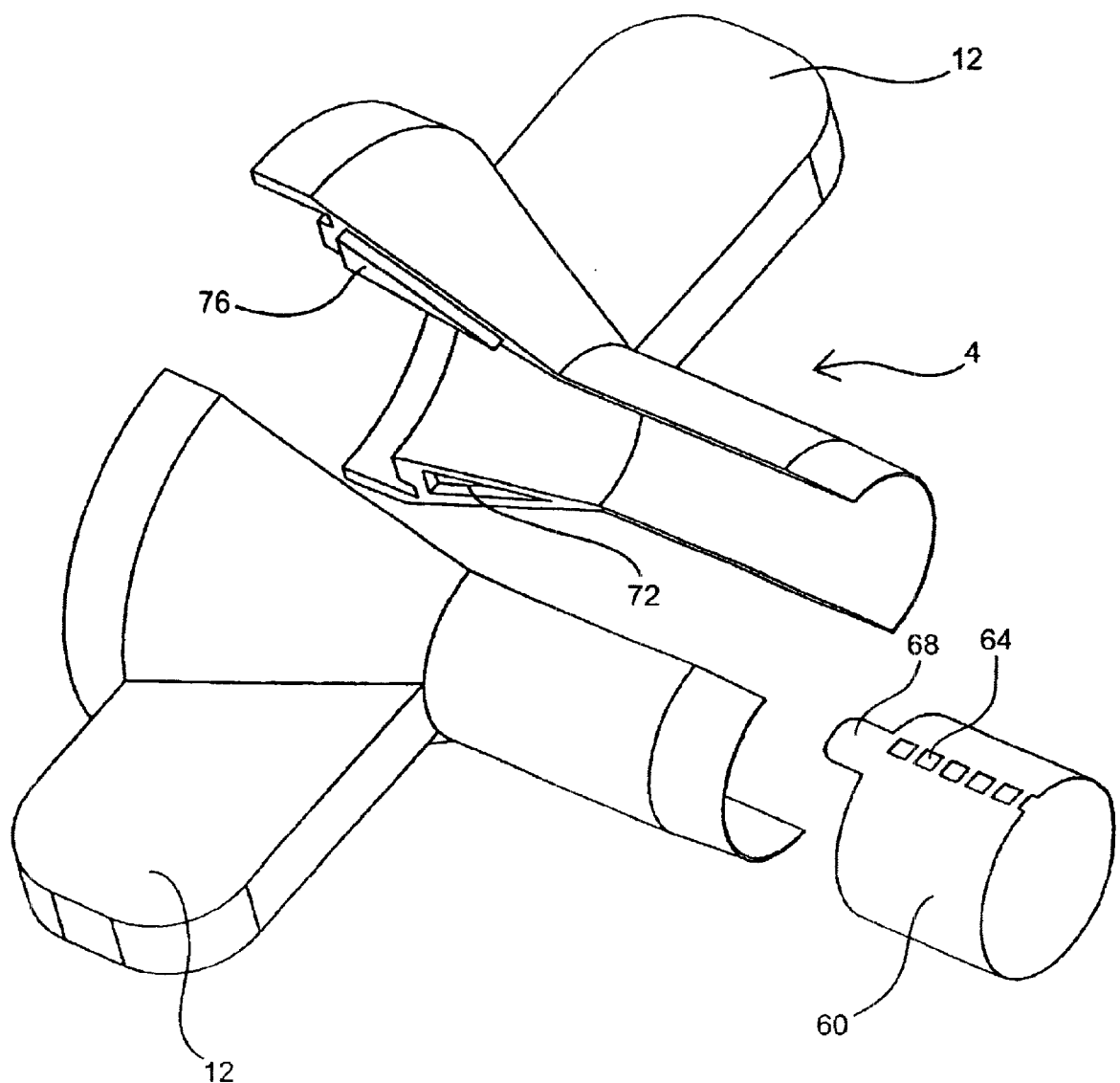
FIG. 2b shows the components of another deployment sheath embodiment.
Figure 2C:
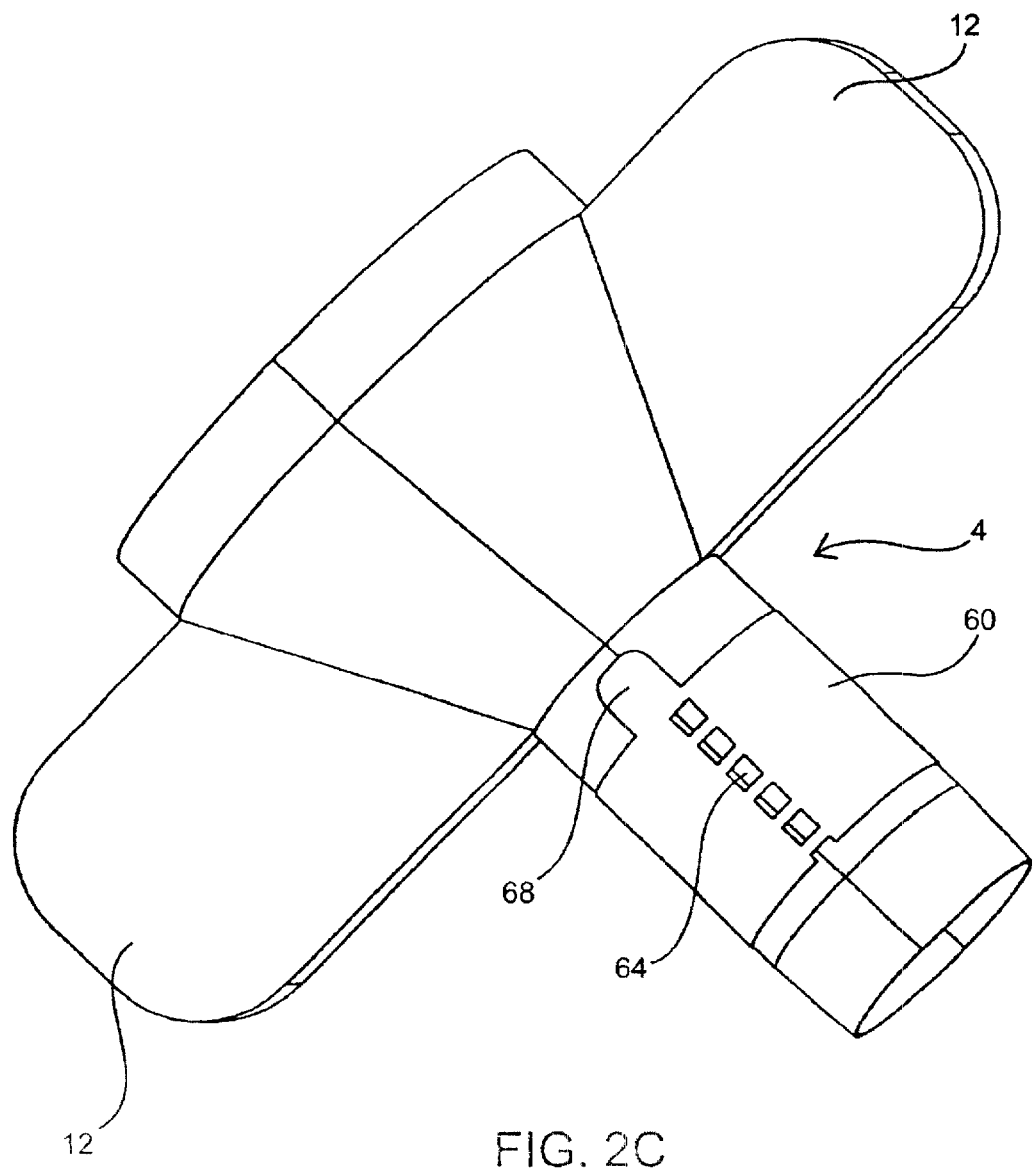
FIG. 2c shows the intact deployment sheath of FIG. 2b.
Figure 2D:
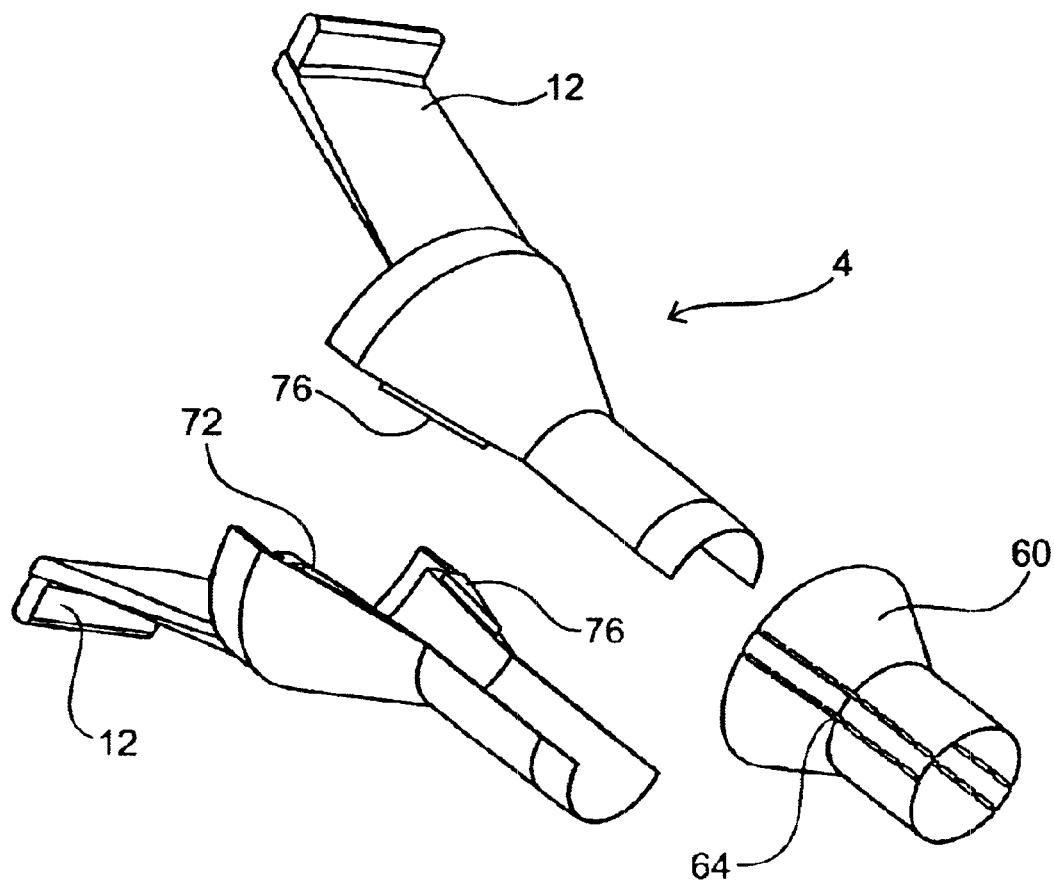
FIGS. 2d and 2e show an additional deployment sheath embodiment.
Figure 2E:
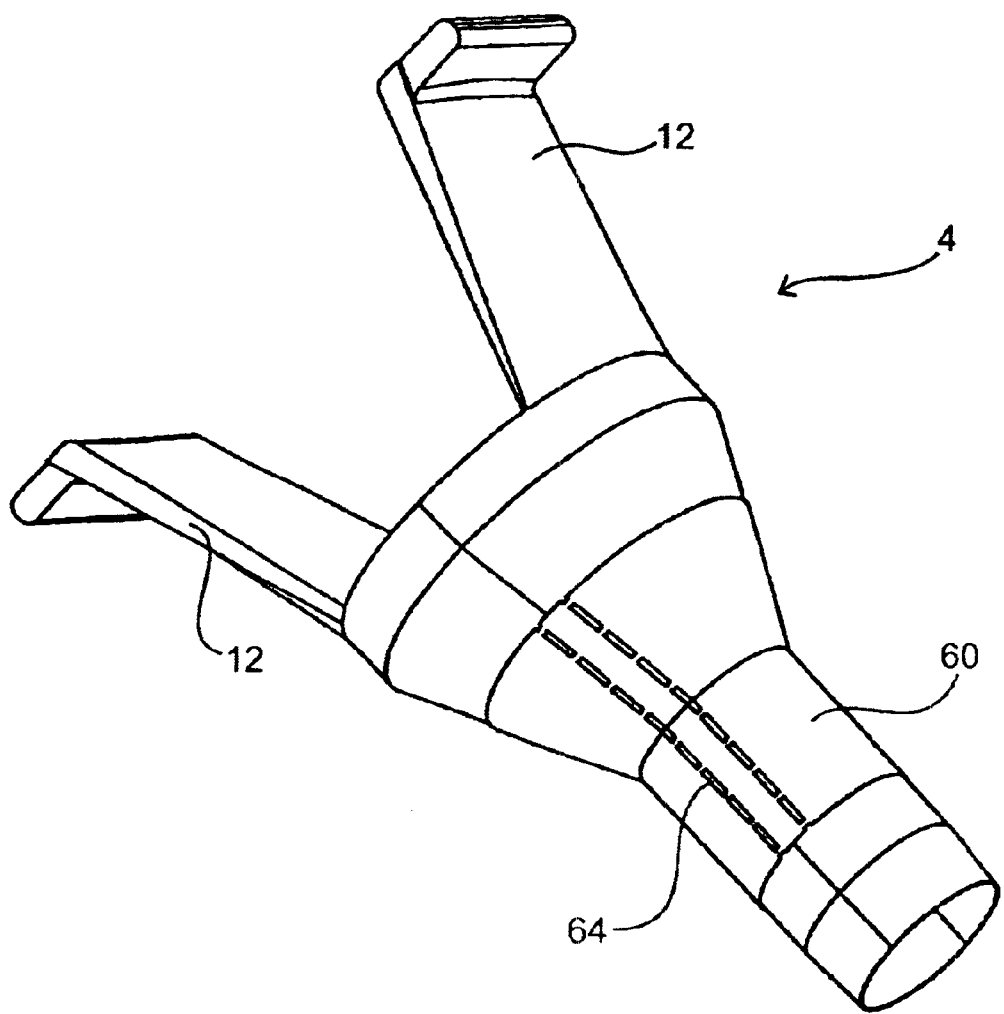

Tailoring the force required to tear removable sheaths is difficult, and the leverage a surgeon has remotely hinders this aspect of the deployment sheath. FIGS. 2b to 2e show two deployment sheath embodiments involving pre-split deployment sheath halves held together with perforated tubing 60. These deployment sheaths are pre-split along at least one side with the perforated tubing 60 maintaining the pre-split deployment sheaths as intact units and providing a leak-resistant barrier along the at least one split side. When the deployment sheaths are fabricated as two halves (two longitudinal splits sides) as shown in FIGS. 2b and d, indentations 72 and protrusions 76 that match the indentations are included in the deployment sheath sections. This helps orient the sheath halves and enhances the leak resistance when the halves are locked together. The perforated tubing holding the pre-split deployment sheaths 4 intact may be fabricated from PET, PTFE, or other material that may be mechanically drilled, etched, laser drilled, or perforated using suitable manufacturing processes. Preferably, the perforated tubing 60 is fabricated from a heat shrink tubing such that is can be easily positioned over the pre-split deployment sheath 4 and thermally shrunk to bond the pre-split sheath as an intact unit. The perforated tubing 60 may incorporate extensions 68, which may extend substantially past the proximal end of the sheath (not shown), to tear the tubing along the perforations 64. This permits remote separation of the deployment sheath 4 with significantly less force than the removable sheaths that are fabricated as intact units with grooves to permit tearing along at least one side. In the pre-split deployment sheath embodiments, the perforated tubing 60 is preferably bonded to the sections of the deployment sheath using ultrasonic welding, adhesives, thermal bonding, laser welding, or other suitable manufacturing process. The perforated tubing 60 may additionally follow the contours of the pre-split sheath as shown in FIGS. 2d and 2e. This deployment sheath embodiment is removed by pulling the wings 12 apart, which causes the perforated tubing 60 to separate along the perforations 64, similar to unzipping a zipper.

Figure 2F:
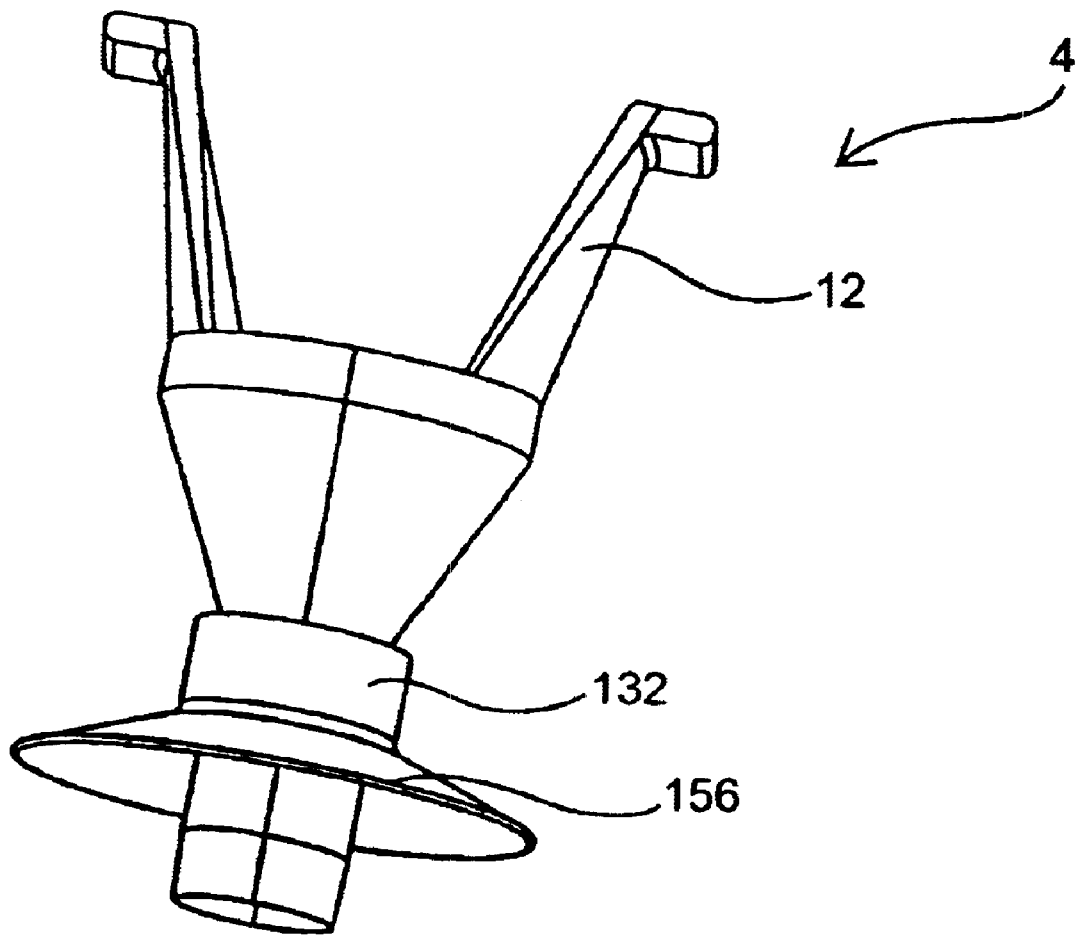
FIG. 2f shows another deployment sheath embodiment.

The pre-split deployment sheath embodiment shown in FIGS. 2d and 2e may be modified to replace the perforated tubing with the support device 132, as shown in FIG. 2f. The support device 132 includes a flared distal end 156 (as described above) and may include other features of support devices, described above, such as a funneled proximal end (not shown), notches, etc. The support device 132 maintains the pre-split deployment sheath 4 in a closed position until the support device is advanced past the distal end of the deployment sheath and onto the base of the end-side fitting. This simultaneously secures the end-side fitting to the host vessel and enables removing the deployment sheath from around the bypass graft. This pre-split deployment sheath 4 may have one or more longitudinal splits permitting forming an opening along at least one side to remove the deployment sheath from around the bypass graft.

In an alternative pre-split deployment sheath embodiment, the deployment sheath 4 is fabricated with a longitudinal split along one side. The side opposite of the longitudinal split incorporates a hinge 24 for separation similar to that described for the loading sheath above and shown in FIG. 1b. The split sides incorporate a mechanical latching mechanism capable of causing the sides to engage and lock together; this provides a hemostatic barrier along the split. The edges of the split side may be grooved or incorporate matching raised and detented areas to align the edges of the split side when closed. After positioning and securing the end-side fitting, the wings 12 are squeezed together causing the latching mechanism to disengage and the longitudinal side to open, thus permitting removal of the deployment sheath from around the bypass graft.

An additional deployment system embodiment not shown incorporates a screw-in mechanism similar to that described for the screw-in end-side fitting such that the deployment system may be advanced, with or without the aid of a guidewire, through a small opening in the host vessel wall, without the need for a dilator.

These deployment sheath embodiments may be used with the loading sheath and plunger as previously described.

Sheathless End-Side Fittings

Figure 15A:
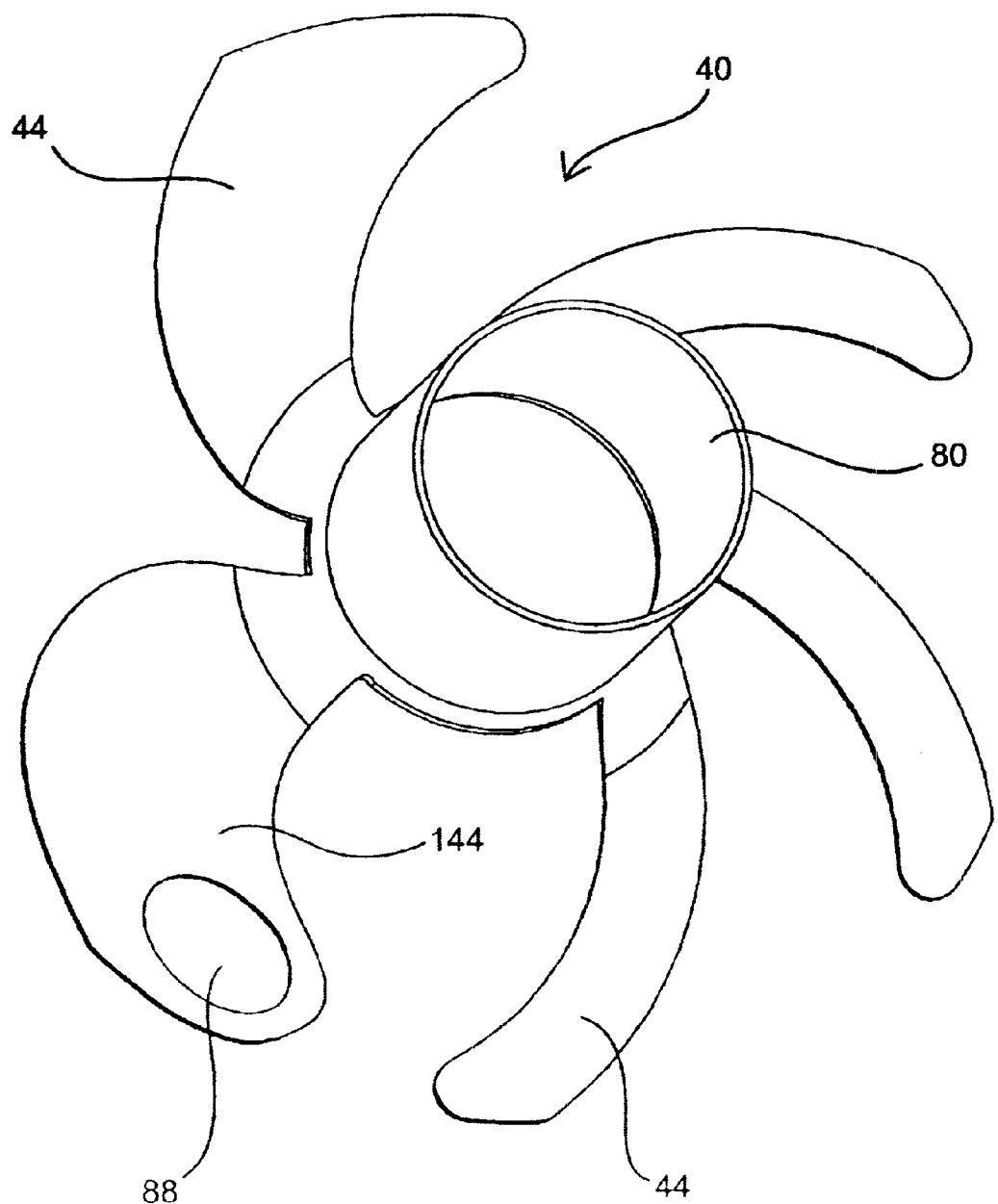
FIG. 15a shows a screw-in end-side fitting embodiment.

As previously discussed in co-pending U.S. patent application Ser. No. 09/329,503 filed Jun. 10, 1999 and co-pending Provisional Application Serial No. 60/111,948 filed Dec. 11, 1998, each of which is incorporated herein by reference, end-side fitting embodiments having specific characteristics may be inserted through a small puncture without the need for a deployment sheath. FIG. 15a shows a screw-in end-side fitting 40 that meets these requirements. The screw-in end-side fitting incorporates a mechanism to follow a guidewire and/or open a puncture through a host vessel wall. In this embodiment, a hole 88 (which is preferably, but not necessarily, oval) in the leading petal 144 is adapted to follow a guidewire previously inserted through the host vessel wall and into the lumen. The guidewire, previously inserted through the host vessel wall using a needle, is inserted through the hole 88 such that when the end-side fitting is angled, the distal tip of the leading petal 144 follows the surface of the guidewire. This produces a smooth transition from the guidewire to the leading petal 144. As the end-side fitting is rotated, the leading petal expands the opening through the vessel wall. Upon further rotation, the remaining petals 44 (which are curved to follow the opening through the host vessel wall) further expand the opening causing the petals to advance into the interior of the host vessel. When the end-side fitting is fully rotated 360 degrees, the entire end-side fitting is positioned inside the host vessel. Then a support device, previously discussed, is advanced over the base of the end-side fitting and is locked in place to maintain the position of the end-side fitting and prevent blood leakage from between the opening through the host vessel wall and the exterior surface of the base of the end-side fitting.

Another screw-in end-side fitting embodiment is shown in FIG. 15b. A gap 228 is defined between the leading petal 144 and the trailing petal 236. Slots 84 extend around the end-side fitting separating the petals 144, 44, and 236 to increase flexibility and limit the surface area of petals exposed within the vessel. An outer connecting link 232 improves the torque response of the fitting for advancing the end-side fitting through the puncture and into the host vessel. A hole 80 may also be incorporated so the end-side fitting follows a guidewire during insertion through and dilation of a puncture.

FIGS. 14a to 14f show another system for inserting an end-side fitting without requiring the use of a deployment sheath. As previously discussed, a guidewire 140 is inserted through the host vessel wall 1 and into the host vessel interior. The end-side fitting has a distal hole or aperture 88 to pass over the guidewire and a proximal hole or aperture that also accepts the guidewire. The distal hole 88 provides a smooth transition from the guidewire 140 to the leading petal of the end-side fitting to readily advance the leading petal 144 through the opening in the host vessel wall 1. The leading petal 144 has a smooth transition to the base of the end-side fitting to dilate the opening while the end-side fitting is advanced over the guidewire and through the host vessel wall opening. The cross-section (not shown) of the leading petal 144 is an arc having a radius of curvature that approximates the radius of curvature of the host vessel 1.

Figure 14A:
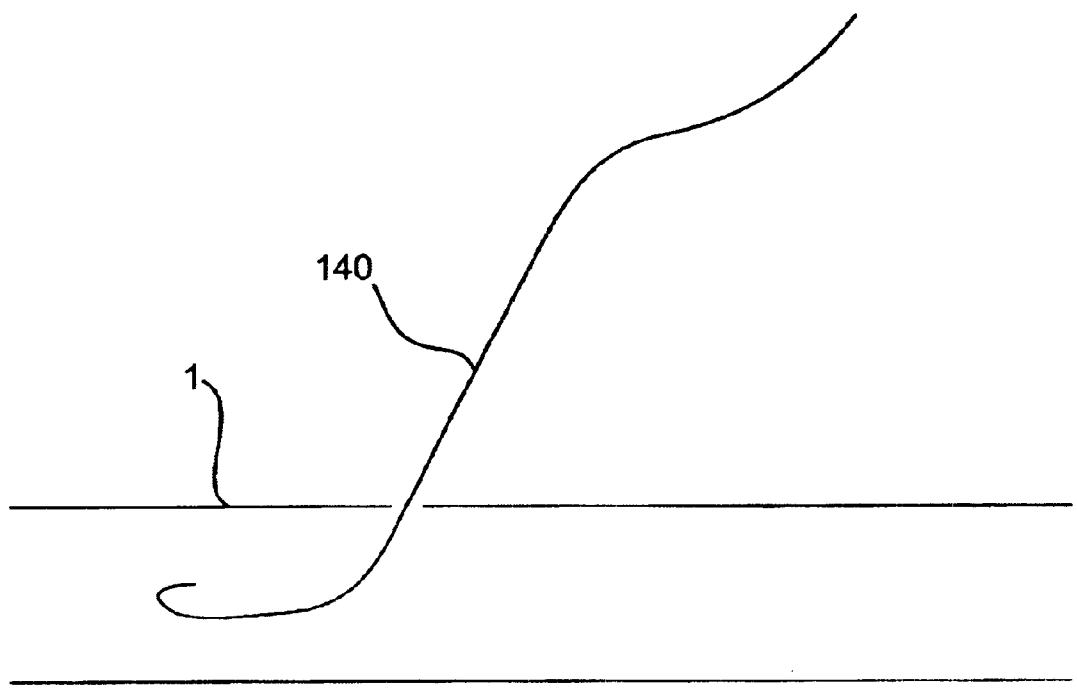
FIGS. 14a to 14f show an end-side fitting capable of being deployed over a guidewire and the deployment steps to position and secure the end-side fitting.
Figure 14B:
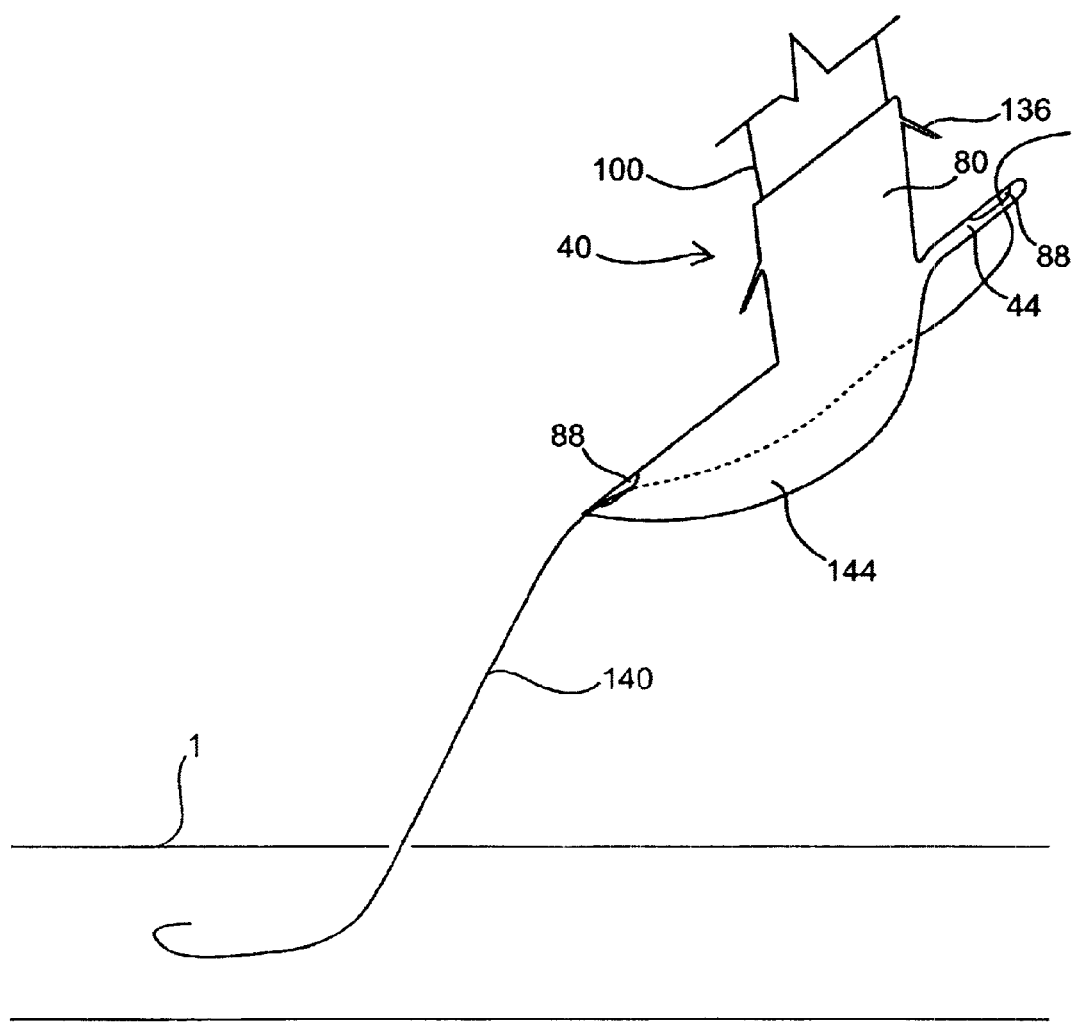
Figure 14C:
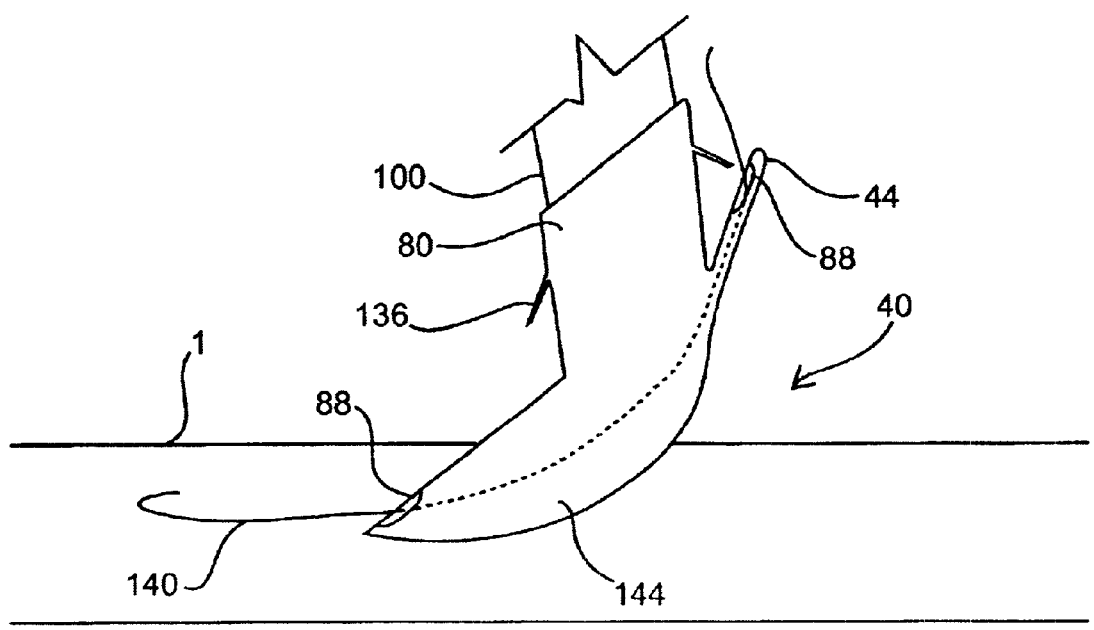
Figure 14D:
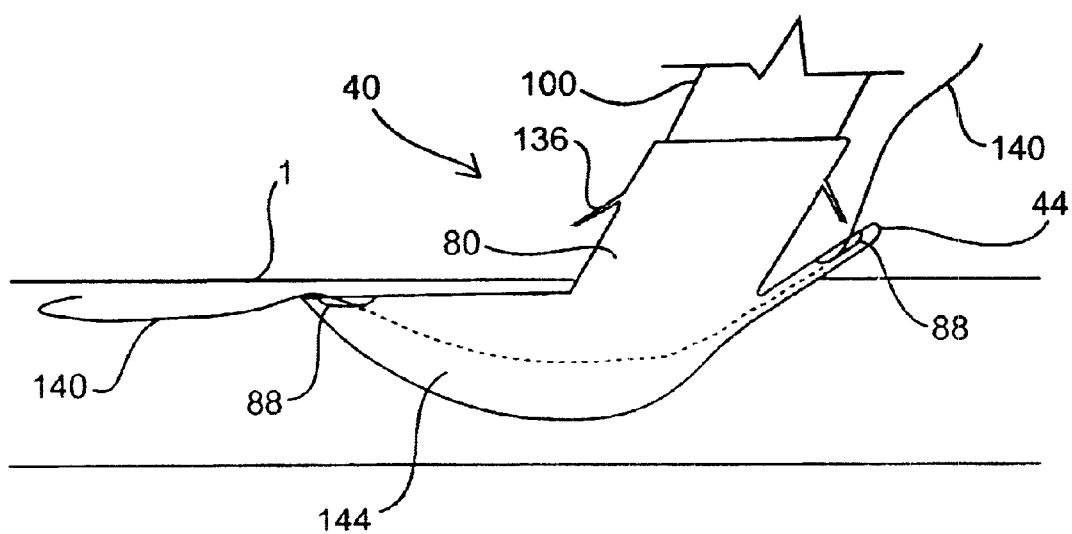
Figure 14E:
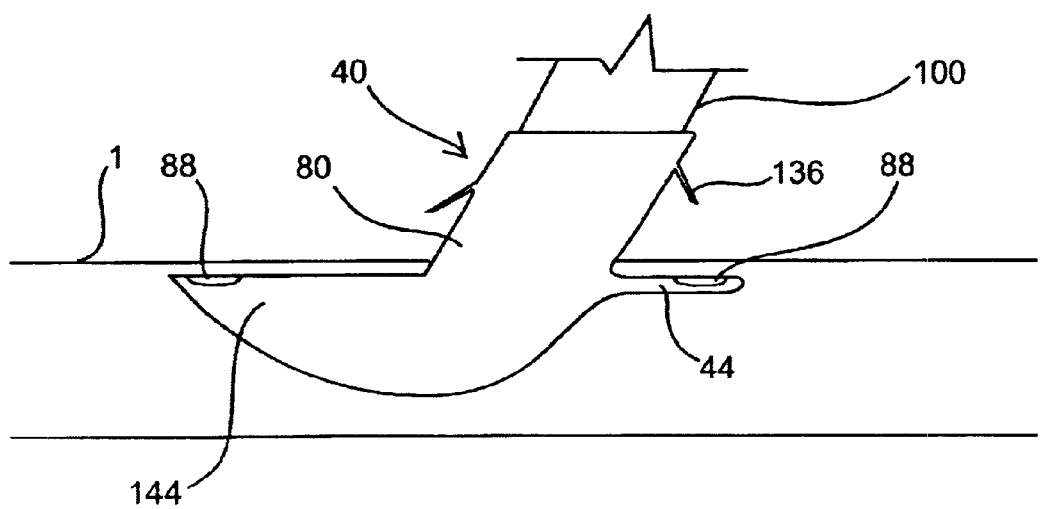
Figure 14F:
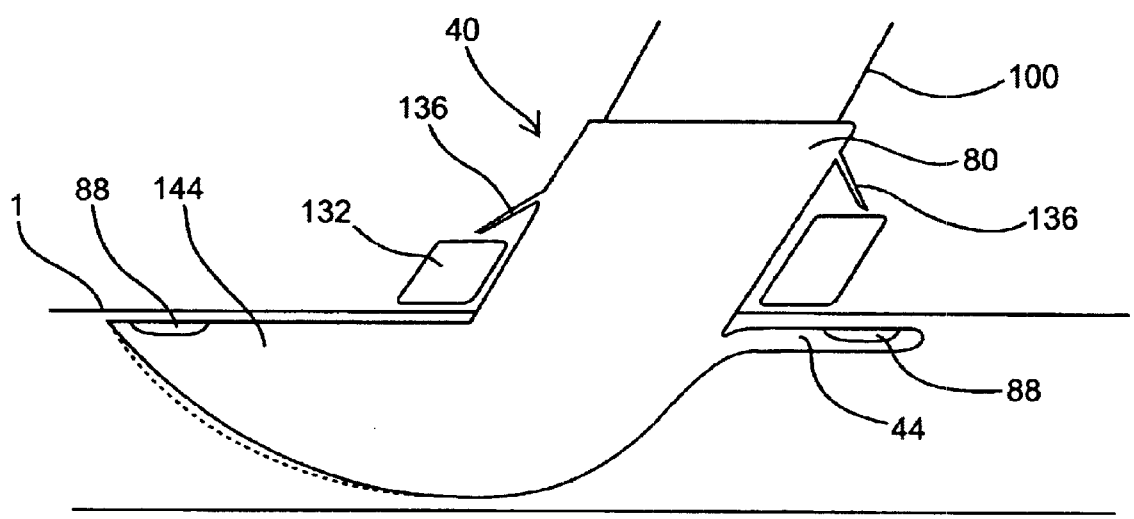

Thus, when the end-side fitting is completely inside the host vessel, the exterior surface of the leading petal contacts the interior surface of the host vessel. The leading petal 144 may be slightly squeezed together (by hand or using clamps or the like) to produce a better transition from the guidewire to the base of the fitting. Once the end-side fitting is advanced until the base 80 of the fitting resides approximate the opening through the host vessel wall, the rear petal 44 must be advanced through the opening. As shown in FIGS. 14c and 14d, the rear petal 44 can be deflected towards the base 80 of the end-side fitting using the guidewire or due to the force exerted by the host vessel wall as the proximal end of the end-side fitting is advanced through the host vessel wall. The rear petal 44 is designed so it is capable of bending towards the base of the fitting but is unable to readily deflect towards the leading petal 144. This anchors the end-side fitting inside the host vessel once the rear petal 44 is advanced through the host vessel wall. Preferably, the length of the rear petal 44 is less than the diameter of the host vessel and is positioned so the rear petal 44 may be advanced through the opening without the leading petal 144 or base of the fitting having to deform the posterior surface of the host vessel. Once positioned entirely through the host vessel wall, a support device 132 is used to lock the end-side fitting inside the host vessel and prevent blood leakage between the opening through the host vessel wall 1 and the base 80 of the end-side fitting. Tabs 136 anchor the support device 132 in place, compressing the host vessel wall against the leading petal 144 and rear petal 44 of the end-side fitting.

As a result of the sheathless deployment process, these end-side fittings may be fabricated using any biocompatible material (e.g. nickel titanium, PET, PTFE, urethane, silicone, polyester, etc.) or their composites via manufacturing processes such as injection molding, blow molding, dipping, etc. In addition, this mitigates concerns of maximum strain imposed on the petals (when made of certain materials) when compressing the end-side fitting into a reduced diameter for advancing through a deployment sheath.

Figure 7:
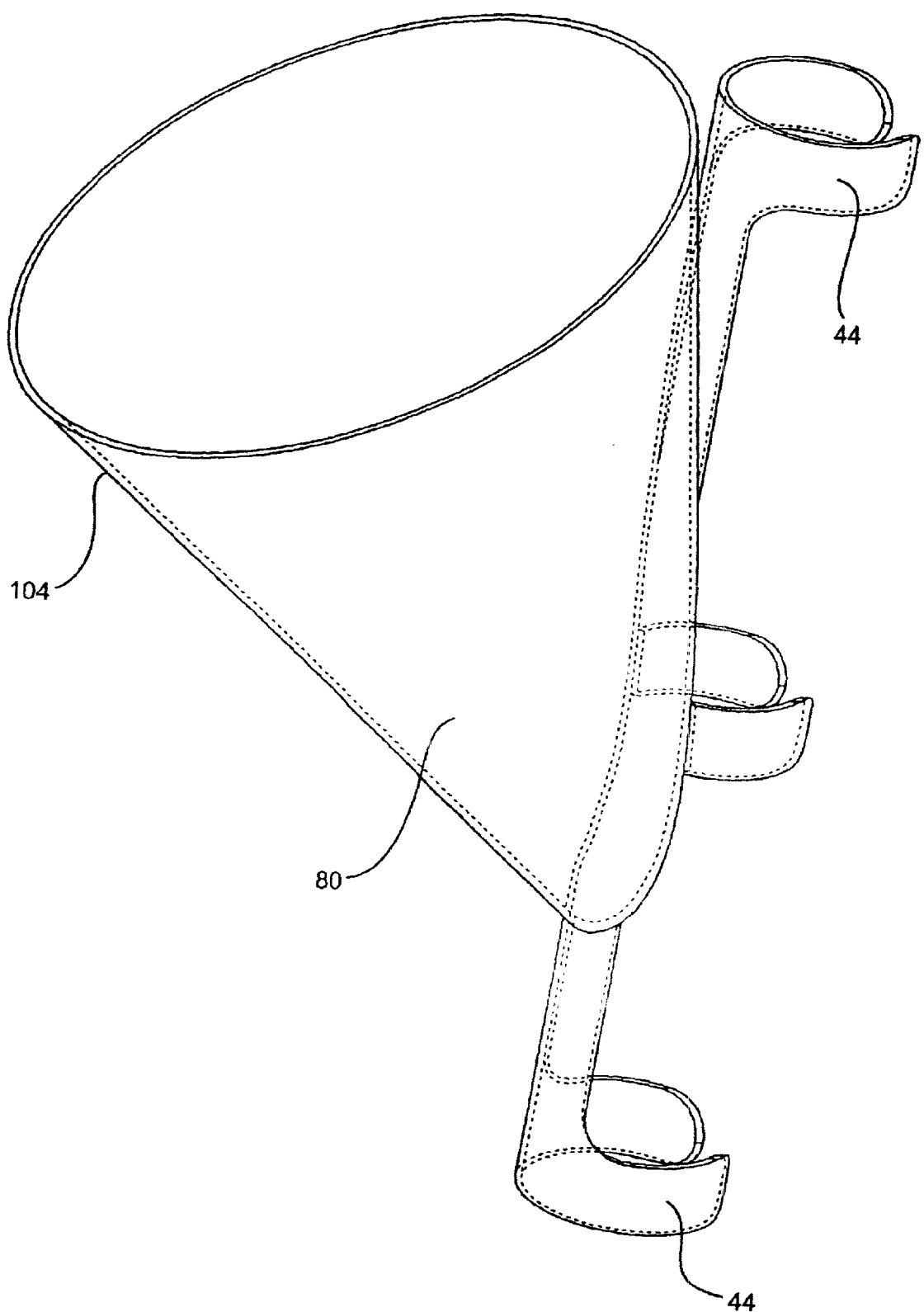
FIG. 7 shows a small vessel end-side fitting embodiment having a funneled stem.

Another sheathless end-side fitting is shown in FIG. 7. This end-side fitting is designed for small vessels. The petals 44 are configured to pass through an opening and into the host vessel while being constrained with a dilator or inside slotted tubing. As a result, the base 80 of the end-side fitting does not need to pass through the lumen of a deployment sheath. This enables the inclusion of design features that would otherwise be difficult to implement and realize. For example, the base 80 of the fitting may incorporate a funneled proximal transition section 104 for accepting bypass grafts having a larger cross-sectional diameter than that of the host vessel to which the end-side fitting becomes attached. This is especially relevant when considering that saphenous veins are oriented with the larger diameter end attached to the coronary arteries because of the valves that need to be oriented so they permit blood to flow from the aorta to the coronary artery. In addition, many physicians elect to use oversized bypass grafts (especially when using synthetic materials) to minimize the potential for thrombosis of the bypass grafts. As a result, the cross-sectional diameter is larger than that of the host vessel and the bypass graft needs to be ovalized or otherwise altered to produce the anastomosis.

Figure 9A:
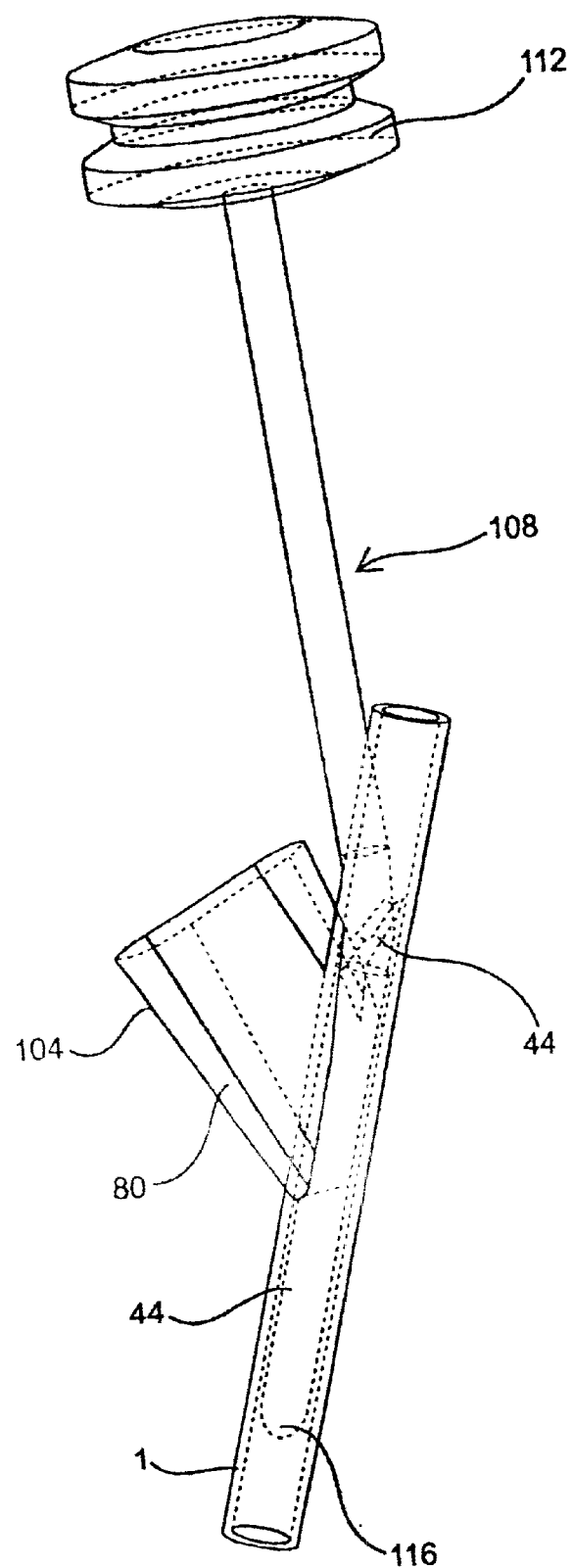
FIGS. 9a and 9b show the deployment of an end-side fitting using the dilator deployment device of FIG. 8.
Figure 9B:
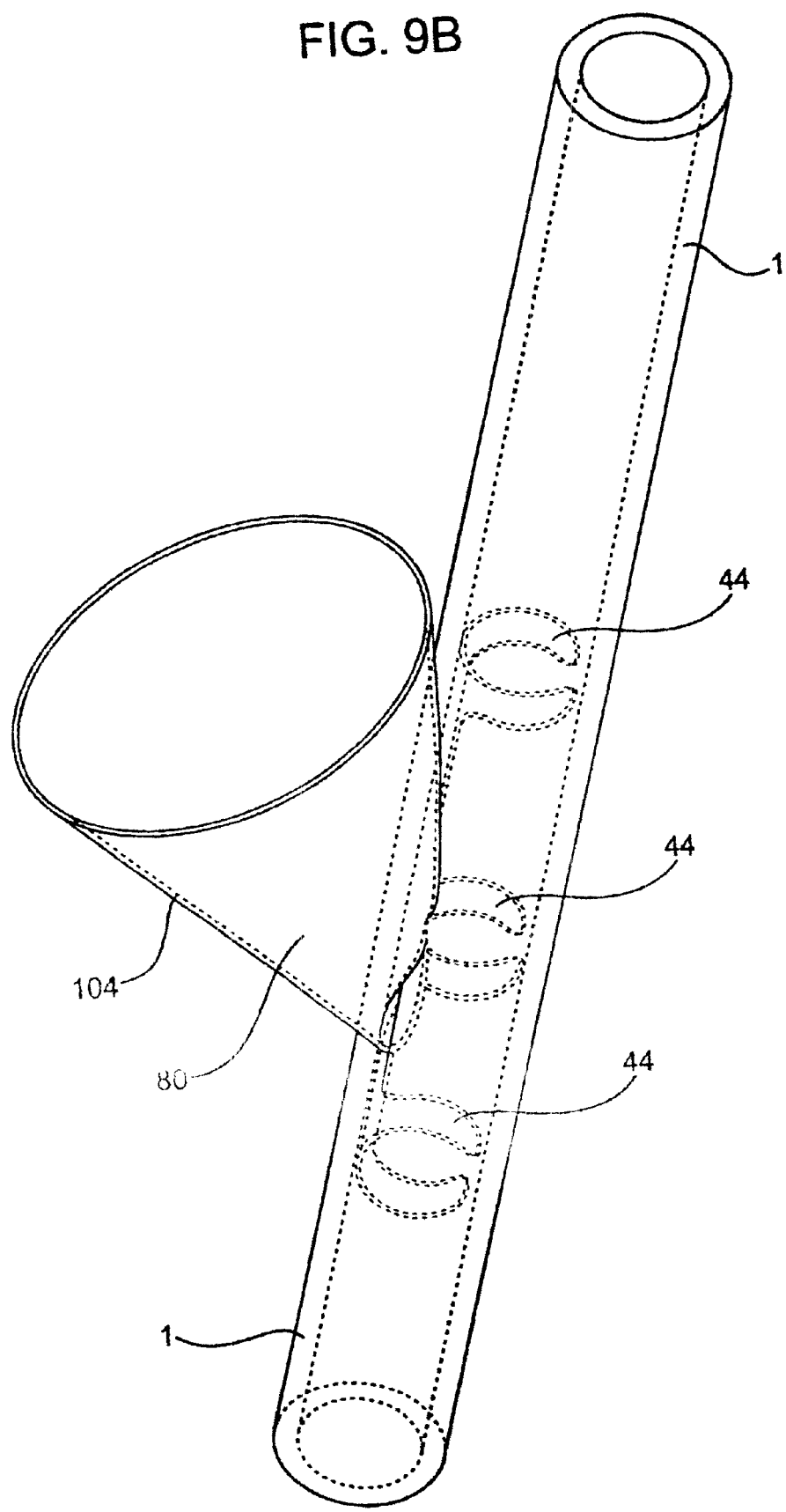
Figure 10B:
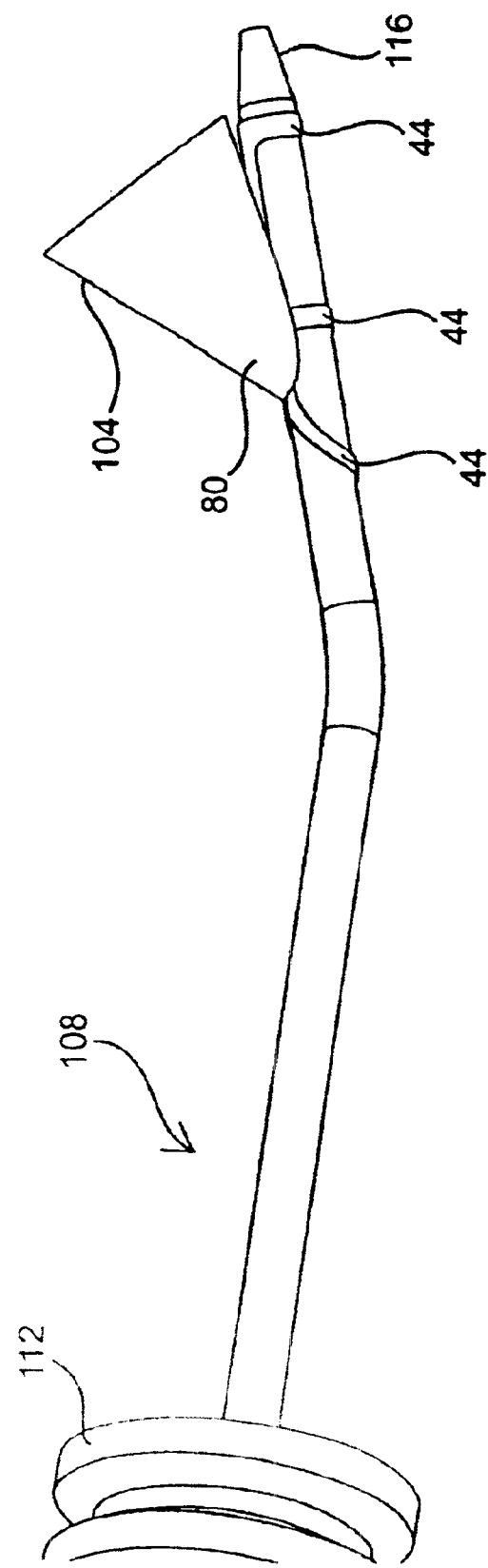
FIG. 10b shows the deployment of the end-side fitting of FIG. 10a using the dilator deployment device of FIG. 8.

FIG. 8 shows a dilator 108 used to advanced the end-side fitting shown in FIG. 7 into the host vessel. The dilator includes a hub 112 for the physician to remotely manipulate the dilator, a tapered distal end 116 to dilate the opening through the vessel wall, and a lumen (not shown) so the dilator may pass over a guidewire or needle and through the opening into the host vessel. FIG. 9a shows the end-side fitting supported on this dilator for deployment into the host vessel wall. Once positioned, the dilator is removed, leaving the end-side fitting inside the host vessel wall as shown in FIG. 9b. FIGS. 10a and 10b show an alternative end-side fitting embodiment and deployment process. In this case, the end-side fitting is oriented so the proximal end of the fitting is inserted first into the host vessel, over the dilator.

Figure 12:
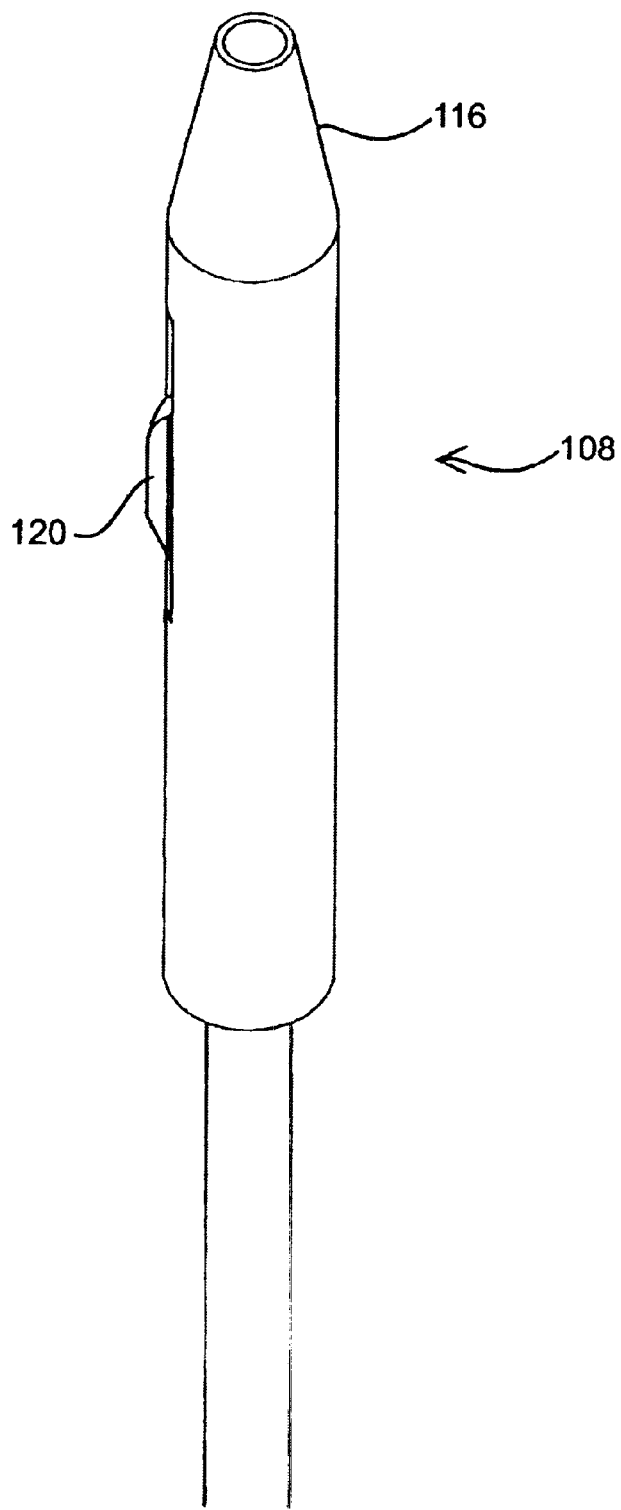
FIG. 12 shows a dilator deployment device having a cutting edge.

Under certain circumstances, it is preferred that the dilator be equipped with a cutting element to remove the stress on the host vessel wall. FIG. 12 shows a standard dilator 108 with a movable cutting element 120 that is capable of making a longitudinal incision through the host vessel wall.

Figure 13:
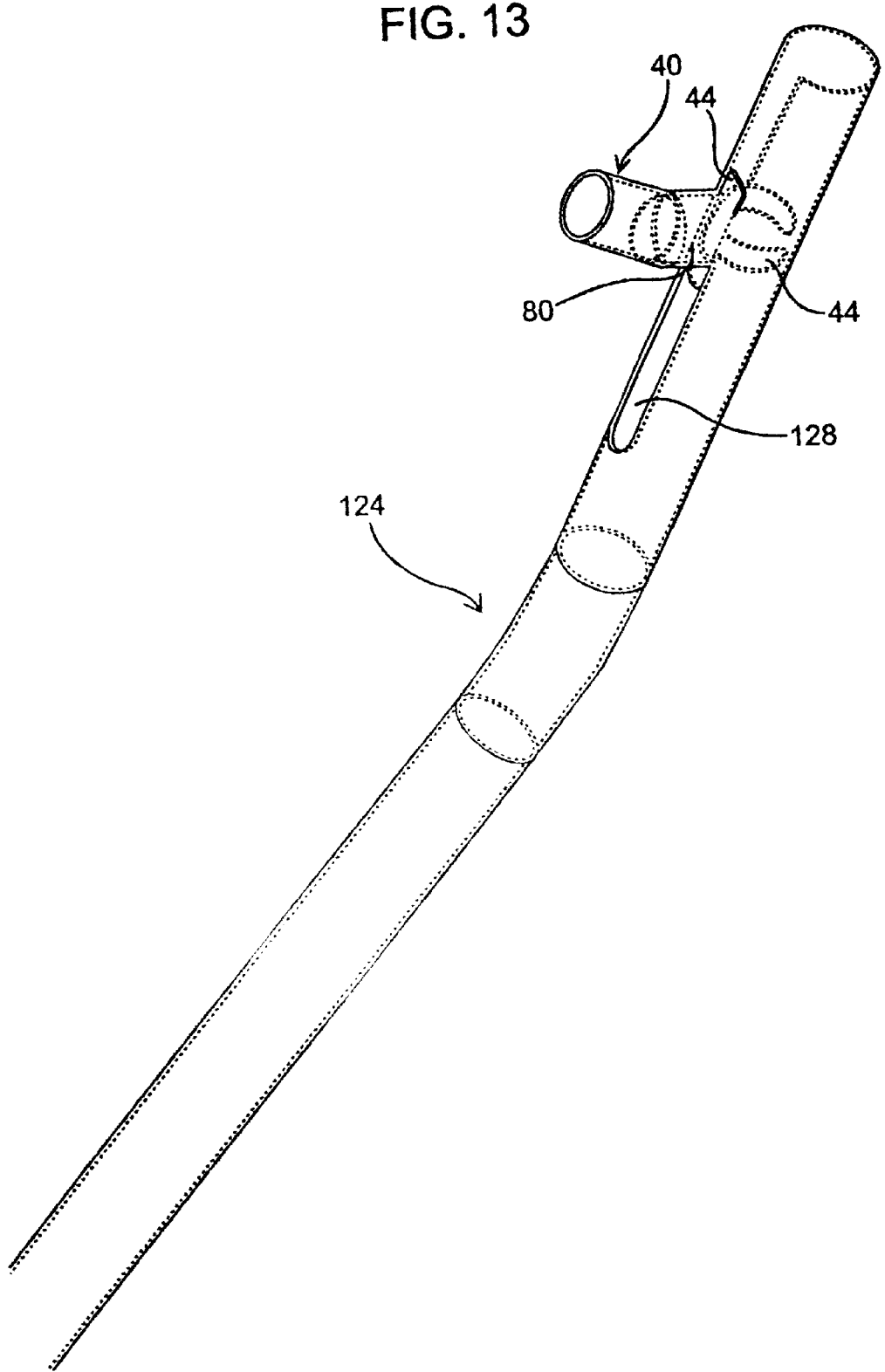
FIG. 13 shows a slotted deployment sheath for positioning bypass grafts attached to small vessel end-side fittings.

As opposed to advancing the petals 44 of an end-side fitting over a dilator, the petals may be constrained inside a slotted tubing 124 as shown in FIG. 13. The slotted tubing 124 contains an opening 128 through which the end-side fitting may be advanced into the host vessel. The slotted tubing 124 is inserted over a dilator and into the host vessel. Once inside, the dilator is removed and the end-side fitting is advanced. The front petal(s) and side petal(s) are easily advanced into the host vessel, but the rear petals must be deflected forward using a stylet or deflect towards the base of the fitting as previously described. To remove the slotted tubing 124 from around the end-side fitting, the slot 128 is positioned around the base of the end-side fitting and the slotted-tubing is retracted. This prevents having to expand the opening through the host vessel wall by the diameter of the slotted tubing, which could permanently deform the opening through the host vessel wall and hinder hemostasis between the opening and the base. Once the end-side fitting is completely positioned inside the host vessel, a support device (not shown) is locked to the base of the end-side fitting compressing the host vessel wall against the petals of the end-side fitting.

We claim:

1. An end-side anastomosis connector for connecting a graft to a host vessel having a wall with an opening therein and having inner and outer surfaces, the inner surface having a radius of curvature comprising an elongated fitting having proximal and distal extremities and configured to form a seal with the opening in the host vessel wall, the proximal extremity of the elongate fitting having a first fixation mechanism adapted to be connected to the graft, the distal extremity of the elongate fitting having a second fixation mechanism adapted to be secured into the opening in the wall of the host vessel, the second fixation mechanism including a leading petal having a cross-section with a radius of curvature approximating the radius of curvature of the inner surface of the host vessel and adapted to engage the inner surface of the wall in the vicinity of the opening therein, said second fixation mechanism also including a first portion generally overlying the leading petal and being adapted to be engaged by the outer surface of the wall in the vicinity of the opening therein and a second portion extending away from the first portion and being adapted to be engaged by the outer surface of the wall in the vicinity of the opening, said second fixation mechanism also including a rear petal having a free position extending away from the leading petal and underlying the second portion and being adapted to be engaged by the inner surface of the wall in the vicinity of the opening therein, said rear petal being deflectable away from the free position to facilitate entrance of the rear petal through the opening in the wall.

2. The connector of claim 1 wherein the rear petal is deflectable towards the proximal extremity.

3. The connector of claim 1 wherein the rear petal has a length such that the elongated fitting can be advanced through the host vessel opening without the proximal or distal extremities deforming a posterior surface of the host vessel upon introduction of the fitting into the host vessel.

4. The connector of claim 1 wherein the elongated fitting defines proximal and distal openings configured to receive a guidewire.

5. The connector of claim 1 wherein the first fixation mechanism of the elongated fitting comprises a locking mechanism to secure a support device.

6. The connector of claim 1 wherein the first fixation mechanism is selected from a group consisting of tabs and threads.

7. The connector of claim 1 further comprising a support device configured for attachment to the proximal extremity of the elongate fitting.

8. The connector of claim 7 wherein the support device comprises a funneled section for relieving stress on the graft.

9. The connector of claim 7 wherein the support device defines a curved proximal end.

10. The connector of claim 7 wherein the support device has a curved distal end having a curvature matching the curvature of the host vessel.

11. The connector of claim 7 wherein the support device comprises a slotted member having edges.

12. The connector of claim 11 wherein the support device comprises a latching mechanism to lock the edges together.

13. The connector of claim 7 further comprising a clip for securing the support device to the proximal extremity of the elongate fitting.

14. The connector of claim 7 wherein said support device comprises a flared distal end.

* * * * *